(12) United States Patent
Ackerman et al.

(10) Patent No.: US 12,325,750 B2
(45) Date of Patent: Jun. 10, 2025

(54) ANTI-DECTIN-2 ANTIBODIES AND METHODS OF USING

(71) Applicant: Bolt Biotherapeutics, Inc., Redwood City, CA (US)

(72) Inventors: Shelley Erin Ackerman, Redwood City, CA (US); David Dornan, Redwood City, CA (US); Karla A. Henning, Redwood City, CA (US); Justin A. Kenkel, Redwood City, CA (US)

(73) Assignee: Bolt Biotherapeutics, Inc., Redwood City, CA (US)

(*) Notice: Subject to any disclaimer, the term of this patent is extended or adjusted under 35 U.S.C. 154(b) by 144 days.

(21) Appl. No.: 18/356,928

(22) Filed: Jul. 21, 2023

(65) Prior Publication Data

US 2023/0406939 A1 Dec. 21, 2023

Related U.S. Application Data

(60) Division of application No. 17/592,323, filed on Feb. 3, 2022, now Pat. No. 11,753,474, which is a continuation of application No. PCT/US2021/030466, filed on May 3, 2021.

(60) Provisional application No. 63/018,952, filed on May 1, 2020.

(51) Int. Cl.
C07K 16/28 (2006.01)

(52) U.S. Cl.
CPC .... C07K 16/2851 (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 10,995,148 B2 | 5/2021 | Avila et al. | |
| 2019/0336615 A1 | 11/2019 | Thompson et al. | |
| 2020/0354447 A1 | 11/2020 | Thompson et al. | |
| 2021/0283262 A1 | 9/2021 | Dominy et al. | |
| 2022/0127366 A1 | 4/2022 | Fotakis et al. | |
| 2022/0169737 A1 | 6/2022 | Fotakis et al. | |

FOREIGN PATENT DOCUMENTS

| WO | WO 2017/117269 A1 | 7/2017 |
|---|---|---|
| WO | WO 2019/006038 A1 | 1/2019 |

OTHER PUBLICATIONS

Giordano et al. (J Immunother Cancer 2023; 11(suppl 1):A1-A1731; 720 A phase 1/2 study of BDC-3042, a novel Dectin-2 agonistic antibody, in patients with advanced cancers).*
Brown et al., "C-type lectins in immunity and homeostasis," *Nat. Rev. Immunol.*, 18: 374-389 (2018).
Cantrell et al., "Uterine Carcinosarcoma: A Review of the Literature," *Gynecol. Oncol.*, 137(3): 581-588 (2015).
Casset et al., "A Peptide Mimetic of an Anti-CD4 Monoclonal Antibody by Rational Design," *Biochem. Biophys. Res. Commun.*, 307(1): 198-205 (2003).
Chen et al., "Selection and Analysis of an Optimized Anti-VEGF Antibody: Crystal Structure of an Affinity-matured Fab in Complex with Antigen," *J. Mol. Biol.*, 293(4): 865-881 (1999).
Cheng et al., "A pan-cancer single-cell transcriptional atlas of tumor infiltrating myeloid cells," *Cell*, 184: 792-809 (2021).
De Pascalis et al., "Grafting of 'Abbreviated' Complementarity-Determining Regions Containing Specificity-Determining Residues Essential for Ligand Contact to Engineer a Less Immunogenic Humanized Monoclonal Antibody," *J. Immunol.*, 169(6): 3076-3084 (2002).
Goyal et al., "The Interaction of Human Pathogenic Fungi with C-Type Lectin Receptors," *Front. Immunol.*, 9: 1261 (2018).
Kenkel et al., "BDC-3042: A Dectin-2 Agonist Antibodies for Tumor-Associated Macrophage-Directed Immunotherapy," *Journal for Immuno Therapy of Cancer*, 10(Suppl. 2): A1397, Abstract 1348 (2022).
Kenkel et al., "Dectin-2 Agonist Antibodies Reprogram Tumor-Associated Macrophages to Drive Anti-Tumor Immunity," *Cancer Research*, 82(Suppl. 12): Abstract 2883 (2022).
Kenkel et al., "Dectin-2, a Novel Target for Tumor Macrophage Reprogramming in Cancer Immunotherapy," *Journal for Immuno Therapy of Cancer*, 9(Suppl. 2): Abstract 862 (2021).
Kersher et al., "The Dectin-2 family of C-type lectin-like receptors: an update," *Int. Immunol.*, 25(5): 271-277 (2013).
Kim et al.," Tumor-Associated Macrophages and Neutrophils in Tumor Microenvironment," *Mediators of Inflammation*, 2016: 6058147 (2016).
Kimura et al., "The innate immune receptor Dectin-2 mediates the phagocytosis of cancer cells by Kupffer cells for the suppression of liver metastasis," *PNAS*, 113(49): 14097-14102 (2016).
Lamminmäki et al., "Crystal Structure of a Recombinant Anti-estradiol Fab Fragment in Complex with 17β-Estradiol," *J. Biol. Chem.*, 276(39): 36687-36694 (2001).
Lloyd et al., "Modelling the Human Immune Response: Performance of a 1011 Human Antibody Repertoire Against a Broad Panel of Therapeutically Relevant Antigens," *Protein Eng. Des. Sel.*, 22(3): 159-168 (2009).
MacCallum et al., "Antibody-antigen Interactions: Contact Analysis and Binding Site Topography," *J. Mol. Biol.*, 262(5): 732-745 (1996).

(Continued)

*Primary Examiner* — Sharon X Wen
(74) *Attorney, Agent, or Firm* — Leydig, Voit & Mayer, Ltd.

(57) ABSTRACT

The invention relates to dendritic cell-associated C-type lectin 2 (Dectin-2) binding agents, nucleic acids comprising the inventive binding agents, vectors and cells comprising the inventive nucleic acids, and compositions thereof. The invention also relates to methods of providing the inventive binding agents, methods for treating a disease, disorder, or condition in a mammal, and methods of stimulating an antigen presenting cell.

29 Claims, 7 Drawing Sheets
Specification includes a Sequence Listing.

(56) References Cited

OTHER PUBLICATIONS

Molgora et al., "Turning enemies into allies—reprogramming tumor-associated macrophages for cancer therapy," *Med*, 2: 666-681 (2021).

Padlan et al., "Structure of an Antibody-Antigen Complex: Crystal Structure of HyHEL-10 Fab-Lysozyme Complex," *Proc. Natl. Acad. Sci. USA.*, 86(15): 5938-5942 (1989).

Parsons et al., "Dectin-2 Regulates the Effector Phase of House Dust Mite—Elicited Pulmonary Inflammation Independently From Its Role in Sensitization," *The Journal of Immunology*, 192(4): 1361-1371 (2014).

Piche-Nicholas et al., "Changes in Complementarity-Determining Regions Significantly Alter IgG Binding to the Neonatal Fc Receptor (FcRn) and Pharmacokinetics," *mAbs.*, 10(1): 81-94 (2018).

R&D Systems (bio-techne), "Human Dectin-2/CLEC6A Antibody," Monoclonal Mouse $IgG_{2B}$ Clone # 545925, Catalog No. MAB31141 (2020).

Richards et al., "Optimization of antibody binding to FcγRIIa enhances macrophage phagocytosis of tumor cells," *Mol. Cancer Ther.*, 7(8): 2517-2527 (2008).

Robinson et al., "Dectin-2 is a Syk-coupled pattern recognition receptor crucial for Th17 responses to fungal infection," *J. Exp. Med.*, 206(9): 2037-2051 (2009).

Rudikoff et al., "Single Amino Acid Substitution Altering Antigen-Binding Specificity," *Proc. Natl. Acad. Sci. USA.*, 79(6): 1979-1983 (1982).

Saijo et al., "Dectin-1 and Dectin-2 in innate immunity against fungi," *Int. Immunol.*, 23(8): 467-472 (2011).

Saijo et al., "Dectin-2 Recognition of α-Mannans and Induction of Th17 Cell Differentiation Is Essential for Host Defense against *Candida albicans,*" *Immunity*, 32: 681-691 (2010).

Sato et al., "Dectin-2 Is a Pattern Recognition Receptor for Fungi That Couples with the Fc Receptor γ Chain to Induce Innate Immune Responses," *J. Biol. Chem.*, 281(50): 38854-38866 (2006).

Schroeder et al., "Structure and Function of Immunoglobulins," *J. Allergy Clin. Immunol.*, 125 (2 Suppl. 2): S41-S52 (2010).

Vajdos et al., "Comprehensive Functional Maps of the Antigen-binding Site of an Anti-ErbB2 Antibody Obtained with Shotgun Scanning Mutagenesis," *J. Mol. Biol.*, 320(2): 415-428 (2002).

Van Dalen et al., "Molecular Repolarisation of Tumour-Associated Macrophages," *Molecules*, 24: 9 (2019).

Wu et al., "Humanization of a Murine Monoclonal Antibody by Simultaneous Optimization of Framework and CDR Residues," *J. Mol. Biol.*, 294(1): 151-162 (1999).

European Patent Office, International Search Report in International Patent Application No. PCT/US2021/030466 (Aug. 31, 2021).

European Patent Office, Written Opinion in International Patent Application No. PCT/US2021/030466 (Aug. 31, 2021).

\* cited by examiner

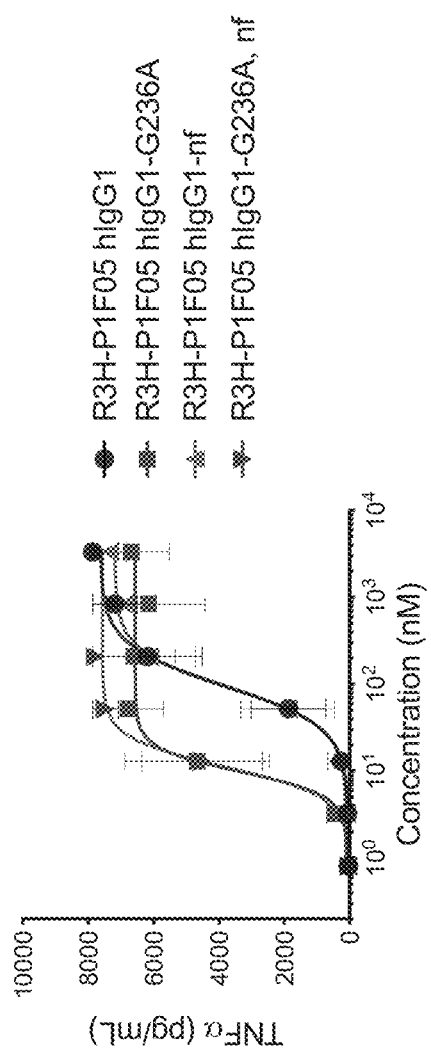
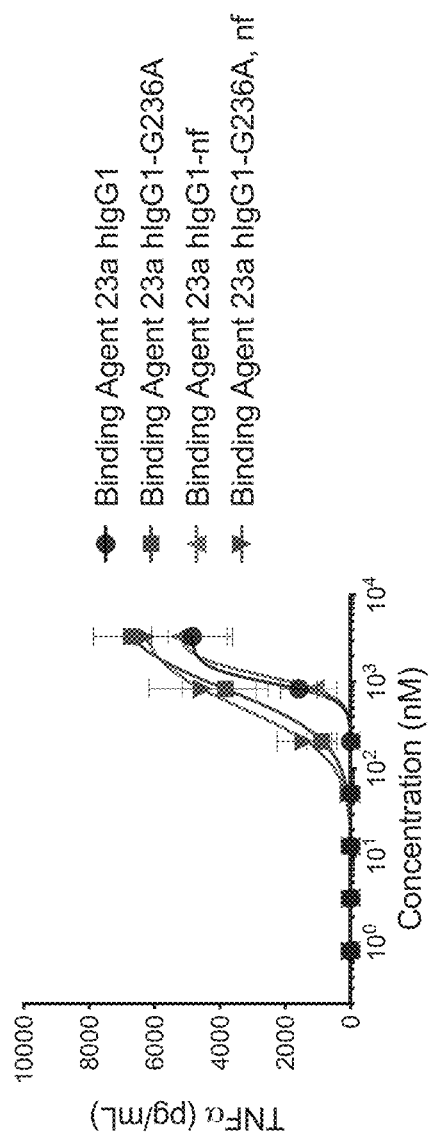
FIG. 5A
FIG. 5B

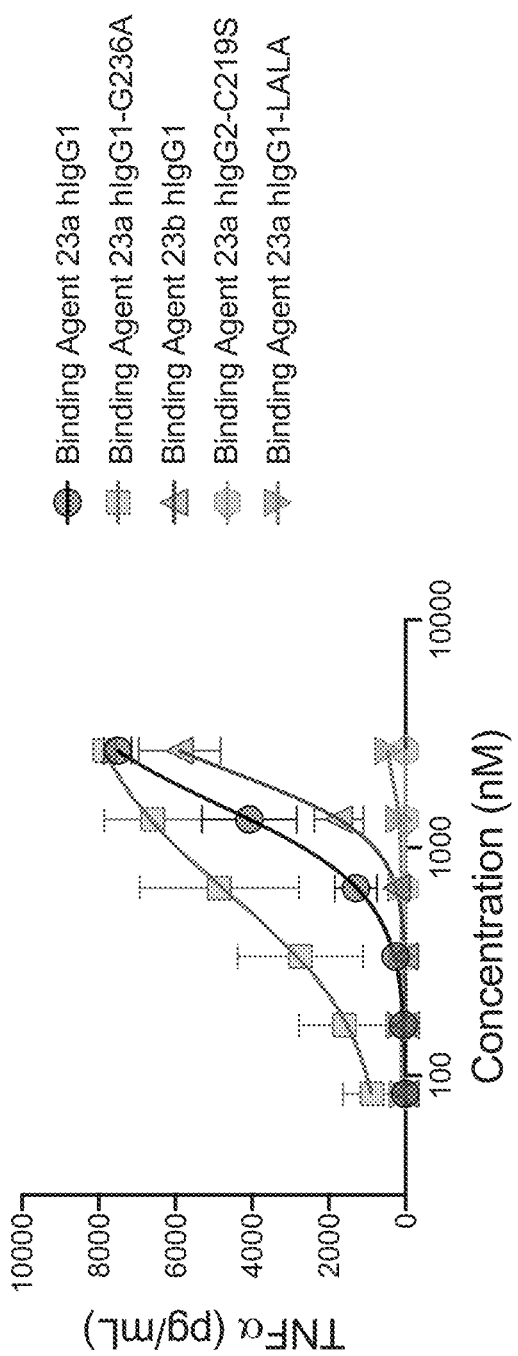

ANTI-DECTIN-2 ANTIBODIES AND METHODS OF USING

CROSS-REFERENCE TO PRIOR APPLICATIONS

This application is a divisional of copending U.S. patent application Ser. No. 17/592,323, filed Feb. 3, 2022, which is a continuation of International Patent Application No. PCT/US2021/030466, filed May 3, 2021, which claims benefit to U.S. Provisional Patent Application No. 63/018,952, filed May 1, 2020, each of which is hereby incorporated by reference in its entirety.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 447,020 Byte Extensible Markup Language (XML) file named "767961 ST26.xml," created on Jul. 21, 2023.

BACKGROUND OF THE INVENTION

Dectin-2 (dendritic cell-associated C-type lectin 2, CLEC6A, CLEC4N, CLECSF10) belongs to the family of C-type lectin receptors. Dectin-2 is thought to primarily play a role in antifungal immunity, by binding to carbohydrate ligands such as mannans, which are typically found on fungal cell surfaces. Dectin-2 is expressed mainly by cells of myeloid lineage, including monocytes, macrophages and dendritic cells. Activation of the Dectin-2 pathway can elicit a pro-inflammatory immune response in these cells, including activation of the NF-κB pathway and subsequent production of pro-inflammatory cytokines, as well as increased phagocytic activity. A pro-inflammatory immune response driven by Dectin-2 activation on Dectin-2 expressing myeloid cells in the tumor microenvironment can ultimately lead to an anti-tumor immune response. Accordingly, agents that bind to Dectin-2, including those that act as Dectin-2 agonists, can be useful in the treatment of cancer.

There is still a need for additional methods of preventing and treating cancer given that most cancer patients ultimately fail standard of care therapies. Dectin-2 binding agents, including those that act to agonize the Dectin-2 signaling pathway, can be used to address this need.

BRIEF SUMMARY OF THE INVENTION

Provided herein are Dectin-2 binding agents comprising an immunoglobulin heavy chain variable region polypeptide and an immunoglobulin light chain variable region polypeptide. In some embodiments, the Dectin-2 binding agents comprise an immunoglobulin heavy chain variable region of any one of SEQ ID NOs: 243-282 or 324, or at least the CDRs thereof; and an immunoglobulin light chain variable region of any one of SEQ ID NOs: 283-322 or at least the CDRs thereof. In other embodiments, the Dectin-2 binding agents comprise an immunoglobulin heavy chain variable region polypeptide with an amino acid sequence that is at least 90% identical to any one of SEQ ID NOs: 243-282 or 324, and an immunoglobulin light chain variable region polypeptide with an amino acid sequence that is at least 90% identical to any one of SEQ ID NOs: 283-322. In yet other embodiments of the Dectin-2 binding agent, the immunoglobulin heavy chain variable region polypeptide comprises a complementarity determining region 1 (HCDR1) comprising any one of SEQ ID NOs: 1-30, a complementarity determining region 2 (HCDR2) comprising any one of SEQ ID NOs: 31-64, and a complementarity determining region 3 (HCDR3) comprising any one of SEQ ID NOs: 65-103 or 323; and/or the immunoglobulin light chain variable region polypeptide comprises a complementarity determining region 1 (LCDR1) comprising any one of SEQ ID NOs: 104-125, a complementarity determining region 2 (LCDR2) comprising any one of SEQ ID NOs: 126-148, and a complementarity determining region 3 (LCDR3) comprising any one of SEQ ID NOs: 149-181. In further embodiments, the Dectin-2 binding agents comprise an immunoglobulin heavy chain polypeptide of any one of SEQ ID NOs: 328-345, and an immunoglobulin light chain polypeptide of any one of SEQ ID NOs: 325-327. In still further embodiments, the Dectin-2 binding agents comprise an immunoglobulin heavy chain polypeptide that is at least 90% identical to any one of SEQ ID NOs: 328-345, and an immunoglobulin light chain polypeptide that is at least 90% identical to any one of SEQ ID NOs: 325-327. Also provided are nucleic acids encoding the Dectin-2 binding agents, or the individual heavy and light chains thereof vectors and cells comprising the nucleic acids; and compositions comprising the binding agents or nucleic acids.

Also provided is a method of preparing a binding agent as described herein, which method comprises expressing in a cell one or more nucleic acids encoding the heavy and light chain variable region polypeptides of the binding agent.

Also provided is a method for treating a disease, disorder, or condition in a mammal that is responsive to Dectin-2 activation or inhibition, which method comprises administering a binding agent as described herein, or conjugate thereof, to the mammal.

Also provided is a method of stimulating an antigen presenting cell (APC), which method comprises contacting an APC with a Dectin-2 binding agent at a dose and for a period of time sufficient to enhance Dectin-2 signaling in the APC, thereby generating a stimulated APC.

Additional aspects and embodiments of the invention are as provided in the following detailed description.

BRIEF DESCRIPTION OF THE DRAWINGS

FIGS. 5A and 5B are graphs of TNFα (pg/mL) secreted by M-CSF-treated human monocytes stimulated with different concentrations (nM) of each of the indicated antibodies.

FIG. 6 is a graph of TNFα (pg/mL) secreted by M-CSF-treated human monocytes stimulated with different concentrations (nM) of each of the indicated antibodies.

DETAILED DESCRIPTION OF THE INVENTION

Figure 1:
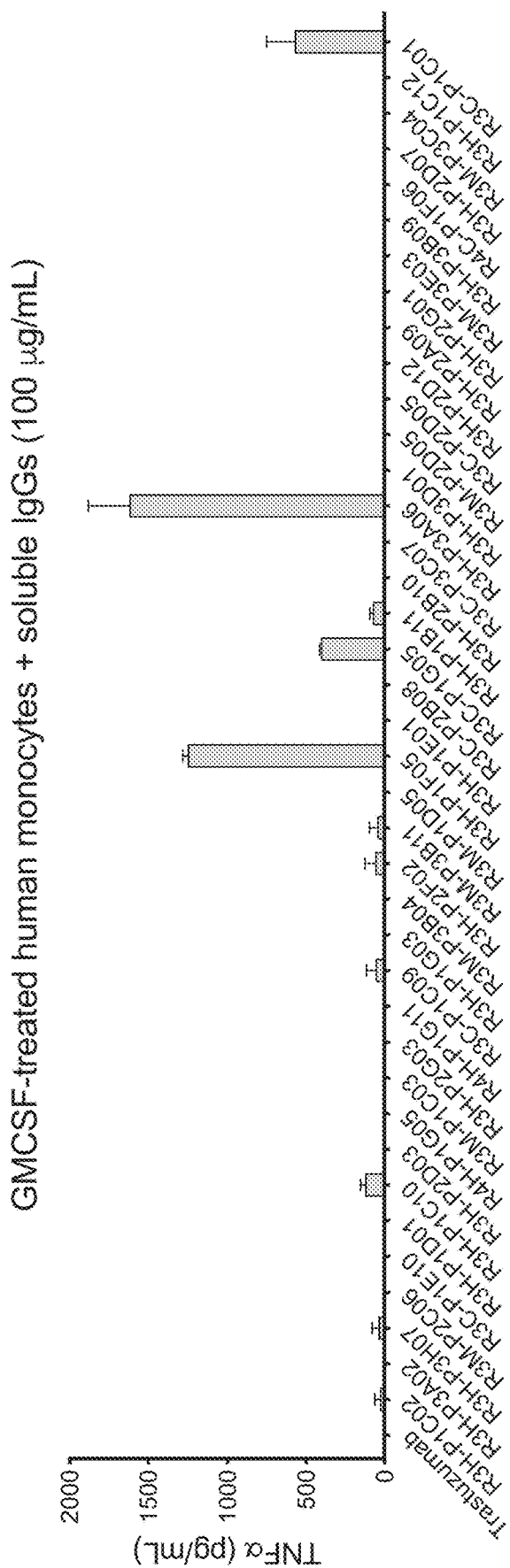
FIG. 1 is a bar graph of Tumor Necrosis Factor alpha (TNFα (pg/mL)) secreted by GM-CSF-treated human monocytes which have been exposed to certain soluble anti-Dectin-2 antibodies at a concentration of 100 μg/mL.

The invention provides a Dectin-2 binding agent comprising an immunoglobulin heavy chain variable region polypeptide and an immunoglobulin light chain variable region polypeptide. The Dectin-2 binding agent specifically binds Dectin-2, and allows for targeting Dectin-2 expressing cells, for instance, to activate (induce) one or more Dectin-2-associated pathways in the Dectin-2 expressing cells.

In some embodiments, the Dectin-2 binding agent binds Dectin-2, which is a receptor, without substantially inhibiting or preventing binding of one or more of its natural ligands to Dectin-2. In some embodiments, the Dectin-2 binding agent agonistically binds Dectin-2, thereby completely or partially activating Dectin-2 signaling in Dectin-2 expressing cells (e.g., for therapeutic purposes). In some embodiments, the Dectin-2 binding agent binds Dectin-2 as a monomer. In some embodiments, the Dectin-2 binding agent binds Dectin-2 as a homodimer or a heterodimer with another protein, such as Dectin-3. When the Dectin-2 binding agent binds to Dectin-2 as a homodimer or heterodimer (e.g., Dectin-2/Dectin-3 heterodimer), the binding agent can bind to the Dectin-2 prior to formation of the homodimer or heterodimer or, in other embodiments, the Dectin-2 binding agent binds Dectin-2 after it has formed a homodimer or heterodimer.

In some embodiments, the Dectin-2 binding agent binds to human Dectin-2, for example, a protein comprising SEQ ID NO: 346 (MMQEQQPQSTEKRGWLSLRLWSVAGI-SIALLSACFIVSCVVTYHFTYGETGKRLSEL HSYHSSLTCFSEGTKVPAWGCCPASWKSFGSSCYFIS-SEEKVWSKSEQNCVEMGAHL VVFNTEAEQN-FIVQQLNESFSYFLGLSDPQGNNNWQW IDKTPYEKNVRFWHLGEPN HSAEQCA-SIVFWKPTGWGWNDVICETRRNSICEMNKIYL). However, binding agents that bind to any Dectin-2 homolog or paralog also are encompassed. In some embodiments, the Dectin-2 protein comprises at least about 70%, about 75%, about 80%, about 85%, about 90%, about 91%, about 92%, about 93%, about 94%, about 95%, about 96%, about 97%, about 98%, about 99%, or more sequence identity to SEQ ID NO: 346. In some embodiments, the binding agent binds human and/or mouse Dectin-2.

Nucleic acid or amino acid sequence "identity," as referenced herein, can be determined by comparing a nucleic acid or amino acid sequence of interest to a reference nucleic acid or amino acid sequence. The percent identity is the number of nucleotides or amino acid residues that are the same (i.e., that are identical) as between the optimally aligned sequence of interest and the reference sequence divided by the length of the longest sequence (i.e., the length of either the sequence of interest or the reference sequence, whichever is longer). Alignment of sequences and calculation of percent identity can be performed using available software programs. Examples of such programs include CLUSTAL-W, T-Coffee, and ALIGN (for alignment of nucleic acid and amino acid sequences), BLAST programs (e.g., BLAST 2.1, BL2SEQ, BLASTp, BLASTn, and the like) and FASTA programs (e.g., FASTA3x, FAS™, and SSEARCH) (for sequence alignment and sequence similarity searches). Sequence alignment algorithms also are disclosed in, for example, Altschul et al., *J. Molecular Biol.*, 215(3): 403-410 (1990), Beigert et al., Proc. Natl. Acad. Sci. USA, 106(10): 3770-3775 (2009), Durbin et al., eds., *Biological Sequence Analysis: Probalistic Models of Proteins and Nucleic Acids*, Cambridge University Press, Cambridge, UK (2009), Soding, Bioinformatics, 21(7): 951-960 (2005), Altschul et al., Nucleic Acids Res., 25(17): 3389-3402 (1997), and Gusfield, *Algorithms on Strings, Trees and Sequences*, Cambridge University Press, Cambridge UK (1997)). Percent (%) identity of sequences can be also calculated, for example, as $100 \times [(\text{identical positions})/\min(TG_A, TG_B)]$, where $TG_A$ and $TG_B$ are the sum of the number of residues and internal gap positions in peptide sequences A and B in the alignment that minimizes $TG_A$ and $TG_B$. See, e.g., Russell et al., *J. Mot Biol.*, 244: 332-350 (1994).

The binding agent comprises Ig heavy and light chain variable region polypeptides that together form the antigen binding site. Each of the heavy and light chain variable regions are polypeptides comprising three complementarity determining regions (CDR1, CDR2, and CDR3) connected by framework regions. The binding agent can be any of a variety of types of binding agents known in the art that comprise Ig heavy and light chains. For instance, the binding agent can be an antibody, an antigen-binding antibody "fragment," or a T-cell receptor.

In some embodiments, the binding agent is a whole (or complete) antibody, which comprises an antigen binding domain comprising the Ig heavy and light variable domains as well as a fragment crystallizable (Fc) domain. An exemplary antibody structure is a tetramer composed of two pairs of polypeptide chains, each pair having one "light" (a smaller chain, such as about 25 kDa) and one "heavy" chain (a larger chain, such as about 50-70 kDa), typically connected by disulfide bonds. Each chain is composed of structural domains, which are referred to as immunoglobulin domains. These domains are classified into different categories by size and function, e.g., variable domains or regions on the light and heavy chains ($V_L$ and $V_H$, respectively) and constant domains or regions on the light and heavy chains ($C_L$ and $C_H$, respectively). The N-terminus of each chain defines a variable region, typically about 100 to 110 or more amino acids (but not limited thereto), referred to as the paratope, primarily responsible for antigen recognition, i.e., the antigen binding domain. Light chains are classified as either kappa or lambda. Heavy chains are classified as gamma, mu, alpha, delta, or epsilon, which in turn define the immunoglobulin classes, IgG, IgM, IgA, IgD and IgE, respectively. The classes can be further divided into subclasses. For instance, there are four IgG subclasses (IgG1, IgG2, IgG3, and IgG4) in humans, named in order of their abundance in serum (i.e., IgG1 is the most abundant).

In some embodiments, the binding agent is an antigen-binding antibody "fragment," which is a construct that comprises at least an antigen-binding region of an antibody, alone or with other components that together constitute the antigen-binding construct. Many different types of antibody "fragments" are known in the art, including, for instance, (i) a Fab fragment, which is a monovalent fragment consisting of the $V_L$, $V_H$, $C_L$, and $CH_1$ domains, (ii) a F(ab')2 fragment, which is a bivalent fragment comprising two Fab fragments linked by a disulfide bridge at the hinge region, (iii) a Fv fragment consisting of the $V_L$ and $V_H$ domains of a single arm of an antibody, (iv) a Fab' fragment, which results from breaking the disulfide bridge of an $F(ab')_2$ fragment using mild reducing conditions, (v) a disulfide-stabilized Fv fragment (dsFv), and (vi) a single chain Fv (scFv), which is a monovalent molecule consisting of the two domains of the Fv fragment (i.e., V$_L$ and V$_H$) joined by a synthetic linker which enables the two domains to be synthesized as a single polypeptide chain.

The antibody or antibody fragments can be part of a larger construct, for example, a conjugate or fusion construct of the antibody fragment to additional regions. For instance, in some embodiments, the antibody fragment can be fused to an Fc region as described herein. In other embodiments, the antibody fragment (e.g., a Fab or scFv) can be part of a chimeric antigen receptor or chimeric T-cell receptor, for instance, by fusing to a transmembrane domain (optionally with an intervening linker or "stalk" (e.g., hinge region)) and optional intercellular signaling domain. For instance, the antibody fragment can be fused to the gamma and/or delta chains of a t-cell receptor, so as to provide a T-cell receptor like construct that binds Dectin-2. In yet another embodiment, the antibody fragment is part of a bispecific T-cell engager (BiTEs) comprising a CD1 or CD3 binding domain and linker.

The antibody or antigen-binding antibody fragment can be monospecific for Dectin-2, or can be bispecific or multi-specific. For instance, in bivalent or multivalent antibodies or antibody fragments, the binding domains can be different, and each binding domain can target different epitopes of the same antigen or target different antigens. In certain embodiments, the antibody or antigen binding antibody fragment is bispecific or multi-specific, wherein at least one binding domain specifically binds to Dectin-2, and at least one binding domain specifically binds a tumor targeting protein. Examples of tumor targeting proteins include 5T4, ABL, ABCF1, ACVR1, ACVR1B, ACVR2, ACVR2B, ACVRL1, ADORA2A, Aggrecan, AGR2, AICDA, AIF1, AIGI, AKAP1, AKAP2, AMH, AMHR2, ANGPT1, ANGPT2, ANGPTL3, ANGPTL4, ANPEP, APC, APOC1, AR, aromatase, ATX, AX1, AZGP1 (zinc-a-glycoprotein), B7.1, B7.2, B7-H1, BAD, BAFF, BAG1, BAIL BCR, BCL2, BCL6, BDNF, BLNK, BLR1 (MDR15), BIyS, BMP1, BMP2, BMP3B (GDFIO), BMP4, BMP6, BMP8, BMPR1A, BMPR1B, BMPR2, BPAG1 (plectin), BRCA1, C19orf10 (IL27w), C3, C4A, C5, C5R1, CANT1, CAPRIN-1, CASP1, CASP4, CAV1, CCBP2 (D6/JAB61), CCL1 (1-309), CCLI1 (eotaxin), CCL13 (MCP-4), CCL15 (MIP-Id), CCL16 (HCC-4), CCL17 (TARC), CCL18 (PARC), CCL19 (MIP-3b), CCL2 (MCP-1), MCAF, CCL20 (MIP-3a), CCL21 (MEP-2), SLC, exodus-2, CCL22 (MDC/STC-I), CCL23 (MPIF-I), CCL24 (MPIF-2/eotaxin-2), CCL25 (TECK), CCL26 (eotaxin-3), CCL27 (CTACK/ILC), CCL28, CCL3 (MIP-Ia), CCL4 (MIPIb), CCL5 (RANTES), CCL7 (MCP-3), CCL8 (mcp-2), CCNA1, CCNA2, CCND1, CCNE1, CCNE2, CCR1 (CKR1/HM145), CCR2 (mcp-IRB/RA), CCR3 (CKR3/CMKBR3), CCR4, CCR5 (CMKBR5/ChemR13), CCR6 (CMKBR6/CKR-L3/STRL22/DRY6), CCR7 (CKR7/EBI1), CCR8 (CMKBR8/TERI/CKR-L1), CCR9 (GPR-9-6), CCRL1 (VSHK1), CCRL2 (L-CCR), CD164, CD19, CDIC, CD2, CD20, CD21, CD200, CD-22, CD24, CD27, CD28, CD3, CD33, CD35, CD37, CD38, CD3E, CD3G, CD3Z, CD4, CD38, CD40, CD40L, CD44, CD45RB, CD47, CD52, CD69, CD72, CD74, CD79A, CD79B, CD8, CD80, CD81, CD83, CD86, CD137, CD152, CD274, CDH1 (Ecadherin), CDH1O, CDH12, CDH13, CDH18, CDH19, CDH2O, CDH5, CDH7, CDH8, CDH9, CDK2, CDK3, CDK4, CDK5, CDK6, CDK7, CDK9, CDKN1A (p21Wap1/Cip1), CDKN1B (p27Kip1), CDKN1C, CDKN2A (p16INK4a), CDKN2B, CDKN2C, CDKN3, CEBPB, CERI, CHGA, CHGB, Chitinase, CHST1O, CKLFSF2, CKLFSF3, CKLFSF4, CKLFSF5, CKLFSF6, CKLFSF7, CKLFSF8, CLDN3, CLDN7 (claudin-7), CLN3, CLU (clusterin), CMKLR1, CMKOR1 (RDC1), CNR1, COL18A1, COLIA1, COL4A3, COL6A1, CR2, Cripto, CRP, CSF1 (M-CSF), CSF2 (GM-CSF), CSF3 (GCSF), CTL8, CTNNB1 (b-catenin), CTSB (cathepsin B), CX3CL1 (SCYD1), CX3CR1 (V28), CXCL1 (GRO1), CXCL1O (IP-IO), CXCLI1 (1-TAC/IP-9), CXCL12 (SDF1), CXCL13, CXCL14, CXCL16, CXCL2 (GRO2), CXCL3 (GRO3), CXCL5 (ENA-78/LIX), CXCL6 (GCP-2), CXCL9 (MIG), CXCR3 (GPR9/CKR-L2), CXCR4, CXCR6 (TYM-STR/STRL33/Bonzo), CYB5, CYC1, CYSLTR1, DAB2IP, DES, DKFZp451J0118, DNCL1, DPP4, E2F1, Engel, Edge, Fennel, EFNA3, EFNB2, EGF, EGFR, ELAC2, ENG, Enola, ENO2, ENO3, EPHA1, EPHA2, EPHA3, EPHA4, EPHA5, EPHA6, EPHA7, EPHA8, EPHA9, EPHA10, EPHB1, EPHB2, EPHB3, EPHB4, EPHB5, EPHB6, EPH-RIN-A1, EPHRIN-A2, EPHRINA3, EPHRIN-A4, EPH-RIN-A5, EPHRIN-A6, EPHRIN-B1, EPHRIN-B2, EPH-RIN-B3, EPHB4, EPG, ERBB2 (Her-2), EREG, ERK8, Estrogen receptor, Earl, ESR2, F3 (TF), FADD, farnesyltransferase, FasL, FASNf, FCER1A, FCER2, FCGR3A, FGF, FGF1 (aFGF), FGF10, FGF11, FGF12, FGF12B, FGF13, FGF14, FGF16, FGF17, FGF18, FGF19, FGF2 (bFGF), FGF20, FGF21, FGF22, FGF23, FGF3 (int-2), FGF4 (HST), FGF5, FGF6 (HST-2), FGF7 (KGF), FGF8, FGF9, FGFR3, FIGF (VEGFD), FIL1 (EPSILON), FBL1 (ZETA), F1112584, F1125530, FLRT1 (fibronectin), FLT1, FLT-3, FOS, FOSL1 (FRA-1), FY (DARC), GABRP (GABAa), GAGEB1, GAGEC1, GALNAC4S-6ST, GATA3, GD2, GDF5, GFI1, GGT1, GM-CSF, GNAS1, GNRH1, GPR2 (CCR10), GPR31, GPR44, GPR81 (FKSG80), GRCC1O (C10), GRP, GSN (Gelsolin), GSTP1, HAVCR2, HDAC, HDAC4, HDAC5, HDAC7A, HDAC9, Hedgehog, HGF, HIF1A, HIP1, histamine and histamine receptors, HLA-A, HLA-DRA, HLA-E, HM74, HMOXI, HSP90, HUMCYT2A, ICEBERG, ICOSL, ID2, IFN-α, IFNA1, IFNA2, IFNA4, IFNA5, EFNA6, BFNA7, IFNB1, IFNgamma, IFNW1, IGBP1, IGF1, IGFIR, IGF2, IGFBP2, IGFBP3, IGFBP6, DL-1, ILIO, ILIORA, ILIORB, IL-1, IL1R1 (CD121a), IL1R2 (CD121b), IL-IRA, IL-2, IL2RA (CD25), IL2RB (CD122), IL2RG (CD132), IL-4, IL-4R (CD123), IL-5, IL5RA (CD125), IL3RB (CD131), IL-6, IL6RA, (CD126), IR6RB (CD130), IL-7, IL7RA (CD127), IL-8, CXCR1 (IL8RA), CXCR2, (IL8RB/CD128), IL-9, IL9R(CD129), IL-10, IL10RA (CD210), ILIORB (CDW210B), IL-11, IL11RA, IL-12, IL-12A, IL-12B, IL-12RB1, IL-12RB2, IL-13, IL13RA1, IL13RA2, IL14, IL15, IL15RA, IL16, IL17, IL17A, IL17B, IL17C, IL17R, IL18, IL18BP, IL18R1, IL18RAP, IL19, ILIA, ILIB, ILIF10, ILIF5, IL1F6, ILIF7, IL1F8, DL1F9, ILIHYI, ILIR1, IL1R2, ILIRAP, ILIRAPLI, ILIRAPL2, ILIRL1, IL1RL2, ILIRN, IL2, IL20, IL20RA, IL21R, IL22, IL22R, IL22RA2, IL23, DL24, IL25, IL26, IL27, IL28A, IL28B, IL29, IL2RA, IL2RB, IL2RG, IL3, IL30, IL3RA, IL4, 1L4, IL6ST (glycoprotein 130), ILK, INHA, INHBA, INSL3, INSL4, IRAK1, IRAK2, ITGA1, ITGA2, ITGA3, ITGA6 (a6 integrin), ITGAV, ITGB3, ITGB4 (f34 integrin), JAG1, JAK1, JAK3, JTB, JUN, K6HF, KAI1, KDR, KITLG, KLF5 (GC Box BP), KLF6, KLK10, KLK12, KLK13, KLK14, KLK15, KLK3, KLK4, KLK5, KLK6, KLK9, KRT1, KRT19 (Keratin 19), KRT2A, KRTHB6 (hair-specific type II keratin), LAMAS, LEP (leptin), Lingo-p75, Lingo-Troy, LPS, LTA (TNF-b), LTB, LTB4R (GPR16), LTB4R2, LTBR, MACMARCKS, MAG or OMgp, MAP2K7 (c-Jun), MCP-1, MDK, MIB1, midkine, MIF, MISRII, MJP-2, MK, MKI67 (Ki-67), MMP2, MMP9, MS4A1, MSMB, MT3 (metallothionectin-UI), mTOR, MTSS1, MUC1 (mucin), MYC, MYD88, NCK2, neurocan, NFKBI, NFKB2, NGFB (NGF), NGFR, NgR-Lingo, NgRNogo66, (Nogo), NgR-p75, NgR-Troy, NMEI (NM23A), NOTCH, NOTCH1, NOX5, NPPB, NROB1, NROB2, NRID1, NR1D2, NR1H2, NR1H3, NR1H4, NR112, NR113, NR2C1, NR2C2, NR2E1, NR2E3, NR2F1, NR2F2, NR2F6, NR3C1, NR3C2, NR4A1, NR4A2, NR4A3, NR5A1, NR5A2, NR6A1, NRP1, NRP2, NT5E, NTN4, ODZI, OPRDI, P2RX7, PAP, PART1, PATE, PAWR, PCA3, PCDGF, PCNA, PDGFA, PDGFB, PDGFRA, PDGFRB, PECAMI, peg-asparaginase, PF4 (CXCL4), PGF, PGR, phosphacan, PIAS2, PI3 Kinase, PIK3CG, PLAU (uPA), PLG, PLXDCI, PKC, PKC-beta, PPBP (CXCL7), PPID, PR1, PRKCQ, PRKD1, PRL, PROC, PROK2, PSAP, PSCA, PTAFR, PTEN, PTGS2 (COX-2), PTN, RAC2 (P21Rac2), RANK, RANK ligand, RARB, RGS1, RGS13, RGS3, RNFI10 (ZNF144), Ron, ROBO2, RXR, S100A2, SCGB 1D2 (lipophilin B), SCGB2A1 (mammaglobin 2), SCGB2A2 (mammaglobin 1), SCYE1 (endothelial Monocyte-activating cytokine), SDF2, SERPENA1, SERPINA3, SERPINB5 (maspin), SERPINEI (PAM), SERPINFI, SHIP-1, SHIP-2, SHB1, SHB2, SHBG, SIRPa (SHPS1), SfcAZ, SLC2A2, SLC33A1, SLC43A1, SLIT2, SPP1, SPRR1B (Spr1), ST6GAL1, STAB1, STATE, STEAP, STEAP2, TB4R2, TBX21, TCP1O, TDGF1, TEK, TGFA, TGFB1, TGFB1I1, TGFB2, TGFB3, TGFBI, TGFBR1, TGFBR2, TGFBR3, THIL, THBS1 (thrombospondin-1), THBS2, THBS4, THPO, TIE (Tie-1), TIMP3, tissue factor, TLR1, TLR2, TLR3, TLR4, TLR5, TLR6, TLR7, TLR8, TLR9, TLR10, TLR11, TNF, TNF-α, TNFAIP2 (B94), TNFAIP3, TNFRSFI1A, TNFRSF1A, TNFRSF1B, TNFRSF21, TNFRSF5, TNFRSF6 (Fas), TNFRSF7, TNFRSF8, TNFRSF9, TNFSF1O (TRAIL), TNFSF11 (TRANCE), TNFSF12 (APO3L), TNFSF13 (April), TNFSF13B, TNFSF14 (HVEM-L), TNFRSF14 (HVEM), TNFSF15 (VEGI), TNFSF18, TNFSF4 (OX40 ligand), TNFSF5 (CD40 ligand), TNFSF6 (FasL), TNFSF7 (CD27 ligand), TNFSF8 (CD30 ligand), TNFSF9 (4-1BB ligand), TOLLIP, Toll-like receptors, TOP2A (topoisomerase Ea), TP53, TPM1, TPM2, TRADD, TRAF1, TRAF2, TRAF3, TRAF4, TRAF5, TRAF6, TRKA, TREM1, TREM2, TRPC6, TSLP, TWEAK, Tyrosinase, uPAR, VEGF, VEGFB, VEGFC, versican, VHL C5, VLA-4, VTCN1 (B7-H4), Wnt-1, XCL1 (lymphotactin), XCL2 (SCM-Ib), XCRI (GPR5/CCXCR1), YY1, ZFPM2, CLEC4C (BDCA-2, DLEC, CD303, CLECSF7), CLEC4D (MCL, CLECSF8), CLEC4E (Mincle), CLEC5A (MDL-1, CLECSF5), CLEC1B (CLEC-2), CLEC9A (DNGR-1), CLEC7A (Dectin-1), PDGFRa, SLAMF7, GP6 (GPVI), LILRA1 (CD85I), LILRA2 (CD85H, ILT1), LILRA4 (CD85G, ILT7), LILRA5 (CD85F, ILT11), LILRA6 (CD85b, ILT8), NCR1 (CD335, LY94, NKp46), NCR3 (CD335, LY94, NKp46), NCR3 (CD337, NKp30), OSCAR, TARM1, CD300C, CD300E, CD300LB (CD300B), CD300LD (CD300D), KIR2DL4 (CD158D), KIR2DS, KLRC2 (CD159C, NKG2C), KLRK1 (CD314, NKG2D), NCR2 (CD336, NKp44), PILRB, SIGLEC1 (CD169, SN), SIGLEC14, SIGLEC15 (CD33L3), SIGLEC16, SIRPB1 (CD172B), TREM1 (CD354), TREM2, TROP2 (tumor-associated calcium signal transducer 2), and KLRF1 (NKp80).

Methods of constructing multivalent binding constructs are known in the art. Bispecific and multispecific antibodies are known in the art. Furthermore, a diabody, triabody, tetrabody, or hexabody can be provided, which is a dimer, trimer, tetramer, or hexamer of polypeptide chains each comprising a $V_H$ connected to a $V_L$ by a peptide linker that is too short to allow pairing between the $V_H$ and $V_L$ on the same polypeptide chain, thereby driving the pairing between the complementary domains on different $V_H$-$V_L$ polypeptide chains to generate a multimeric molecule having two, three, four, or six functional antigen binding sites. Also, bis-scFv fragments, which are small scFv fragments with two different variable domains can be generated to produce bispecific bis-scFv fragments capable of binding two different epitopes. Fab dimers (Fab2) and Fab trimers (Fab3) can be produced using genetic engineering methods to create multispecific constructs based on Fab fragments.

The Dectin-2 binding agent also can be an antibody conjugate. In this respect, the Dectin-2 binding agent can be a conjugate of (1) an antibody, an alternative scaffold, or fragments thereof, and (2) a protein or non-protein moiety. For example, the Dectin-2 binding agent can be conjugated to a peptide, a fluorescent molecule, chemotherapeutic or other cytotoxic payload, immune-activating or immune-suppressive agent.

The Dectin-2 binding agent can be, or can be obtained from, a human antibody, a non-human antibody, a humanized antibody, or a chimeric antibody, or corresponding antibody fragments. A "chimeric" antibody is an antibody or fragment thereof typically comprising human constant regions and non-human variable regions. A "humanized" antibody is a monoclonal antibody typically comprising a human antibody scaffold but with non-human origin amino acids or sequences in at least one CDR (e.g., 1, 2, 3, 4, 5, or all six CDRs).

Methods for generating such antibodies are known in the art and are described in, for example, Köhler and Milstein, *Eur. J. Immunol.*, 5: 511-519 (1976); Harlow and Lane (eds.), *Antibodies: A Laboratory Manual*, CSH Press (1988); and Janeway et al. (eds.), *Immunobiology, 9th Ed.*, Garland Publishing, New York, NY (2017). In certain embodiments, a human or chimeric antibody or antibody fragment can be generated using a transgenic animal (e.g., a mouse) wherein one or more endogenous immunoglobulin genes are replaced with one or more human immunoglobulin genes. Examples of transgenic mice wherein endogenous antibody genes are effectively replaced with human antibody genes include, but are not limited to, the Medarex HUMAB-MOUSE™, the Kirin TC MOUSE™ and the Kyowa Kirin KM-MOUSE™ (see, e.g., Lonberg, *Nat. Biotechnol.*, 23(9): 1117-25 (2005), and Lonberg, *Handb. Exp. Pharmacol.*, 181: 69-97 (2008)). A humanized antibody can be generated using any suitable method known in the art (see, e.g., An, Z. (ed.), *Therapeutic Monoclonal Antibodies: From Bench to Clinic*, John Wiley & Sons, Inc., Hoboken, New Jersey (2009)), including, e.g., grafting of non-human CDRs onto a human antibody scaffold (see, e.g., Kashmiri et al., *Methods*, 36(1): 25-34 (2005); and Hou et al., *J. Biochem.*, 144(1): 115-120 (2008) and use of phage display (see, e.g., Fellouse, et al., *Journal of Molecular Biology*, 373(4): 924-940 (2007) and Glanville, et al., PNAS, 106(48): 20216-20221 (2009)).

In an embodiment, the Dectin-2 binding agent comprises an immunoglobulin heavy chain variable region of any one of SEQ ID NOs: 243-282 or 324, a sequence that is at least about 90%, at least about 91%, at least about 92%, at least about 93%, at least about 94%, at least about 95%, at least about 96%, at least about 97%, at least about 98%, at least about 99%, or 100% identical to SEQ ID NOs: 243-282 or 324, or at least the CDRs thereof; and/or an immunoglobulin light chain variable region of any one of SEQ ID NOs: 283-322, a sequence that is at least about 90%, at least about 91%, at least about 92%, at least about 93%, at least about 94%, at least about 95%, at least about 96%, at least about 97%, at least about 98%, at least about 99%, or 100% identical to SEQ ID NOs: 283-322, or at least the CDRs thereof.

By way of further illustration, the Dectin-2 binding agent can comprise:

(1) an immunoglobulin heavy chain variable region of SEQ ID NO: 243, or at least the CDRs thereof, and/or an immunoglobulin light chain variable region of SEQ ID NO: 283, or at least the CDRs thereof;

(2) an immunoglobulin heavy chain variable region of SEQ ID NO: 244, or at least the CDRs thereof, and/or an immunoglobulin light chain variable region of SEQ ID NO: 284, or at least the CDRs thereof;

(3) an immunoglobulin heavy chain variable region of SEQ ID NO: 245, or at least the CDRs thereof, and/or an immunoglobulin light chain variable region of SEQ ID NO: 285, or at least the CDRs thereof;

(4) an immunoglobulin heavy chain variable region of SEQ ID NO: 246, or at least the CDRs thereof, and/or an immunoglobulin light chain variable region of SEQ ID NO: 286, or at least the CDRs thereof;

(5) an immunoglobulin heavy chain variable region of SEQ ID NO: 247, or at least the CDRs thereof, and/or an immunoglobulin light chain variable region of SEQ ID NO: 287, or at least the CDRs thereof;

(6) an immunoglobulin heavy chain variable region of SEQ ID NO: 248, or at least the CDRs thereof, and/or an immunoglobulin light chain variable region of SEQ ID NO: 288, or at least the CDRs thereof;

(7) an immunoglobulin heavy chain variable region of SEQ ID NO: 249, or at least the CDRs thereof, and/or an immunoglobulin light chain variable region of SEQ ID NO: 289, or at least the CDRs thereof;

(8) an immunoglobulin heavy chain variable region of SEQ ID NO: 250, or at least the CDRs thereof, and/or an immunoglobulin light chain variable region of SEQ ID NO: 290, or at least the CDRs thereof;

(9) an immunoglobulin heavy chain variable region of SEQ ID NO: 251, or at least the CDRs thereof, and/or an immunoglobulin light chain variable region of SEQ ID NO: 291, or at least the CDRs thereof;

(10) an immunoglobulin heavy chain variable region of SEQ ID NO: 252, or at least the CDRs thereof, and/or an immunoglobulin light chain variable region of SEQ ID NO: 292, or at least the CDRs thereof;

(11) an immunoglobulin heavy chain variable region of SEQ ID NO: 253, or at least the CDRs thereof, and/or an immunoglobulin light chain variable region of SEQ ID NO: 293, or at least the CDRs thereof;

(12) an immunoglobulin heavy chain variable region of SEQ ID NO: 254, or at least the CDRs thereof, and/or an immunoglobulin light chain variable region of SEQ ID NO: 294, or at least the CDRs thereof;

(13) an immunoglobulin heavy chain variable region of SEQ ID NO: 255, or at least the CDRs thereof, and/or an immunoglobulin light chain variable region of SEQ ID NO: 295, or at least the CDRs thereof;

(14) an immunoglobulin heavy chain variable region of SEQ ID NO: 256, or at least the CDRs thereof, and/or an immunoglobulin light chain variable region of SEQ ID NO: 296, or at least the CDRs thereof;

(15) an immunoglobulin heavy chain variable region of SEQ ID NO: 257, or at least the CDRs thereof, and/or an immunoglobulin light chain variable region of SEQ ID NO: 297, or at least the CDRs thereof;

(16) an immunoglobulin heavy chain variable region of SEQ ID NO: 258, or at least the CDRs thereof, and/or an immunoglobulin light chain variable region of SEQ ID NO: 298, or at least the CDRs thereof;

(17) an immunoglobulin heavy chain variable region of SEQ ID NO: 259, or at least the CDRs thereof, and/or an immunoglobulin light chain variable region of SEQ ID NO: 299, or at least the CDRs thereof;

(18) an immunoglobulin heavy chain variable region of SEQ ID NO: 256, or at least the CDRs thereof, and/or an immunoglobulin light chain variable region of SEQ ID NO: 300, or at least the CDRs thereof;

(19) an immunoglobulin heavy chain variable region of SEQ ID NO: 260, or at least the CDRs thereof, and/or an immunoglobulin light chain variable region of SEQ ID NO: 301, or at least the CDRs thereof;

(20) an immunoglobulin heavy chain variable region of SEQ ID NO: 261, or at least the CDRs thereof, and/or an immunoglobulin light chain variable region of SEQ ID NO: 302, or at least the CDRs thereof;

(21) an immunoglobulin heavy chain variable region of SEQ ID NO: 262, or at least the CDRs thereof, and/or an immunoglobulin light chain variable region of SEQ ID NO: 303, or at least the CDRs thereof;

(22) an immunoglobulin heavy chain variable region of SEQ ID NO: 263, or at least the CDRs thereof, and/or an immunoglobulin light chain variable region of SEQ ID NO: 304, or at least the CDRs thereof;

(23) an immunoglobulin heavy chain variable region of SEQ ID NO: 264, or at least the CDRs thereof, and/or an immunoglobulin light chain variable region of SEQ ID NO: 305, or at least the CDRs thereof;

(23a) an immunoglobulin heavy chain variable region of SEQ ID NO: 265, or at least the CDRs thereof, and/or an immunoglobulin light chain variable region of SEQ ID NO: 305, or at least the CDRs thereof;

(23b) an immunoglobulin heavy chain variable region of SEQ ID NO: 324, or at least the CDRs thereof, and/or an immunoglobulin light chain variable region of SEQ ID NO: 305, or at least the CDRs thereof;

(24) an immunoglobulin heavy chain variable region of SEQ ID NO: 266, or at least the CDRs thereof, and/or an immunoglobulin light chain variable region of SEQ ID NO: 306, or at least the CDRs thereof;

(25) an immunoglobulin heavy chain variable region of SEQ ID NO: 267, or at least the CDRs thereof, and/or an immunoglobulin light chain variable region of SEQ ID NO: 307, or at least the CDRs thereof;

(26) an immunoglobulin heavy chain variable region of SEQ ID NO: 268, or at least the CDRs thereof, and/or an immunoglobulin light chain variable region of SEQ ID NO: 308, or at least the CDRs thereof;

(27) an immunoglobulin heavy chain variable region of SEQ ID NO: 269, or at least the CDRs thereof, and/or an immunoglobulin light chain variable region of SEQ ID NO: 309, or at least the CDRs thereof;

(28) an immunoglobulin heavy chain variable region of SEQ ID NO: 270, or at least the CDRs thereof, and/or an immunoglobulin light chain variable region of SEQ ID NO: 310, or at least the CDRs thereof;

(29) an immunoglobulin heavy chain variable region of SEQ ID NO: 271, or at least the CDRs thereof, and/or an immunoglobulin light chain variable region of SEQ ID NO: 311, or at least the CDRs thereof;

(30) an immunoglobulin heavy chain variable region of SEQ ID NO: 272, or at least the CDRs thereof, and/or an immunoglobulin light chain variable region of SEQ ID NO: 312, or at least the CDRs thereof;

(31) an immunoglobulin heavy chain variable region of SEQ ID NO: 273, or at least the CDRs thereof, and/or an immunoglobulin light chain variable region of SEQ ID NO: 313, or at least the CDRs thereof;

(32) an immunoglobulin heavy chain variable region of SEQ ID NO: 274, or at least the CDRs thereof, and/or an immunoglobulin light chain variable region of SEQ ID NO: 314, or at least the CDRs thereof;

(33) an immunoglobulin heavy chain variable region of SEQ ID NO: 275, or at least the CDRs thereof, and/or an immunoglobulin light chain variable region of SEQ ID NO: 315, or at least the CDRs thereof;

(34) an immunoglobulin heavy chain variable region of SEQ ID NO: 276, or at least the CDRs thereof, and/or an immunoglobulin light chain variable region of SEQ ID NO: 316, or at least the CDRs thereof;

(35) an immunoglobulin heavy chain variable region of SEQ ID NO: 277, or at least the CDRs thereof, and/or an immunoglobulin light chain variable region of SEQ ID NO: 317, or at least the CDRs thereof;

(36) an immunoglobulin heavy chain variable region of SEQ ID NO: 278, or at least the CDRs thereof, and/or an immunoglobulin light chain variable region of SEQ ID NO: 318, or at least the CDRs thereof;

(37) an immunoglobulin heavy chain variable region of SEQ ID NO: 279, or at least the CDRs thereof, and/or an immunoglobulin light chain variable region of SEQ ID NO: 319, or at least the CDRs thereof;

(38) an immunoglobulin heavy chain variable region of SEQ ID NO: 280, or at least the CDRs thereof, and/or an immunoglobulin light chain variable region of SEQ ID NO: 320, or at least the CDRs thereof;

(39) an immunoglobulin heavy chain variable region of SEQ ID NO: 281, or at least the CDRs thereof, and/or an immunoglobulin light chain variable region of SEQ ID NO: 321, or at least the CDRs thereof;

(40) an immunoglobulin heavy chain variable region of SEQ ID NO: 282, or at least the CDRs thereof, and/or an immunoglobulin light chain variable region of SEQ ID NO: 322, or at least the CDRs thereof;

(41) an immunoglobulin heavy chain variable region of Table 4 and/or an immunoglobulin light chain variable region of Table 5, or at least the CDRs thereof; and/or

(42) an immunoglobulin heavy chain of Table 7 and/or an immunoglobulin light chain of Table 6.

The CDRs of a given heavy or light chain Ig sequence can be determined in accordance with any of the various known Ig numbering schemes, such as Kabat, Chothia, Martin (Enhanced Chothia), IGMT, AbM or AHo (see, e.g., Kabat, et al., *Sequences of Proteins of Immunological Interest*, U.S. Department of Health and Human Services, NIH (1991); Chothia, et al., *Canonical Structures for the Hypervariable Regions of Immunoglobulins*, J. Mol. Biol., 196:901-917 (1987); Al-Lazikani et al., Standard *Conformations for the Canonical Structures of Immunoglobulins*, J. Mol. Biol., 273:927-948 (1997); Abhinandan et al., *Analysis and Improvements to Kabat and Structurally Correct Numbering of Antibody Variable Domains*, Mol. Immunol., 45: 3832-3839 (2008); Lefranc et al., *The IMGT unique numbering for immunoglobulins, T cell Receptors and Ig-like domains*, The Immunologist, 7: 132-136 (1999); Lefranc et al., *IMGT unique numbering for immunoglobulin and T cell receptor variable domains and I superfamily V-like domains*, Dev. Comp. Immunol., 27: 55-77 (2003); and Honegger et al., *Yet another numbering scheme for immunoglobulin variable domains: an automatic modeling and analysis tool*, J. Mol. Biol. 309: 657-670 (2001).). In particular embodiments, Kabat is used to determine the CDRs of a given heavy or light chain Ig sequence. In certain embodiments, the Dectin-2 binding agent comprises one or more of the following CDRs:

a HCDR1 comprising or consisting of any one of SEQ ID NOs: 1-30 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 1-30;

a HCDR2 comprising or consisting of any one of SEQ ID NOs: 31-64 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 31-64; and a HCDR3 comprising or consisting of any one of SEQ ID NOs: 65-103 or 323 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 65-103 or 323; and/or the immunoglobulin light chain polypeptide comprises a LCDR1 comprising or consisting of any one of SEQ ID NOs: 104-125 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 104-125;

a LCDR2 comprising or consisting of any one of SEQ ID NOs: 126-148 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 126-148; and a LCDR3 comprising or consisting of any one of SEQ ID NOs: 149-181 or a sequence that is at least about 90%, at least about 91%, at least about 92%, at least about 93%, at least about 94%, at least about 95%, at least about 96%, at least about 97%, at least about 98%, or at least about 99% identical to SEQ ID NOs: 149-181.

In particular embodiments, the binding agent comprises an immunoglobulin heavy chain polypeptide and an immunoglobulin light chain polypeptide, wherein:

(1) the immunoglobulin heavy chain polypeptide comprises a HCDR1 comprising or consisting of SEQ ID NO: 1, a HCDR2 comprising or consisting of SEQ ID NO: 31, and a HCDR3 comprising or consisting of SEQ ID NO: 65; and/or the immunoglobulin light chain polypeptide comprises a LCDR1 comprising or consisting of SEQ ID NO: 104, a LCDR2 comprising or consisting of SEQ ID NO: 126, and a LCDR3 comprising or consisting of SEQ ID NO: 149;

(2) the immunoglobulin heavy chain polypeptide comprises a HCDR1 comprising or consisting of SEQ ID NO: 2, a HCDR2 comprising or consisting of SEQ ID NO: 32, and a HCDR3 comprising or consisting of SEQ ID NO: 66; and/or the immunoglobulin light chain polypeptide comprises a LCDR1 comprising or consisting of SEQ ID NO: 105, a LCDR2 comprising or consisting of SEQ ID NO: 127, and a LCDR3 comprising or consisting of SEQ ID NO: 150;

(3) the immunoglobulin heavy chain polypeptide comprises a HCDR1 comprising or consisting of SEQ ID NO: 3, a HCDR2 comprising or consisting of SEQ ID NO: 33, and a HCDR3 comprising or consisting of SEQ ID NO: 67; and/or the immunoglobulin light chain polypeptide comprises a LCDR1 comprising or consisting of SEQ ID NO: 106, a LCDR2 comprising or consisting of SEQ ID NO: 126, and a LCDR3 comprising or consisting of SEQ ID NO: 151;

(4) the immunoglobulin heavy chain polypeptide comprises a HCDR1 comprising or consisting of SEQ ID NO: 4, a HCDR2 comprising or consisting of SEQ ID NO: 34, and a HCDR3 comprising or consisting of SEQ ID NO: 68; and/or the immunoglobulin light chain polypeptide comprises a LCDR1 comprising or consisting of SEQ ID NO: 107, a LCDR2 comprising or consisting of SEQ ID NO: 127, and a LCDR3 comprising or consisting of SEQ ID NO: 150;

(5) the immunoglobulin heavy chain polypeptide comprises a HCDR1 comprising or consisting of SEQ ID NO: 5, a HCDR2 comprising or consisting of SEQ ID NO: 35, and a HCDR3 comprising or consisting of SEQ ID NO: 69; and/or the immunoglobulin light chain polypeptide comprises a LCDR1 comprising or consisting of SEQ ID NO: 108, a LCDR2 comprising or consisting of SEQ ID NO: 127, and a LCDR3 comprising or consisting of SEQ ID NO: 152;

(6) the immunoglobulin heavy chain polypeptide comprises a HCDR1 comprising or consisting of SEQ ID NO: 6, a HCDR2 comprising or consisting of SEQ ID NO: 36, and a HCDR3 comprising or consisting of SEQ ID NO: 70; and/or the immunoglobulin light chain polypeptide comprises a LCDR1 comprising or consisting of SEQ ID NO: 104, a LCDR2 comprising or consisting of SEQ ID NO: 128, and a LCDR3 comprising or consisting of SEQ ID NO: 153;

(7) the immunoglobulin heavy chain polypeptide comprises a HCDR1 comprising or consisting of SEQ ID NO: 6, a HCDR2 comprising or consisting of SEQ ID NO: 37, and a HCDR3 comprising or consisting of SEQ ID NO: 71; and/or the immunoglobulin light chain polypeptide comprises a LCDR1 comprising or consisting of SEQ ID NO: 104, a LCDR2 comprising or consisting of SEQ ID NO: 129, and a LCDR3 comprising or consisting of SEQ ID NO: 154;

(8) the immunoglobulin heavy chain polypeptide comprises a HCDR1 comprising or consisting of SEQ ID NO: 7, a HCDR2 comprising or consisting of SEQ ID NO: 38, and a HCDR3 comprising or consisting of SEQ ID NO: 72; and/or the immunoglobulin light chain polypeptide comprises a LCDR1 comprising or consisting of SEQ ID NO: 109, a LCDR2 comprising or consisting of SEQ ID NO: 127, and a LCDR3 comprising or consisting of SEQ ID NO: 155;

(9) the immunoglobulin heavy chain polypeptide comprises a HCDR1 comprising or consisting of SEQ ID NO: 8, a HCDR2 comprising or consisting of SEQ ID NO: 39, and a HCDR3 comprising or consisting of SEQ ID NO: 73; and/or the immunoglobulin light chain polypeptide comprises a LCDR1 comprising or consisting of SEQ ID NO: 110, a LCDR2 comprising or consisting of SEQ ID NO: 126, and a LCDR3 comprising or consisting of SEQ ID NO: 150;

(10) the immunoglobulin heavy chain polypeptide comprises a HCDR1 comprising or consisting of SEQ ID NO: 9, a HCDR2 comprising or consisting of SEQ ID NO: 40, and a HCDR3 comprising or consisting of SEQ ID NO: 74; and/or the immunoglobulin light chain polypeptide comprises a LCDR1 comprising or consisting of SEQ ID NO: 104, a LCDR2 comprising or consisting of SEQ ID NO: 130, and a LCDR3 comprising or consisting of SEQ ID NO: 156;

(11) the immunoglobulin heavy chain polypeptide comprises a HCDR1 comprising or consisting of SEQ ID NO: 10, a HCDR2 comprising or consisting of SEQ ID NO: 41, and a HCDR3 comprising or consisting of SEQ ID NO: 75; and/or the immunoglobulin light chain polypeptide comprises a LCDR1 comprising or consisting of SEQ ID NO: 110, a LCDR2 comprising or consisting of SEQ ID NO: 131, and a LCDR3 comprising or consisting of SEQ ID NO: 157;

(12) the immunoglobulin heavy chain polypeptide comprises a HCDR1 comprising or consisting of SEQ ID NO: 11, a HCDR2 comprising or consisting of SEQ ID NO: 42, and a HCDR3 comprising or consisting of SEQ ID NO: 76; and/or the immunoglobulin light chain polypeptide comprises a LCDR1 comprising or consisting of SEQ ID NO: 111, a LCDR2 comprising or consisting of SEQ ID NO: 132, and a LCDR3 comprising or consisting of SEQ ID NO: 158;

(13) the immunoglobulin heavy chain polypeptide comprises a HCDR1 comprising or consisting of SEQ ID NO: 12, a HCDR2 comprising or consisting of SEQ ID NO: 43, and a HCDR3 comprising or consisting of SEQ ID NO: 77; and/or the immunoglobulin light chain polypeptide comprises a LCDR1 comprising or consisting of SEQ ID NO: 104, a LCDR2 comprising or consisting of SEQ ID NO: 133, and a LCDR3 comprising or consisting of SEQ ID NO: 159;

(14) the immunoglobulin heavy chain polypeptide comprises a HCDR1 comprising or consisting of SEQ ID NO: 13, a HCDR2 comprising or consisting of SEQ ID NO: 44, and a HCDR3 comprising or consisting of SEQ ID NO: 78; and/or the immunoglobulin light chain polypeptide comprises a LCDR1 comprising or consisting of SEQ ID NO: 112, a LCDR2 comprising or consisting of SEQ ID NO: 127, and a LCDR3 comprising or consisting of SEQ ID NO: 160;

(15) the immunoglobulin heavy chain polypeptide comprises a HCDR1 comprising or consisting of SEQ ID NO: 14, a HCDR2 comprising or consisting of SEQ ID NO: 45, and a HCDR3 comprising or consisting of SEQ ID NO: 79; and/or the immunoglobulin light chain polypeptide comprises a LCDR1 comprising or consisting of SEQ ID NO: 113, a LCDR2 comprising or consisting of SEQ ID NO: 134, and a LCDR3 comprising or consisting of SEQ ID NO: 161;

(16) the immunoglobulin heavy chain polypeptide comprises a HCDR1 comprising or consisting of SEQ ID NO: 15, a HCDR2 comprising or consisting of SEQ ID NO: 46, and a HCDR3 comprising or consisting of SEQ ID NO: 80; and/or the immunoglobulin light chain polypeptide comprises a LCDR1 comprising or consisting of SEQ ID NO: 114, a LCDR2 comprising or consisting of SEQ ID NO: 135, and a LCDR3 comprising or consisting of SEQ ID NO: 162;

(17) the immunoglobulin heavy chain polypeptide comprises a HCDR1 comprising or consisting of SEQ ID NO: 16, a HCDR2 comprising or consisting of SEQ ID NO: 47, and a HCDR3 comprising or consisting of SEQ ID NO: 81; and/or the immunoglobulin light chain polypeptide comprises a LCDR1 comprising or consisting of SEQ ID NO: 115, a LCDR2 comprising or consisting of SEQ ID NO: 136, and a LCDR3 comprising or consisting of SEQ ID NO: 163;

(18) the immunoglobulin heavy chain polypeptide comprises a HCDR1 comprising or consisting of SEQ ID NO: 13, a HCDR2 comprising or consisting of SEQ ID NO: 44, and a HCDR3 comprising or consisting of SEQ ID NO: 78; and/or the immunoglobulin light chain polypeptide comprises a LCDR1 comprising or consisting of SEQ ID NO: 112, a LCDR2 comprising or consisting of SEQ ID NO: 127, and a LCDR3 comprising or consisting of SEQ ID NO: 160;

(19) the immunoglobulin heavy chain polypeptide comprises a HCDR1 comprising or consisting of SEQ ID NO: 17, a HCDR2 comprising or consisting of SEQ ID NO: 48, and a HCDR3 comprising or consisting of SEQ ID NO: 82; and/or the immunoglobulin light chain polypeptide comprises a LCDR1 comprising or consisting of SEQ ID NO: 116, a LCDR2 comprising or consisting of SEQ ID NO: 137, and a LCDR3 comprising or consisting of SEQ ID NO: 164;

(20) the immunoglobulin heavy chain polypeptide comprises a HCDR1 comprising or consisting of SEQ ID NO: 18, a HCDR2 comprising or consisting of SEQ ID NO: 49, and a HCDR3 comprising or consisting of SEQ ID NO: 83; and/or the immunoglobulin light chain polypeptide comprises a LCDR1 comprising or consisting of SEQ ID NO: 117, a LCDR2 comprising or consisting of SEQ ID NO: 138, and a LCDR3 comprising or consisting of SEQ ID NO: 150;

(21) the immunoglobulin heavy chain polypeptide comprises a HCDR1 comprising or consisting of SEQ ID NO: 19, a HCDR2 comprising or consisting of SEQ ID NO: 50, and a HCDR3 comprising or consisting of SEQ ID NO: 84; and/or the immunoglobulin light chain polypeptide comprises a LCDR1 comprising or consisting of SEQ ID NO: 118, a LCDR2 comprising or consisting of SEQ ID NO: 139, and a LCDR3 comprising or consisting of SEQ ID NO: 150;

(22) the immunoglobulin heavy chain polypeptide comprises a HCDR1 comprising or consisting of SEQ ID NO: 20, a HCDR2 comprising or consisting of SEQ ID NO: 51, and a HCDR3 comprising or consisting of SEQ ID NO: 85; and/or the immunoglobulin light chain polypeptide comprises a LCDR1 comprising or consisting of SEQ ID NO: 116, a LCDR2 comprising or consisting of SEQ ID NO: 126, and a LCDR3 comprising or consisting of SEQ ID NO: 165;

(23) the immunoglobulin heavy chain polypeptide comprises a HCDR1 comprising or consisting of SEQ ID NO: 21, a HCDR2 comprising or consisting of SEQ ID NO: 52, and a HCDR3 comprising or consisting of SEQ ID NO: 86; and/or the immunoglobulin light chain polypeptide comprises a LCDR1 comprising or consisting of SEQ ID NO: 110, a LCDR2 comprising or consisting of SEQ ID NO: 140, and a LCDR3 comprising or consisting of SEQ ID NO: 166;

(23a) the immunoglobulin heavy chain polypeptide comprises a HCDR1 comprising or consisting of SEQ ID NO: 21, a HCDR2 comprising or consisting of SEQ ID NO: 52, and a HCDR3 comprising or consisting of SEQ ID NO: 86; and/or the immunoglobulin light chain polypeptide comprises a LCDR1 comprising or consisting of SEQ ID NO: 110, a LCDR2 comprising or consisting of SEQ ID NO: 140, and a LCDR3 comprising or consisting of SEQ ID NO: 166;

(23b) immunoglobulin heavy chain polypeptide comprises a HCDR1 comprising or consisting of SEQ ID NO: 21, a HCDR2 comprising or consisting of SEQ ID NO: 52, and a HCDR3 comprising or consisting of SEQ ID NO: 323; and/or the immunoglobulin light chain polypeptide comprises a LCDR1 comprising or consisting of SEQ ID NO: 110, a LCDR2 comprising or consisting of SEQ ID NO: 140, and a LCDR3 comprising or consisting of SEQ ID NO: 166;

(24) the immunoglobulin heavy chain polypeptide comprises a HCDR1 comprising or consisting of SEQ ID NO: 6, a HCDR2 comprising or consisting of SEQ ID NO: 53, and a HCDR3 comprising or consisting of SEQ ID NO: 87; and/or the immunoglobulin light chain polypeptide comprises a LCDR1 comprising or consisting of SEQ ID NO: 104, a LCDR2 comprising or consisting of SEQ ID NO: 141, and a LCDR3 comprising or consisting of SEQ ID NO: 167;

(25) the immunoglobulin heavy chain polypeptide comprises a HCDR1 comprising or consisting of SEQ ID NO: 22, a HCDR2 comprising or consisting of SEQ ID NO: 38, and a HCDR3 comprising or consisting of SEQ ID NO: 88; and/or the immunoglobulin light chain polypeptide comprises a LCDR1 comprising or consisting of SEQ ID NO: 119, a LCDR2 comprising or consisting of SEQ ID NO: 126, and a LCDR3 comprising or consisting of SEQ ID NO: 168;

(26) the immunoglobulin heavy chain polypeptide comprises a HCDR1 comprising or consisting of SEQ ID NO: 6, a HCDR2 comprising or consisting of SEQ ID NO: 37, and a HCDR3 comprising or consisting of SEQ ID NO: 89; and/or the immunoglobulin light chain polypeptide comprises a LCDR1 comprising or consisting of SEQ ID NO: 120, a LCDR2 comprising or consisting of SEQ ID NO: 142, and a LCDR3 comprising or consisting of SEQ ID NO: 169;

(27) the immunoglobulin heavy chain polypeptide comprises a HCDR1 comprising or consisting of SEQ ID NO: 23, a HCDR2 comprising or consisting of SEQ ID NO: 54, and a HCDR3 comprising or consisting of SEQ ID NO: 90; and/or the immunoglobulin light chain polypeptide comprises a LCDR1 comprising or consisting of SEQ ID NO: 121, a LCDR2 comprising or consisting of SEQ ID NO: 143, and a LCDR3 comprising or consisting of SEQ ID NO: 170;

(28) the immunoglobulin heavy chain polypeptide comprises a HCDR1 comprising or consisting of SEQ ID NO: 6, a HCDR2 comprising or consisting of SEQ ID NO: 55, and a HCDR3 comprising or consisting of SEQ ID NO: 91; and/or the immunoglobulin light chain polypeptide comprises a LCDR1 comprising or consisting of SEQ ID NO: 122, a LCDR2 comprising or consisting of SEQ ID NO: 126, and a LCDR3 comprising or consisting of SEQ ID NO: 171;

(29) the immunoglobulin heavy chain polypeptide comprises a HCDR1 comprising or consisting of SEQ ID NO: 19, a HCDR2 comprising or consisting of SEQ ID NO: 56, and a HCDR3 comprising or consisting of SEQ ID NO: 92; and/or the immunoglobulin light chain polypeptide comprises a LCDR1 comprising or consisting of SEQ ID NO: 123, a LCDR2 comprising or consisting of SEQ ID NO: 127, and a LCDR3 comprising or consisting of SEQ ID NO: 172;

(30) the immunoglobulin heavy chain polypeptide comprises a HCDR1 comprising or consisting of SEQ ID NO: 11, a HCDR2 comprising or consisting of SEQ ID NO: 57, and a HCDR3 comprising or consisting of SEQ ID NO: 93; and/or the immunoglobulin light chain polypeptide comprises a LCDR1 comprising or consisting of SEQ ID NO: 109, a LCDR2 comprising or consisting of SEQ ID NO: 144, and a LCDR3 comprising or consisting of SEQ ID NO: 173;

(31) the immunoglobulin heavy chain polypeptide comprises a HCDR1 comprising or consisting of SEQ ID NO: 4, a HCDR2 comprising or consisting of SEQ ID NO: 58, and a HCDR3 comprising or consisting of SEQ ID NO: 94; and/or the immunoglobulin light chain polypeptide comprises a LCDR1 comprising or consisting of SEQ ID NO: 104, a LCDR2 comprising or consisting of SEQ ID NO: 136, and a LCDR3 comprising or consisting of SEQ ID NO: 174;

(32) the immunoglobulin heavy chain polypeptide comprises a HCDR1 comprising or consisting of SEQ ID NO: 24, a HCDR2 comprising or consisting of SEQ ID NO: 59, and a HCDR3 comprising or consisting of SEQ ID NO: 95; and/or the immunoglobulin light chain polypeptide comprises a LCDR1 comprising or consisting of SEQ ID NO: 110, a LCDR2 comprising or consisting of SEQ ID NO: 127, and a LCDR3 comprising or consisting of SEQ ID NO: 153;

(33) the immunoglobulin heavy chain polypeptide comprises a HCDR1 comprising or consisting of SEQ ID NO: 11, a HCDR2 comprising or consisting of SEQ ID NO: 60, and a HCDR3 comprising or consisting of SEQ ID NO: 96; and/or the immunoglobulin light chain polypeptide comprises a LCDR1 comprising or consisting of SEQ ID NO: 111, a LCDR2 comprising or consisting of SEQ ID NO: 145, and a LCDR3 comprising or consisting of SEQ ID NO: 175;

(34) the immunoglobulin heavy chain polypeptide comprises a HCDR1 comprising or consisting of SEQ ID NO: 25, a HCDR2 comprising or consisting of SEQ ID NO: 61, and a HCDR3 comprising or consisting of SEQ ID NO: 97; and/or the immunoglobulin light chain polypeptide comprises a LCDR1 comprising or consisting of SEQ ID NO: 111, a LCDR2 comprising or consisting of SEQ ID NO: 146, and a LCDR3 comprising or consisting of SEQ ID NO: 176;

(35) the immunoglobulin heavy chain polypeptide comprises a HCDR1 comprising or consisting of SEQ ID NO: 26, a HCDR2 comprising or consisting of SEQ ID NO: 59, and a HCDR3 comprising or consisting of SEQ ID NO: 98; and/or the immunoglobulin light chain polypeptide comprises a LCDR1 comprising or consisting of SEQ ID NO: 110, a LCDR2 comprising or consisting of SEQ ID NO: 126, and a LCDR3 comprising or consisting of SEQ ID NO: 177;

(36) the immunoglobulin heavy chain polypeptide comprises a HCDR1 comprising or consisting of SEQ ID NO: 25, a HCDR2 comprising or consisting of SEQ ID NO: 38, and a HCDR3 comprising or consisting of SEQ ID NO: 99; and/or the immunoglobulin light chain polypeptide comprises a LCDR1 comprising or consisting of SEQ ID NO: 124, a LCDR2 comprising or consisting of SEQ ID NO: 126, and a LCDR3 comprising or consisting of SEQ ID NO: 178;

(37) the immunoglobulin heavy chain polypeptide comprises a HCDR1 comprising or consisting of SEQ ID NO: 27, a HCDR2 comprising or consisting of SEQ ID NO: 62, and a HCDR3 comprising or consisting of SEQ ID NO: 100; and/or the immunoglobulin light chain polypeptide comprises a LCDR1 comprising or consisting of SEQ ID NO: 111, a LCDR2 comprising or consisting of SEQ ID NO: 147, and a LCDR3 comprising or consisting of SEQ ID NO: 179;

(38) the immunoglobulin heavy chain polypeptide comprises a HCDR1 comprising or consisting of SEQ ID NO: 28, a HCDR2 comprising or consisting of SEQ ID NO: 63, and a HCDR3 comprising or consisting of SEQ ID NO: 101; and/or the immunoglobulin light chain polypeptide comprises a LCDR1 comprising or consisting of SEQ ID NO: 116, a LCDR2 comprising or consisting of SEQ ID NO: 148, and a LCDR3 comprising or consisting of SEQ ID NO: 180;

(39) the immunoglobulin heavy chain polypeptide comprises a HCDR1 comprising or consisting of SEQ ID NO: 29, a HCDR2 comprising or consisting of SEQ ID NO: 64, and a HCDR3 comprising or consisting of SEQ ID NO: 102; and/or the immunoglobulin light chain polypeptide comprises a LCDR1 comprising or consisting of SEQ ID NO: 121, a LCDR2 comprising or consisting of SEQ ID NO: 126, and a LCDR3 comprising or consisting of SEQ ID NO: 177;

(40) the immunoglobulin heavy chain polypeptide comprises a HCDR1 comprising or consisting of SEQ ID NO: 30, a HCDR2 comprising or consisting of SEQ ID NO: 38, and a HCDR3 comprising or consisting of SEQ ID NO: 103; and/or the immunoglobulin light chain polypeptide comprises a LCDR1 comprising or consisting of SEQ ID NO: 125, a LCDR2 comprising or consisting of SEQ ID NO: 127, and a LCDR3 comprising or consisting of SEQ ID NO: 181;

(41) the immunoglobulin heavy chain polypeptide and immunoglobulin light chain polypeptide comprises any combination of the CDRs listed in Table 1;

(42) the immunoglobulin heavy chain polypeptide comprising or consisting of any one of SEQ ID NOs: 328-345 and immunoglobulin light chain polypeptide comprising or consisting of any one of SEQ ID NOs: 325-327;

(43) the immunoglobulin heavy chain polypeptide comprising or consisting of SEQ ID NO: 328 and immunoglobulin light chain polypeptide comprising or consisting of SEQ ID NO: 325;

(44) the immunoglobulin heavy chain polypeptide comprising or consisting of SEQ ID NO: 329 and immunoglobulin light chain polypeptide comprising or consisting of SEQ ID NO: 325;

(45) the immunoglobulin heavy chain polypeptide comprising or consisting of SEQ ID NO: 330 and light chain polypeptide comprising or consisting of SEQ ID NO: 325;

(46) the immunoglobulin heavy chain polypeptide comprising or consisting of SEQ ID NO: 331 and immunoglobulin light chain polypeptide comprising or consisting of SEQ ID NO: 325;

(47) the immunoglobulin heavy chain polypeptide comprising or consisting of SEQ ID NO: 332 and immunoglobulin light chain polypeptide comprising or consisting of SEQ ID NO: 325;

(48) the immunoglobulin heavy chain polypeptide comprising or consisting of SEQ ID NO: 333 and immunoglobulin light chain polypeptide comprising or consisting of SEQ ID NO: 325;

(49) the immunoglobulin heavy chain polypeptide comprising or consisting of SEQ ID NO: 334 and immunoglobulin light chain polypeptide comprising or consisting of SEQ ID NO: 3;

(50) the immunoglobulin heavy chain polypeptide comprising or consisting of SEQ ID NO: 335 and immunoglobulin light chain polypeptide comprising or consisting of SEQ ID NO: 326;

(51) the immunoglobulin heavy chain polypeptide comprising or consisting of SEQ ID NO: 336 and light chain polypeptide comprising or consisting of SEQ ID NO: 326;

(52) the immunoglobulin heavy chain polypeptide comprising or consisting of SEQ ID NO: 337 and immunoglobulin light chain polypeptide comprising or consisting of SEQ ID NO: 326;
(53) the immunoglobulin heavy chain polypeptide comprising or consisting of SEQ ID NO: 338 and immunoglobulin light chain polypeptide comprising or consisting of SEQ ID NO: 326;
(54) the immunoglobulin heavy chain polypeptide comprising or consisting of SEQ ID NO: 339 and immunoglobulin light chain polypeptide comprising or consisting of SEQ ID NO: 326;
(55) the immunoglobulin heavy chain polypeptide comprising or consisting of SEQ ID NO: 340 and immunoglobulin light chain polypeptide comprising or consisting of SEQ ID NO: 327;
(56) the immunoglobulin heavy chain polypeptide comprising or consisting of SEQ ID NO: 341 and immunoglobulin light chain polypeptide comprising or consisting of SEQ ID NO: 327;
(57) the immunoglobulin heavy chain polypeptide comprising or consisting of SEQ ID NO: 342 and immunoglobulin light chain polypeptide comprising or consisting of SEQ ID NO: 327;
(58) the immunoglobulin heavy chain polypeptide comprising or consisting of SEQ ID NO: 343 and immunoglobulin light chain polypeptide comprising or consisting of SEQ ID NO: 327;
(59) the immunoglobulin heavy chain polypeptide comprising or consisting of SEQ ID NO: 344 and immunoglobulin light chain polypeptide comprising or consisting of SEQ ID NO: 327; and/or
(55) the immunoglobulin heavy chain polypeptide comprising or consisting of SEQ ID NO: 345 and immunoglobulin light chain polypeptide comprising or consisting of SEQ ID NO: 327.

In particular embodiments, the binding agent comprises an immunoglobulin heavy chain polypeptide and an immunoglobulin light chain polypeptide, wherein the immunoglobulin heavy chain polypeptide comprises a first framework region, a second framework region, a third framework region, and/or a fourth framework region; and/or the immunoglobulin light chain polypeptide comprises a first framework region, a second framework region, a third framework region, and/or a fourth framework region; and/or the immunoglobulin heavy chain polypeptide and light chain polypeptide comprises any combination of the framework regions listed in Tables 2 and 3.

TABLE 1

| Binding Agent | SEQ ID | HCDR1 | SEQ ID | HCDR2 | SEQ ID | HCDR3 | SEQ ID | LCDR1 | SEQ ID | LCDR2 | SEQ ID | LCDR3 |
|---|---|---|---|---|---|---|---|---|---|---|---|---|
| 1 | 1 | SYYMQ | 31 | WINPKSGGTN YAQKFQG | 65 | GTYLRTGSSLS GYYYGMDV | 104 | QASQDISNYLN | 126 | AASSLQS | 149 | QQTDSIPIT |
| 2 | 2 | TYYMH | 32 | IINPSGGSTSY AQKFQG | 66 | SHYGDLNGGFD L | 105 | RASQYISSYLA | 127 | AASTLQS | 150 | QQSYSTPLT |
| 3 | 3 | NFGIN | 33 | WINPNSGGAN YAQKFQG | 67 | GVVAARYYYM DV | 106 | RASQNIGSYLN | 126 | AASSLQS | 151 | QQTNSFPLT |
| 4 | 4 | SYDIN | 34 | WINPNSGATN SAQKFQG | 68 | AGYSSSWDGY YYYGMDV | 107 | RASQSISSHLN | 127 | AASTLQS | 150 | QQSYSTPLT |
| 5 | 5 | GYYVH | 35 | IIHPNGGSTSY AQKFQG | 69 | DQAGTGGHGM DV | 108 | RASQSINNWLA | 127 | AASTLQS | 152 | EQNYRLPIT |
| 6 | 6 | SYWMS | 36 | DISGSGRSTYY ADSVKG | 70 | GRYLEWVLSSE DYYFGMDV | 104 | QASQDISNYLN | 128 | AASSLHP | 153 | QQSDSFPLT |
| 7 | 6 | SYWMS | 37 | AISGSGGSTY YADSVKG | 71 | GRYSRSWERW YFDL | 104 | QASQDISNYLN | 129 | AASNLES | 154 | QQTNSFPIT |
| 8 | 7 | SQYMH | 38 | WMNPNSGNT GYAQKFQG | 72 | GQYDSSGYYYF DY | 109 | QASQDIRNYLN | 127 | AASTLQS | 155 | QQSYSFPLT |
| 9 | 8 | TYYMN | 39 | ILSPSGGGTSY APKFQG | 73 | ATYYDFWSGSL DY | 110 | RASQSISSYLN | 126 | AASSLQS | 150 | QQSYSTPLT |
| 10 | 9 | SYFMH | 40 | WMNPNNGNT GYAQKFQG | 74 | QAGYSSGWDY | 104 | QASQDISNYLN | 130 | AAFNLQG | 156 | QQAHSFPLT |
| 11 | 10 | TWYMQ | 41 | WISPYTGNTIY APNVQG | 75 | AVYDILTGAYY FDY | 110 | RASQSISSYLN | 131 | GASTLES | 157 | QQSYSTPIT |
| 12 | 11 | SYAIS | 42 | WISTYNGNTN YAQKFQG | 76 | GRLPPYYYGM DV | 111 | KSSQSVLYSSN NKNYLA | 132 | WASTRES | 158 | QQYYSTPLT |
| 13 | 12 | RYYLH | 43 | RIIPILGIANY AQKFQG | 77 | MATVTKHTYW YFDL | 104 | QASQDISNYLN | 133 | ATSTLQS | 159 | QQANSLPYS |
| 14 | 13 | GQWVH | 44 | LISYDGGSTY YADSVKG | 78 | AGRSTSRYYYY YMDV | 112 | RASENIGNWLA | 127 | AASTLQS | 160 | QQGYSTPYT |
| 15 | 14 | PNYIQ | 45 | IINPSGRSTSY AQKFQG | 79 | SSSGYTTDAFD I | 113 | RASQSVSSNLA | 134 | GASTRAT | 161 | QQYGTSPFT |

TABLE 1-continued

| Binding Agent | SEQ ID | HCDR1 | SEQ ID | HCDR2 | SEQ ID | HCDR3 | SEQ ID | LCDR1 | SEQ ID | LCDR2 | SEQ ID | LCDR3 |
|---|---|---|---|---|---|---|---|---|---|---|---|---|
| 16 | 15 | ASYIH | 46 | GIIPIFGSPNYAQKFQG | 80 | EYQLMNVGMDV | 114 | RASQGISNNLN | 135 | AASILQS | 162 | QQSYTTTLT |
| 17 | 16 | DSHLH | 47 | VIYAGGSRYYADSVKG | 81 | GKQRADAFDI | 115 | RASQSISKFLN | 136 | SASNLQS | 163 | QQANSFPLT |
| 18 | 13 | GQWVH | 44 | LISYDGGSTYYADSVKG | 78 | AGRSTSRYYYYYMDV | 112 | RASENIGNWLA | 127 | AASTLQS | 160 | QQGYSTPYT |
| 19 | 17 | SYWMH | 48 | TISGSGAGTWYADSVKG | 82 | DVDPSRQSYYHGVDV | 116 | RSSQSLLHSNGYNYLD | 137 | LGSNRAS | 164 | MQGAHWPYT |
| 20 | 18 | NYWIQ | 49 | WINPNSGGTRYARNFQG | 83 | GRYYYGSGSQYHAFDI | 117 | RASQSIGSYLN | 138 | AASRLQS | 150 | QQSYSTPLT |
| 21 | 19 | NYYMH | 50 | WLNPNSGTNYAQKFQG | 84 | GRYDSSGYYYFDY | 118 | QASQEIGNYLN | 139 | GASSLQS | 150 | QQSYSTPLT |
| 22 | 20 | GYDMQ | 51 | IINPSGAGTNYAQKFQG | 85 | TVTTPYQYYGMDV | 116 | RSSQSLLHSNGYNYLD | 126 | AASSLQS | 165 | MQALQTPLT |
| 23 | 21 | SYSMN | 52 | VISYDGRIKDYADSVKG | 86 | VRGFSFWFDP | 110 | RASQSISSYLN | 140 | LASSLQS | 166 | QQSYGIPLT |
| 23a | 21 | SYSMN | 52 | VISYDGRIKDYADSVKG | 86 | VRGFSFWFDP | 110 | RASQSISSYLN | 140 | LASSLQS | 166 | QQSYGIPLT |
| 23b | 21 | SYSMN | 52 | VISYDGRIKDYADSVKG | 323 | VRGFSFWFEP | 110 | RASQSISSYLN | 140 | LASSLQS | 166 | QQSYGIPLT |
| 24 | 6 | SYWMS | 53 | GISWNGGKTHYADSVKG | 87 | GGGYFDY | 104 | QASQDISNYLN | 141 | KASSLES | 167 | QQANTFPLT |
| 25 | 22 | GYYIH | 38 | WMNPNSGNTGYAQKFQG | 88 | GRYGSSGWSPGYYYYYMDV | 119 | QASQDITNFLN | 126 | AASSLQS | 168 | QQTYSFPLT |
| 26 | 6 | SYWMS | 37 | AISGSGGSTYYADSVKG | 89 | ARDSGSPKDFDY | 120 | RASQSISTFLN | 142 | AASSLQT | 169 | QQSYSTPP |
| 27 | 23 | SYAMH | 54 | GTSLDGNKNYYADSVKG | 90 | GTMARGS | 121 | QASQDISKYLN | 143 | AASNLQK | 170 | QQANSFPRT |
| 28 | 6 | SYWMS | 55 | TISGSGGTTYYADSVKG | 91 | ATDYPGMDV | 122 | QASQDIGNYLN | 126 | AASSLQS | 171 | LQHNSFPPT |
| 29 | 19 | NYYMH | 56 | WINPHSGGTNYAQKFQG | 92 | GRMHYDSSVHYYYYGMDV | 123 | RASQDIRNYLA | 127 | AASTLQS | 172 | LQAISFPFT |
| 30 | 11 | SYAIS | 57 | LIDPSPGTTYYAQKFQG | 93 | VSIVGATPDYYYGMDV | 109 | QASQDIRNYLN | 144 | DTSNLET | 173 | QQAYSLPWT |
| 31 | 4 | SYDIN | 58 | RINPNSGGTNFAQKFQG | 94 | VIRGGKFDP | 104 | QASQDISNYLN | 136 | SASNLQS | 174 | QQSYTTPYT |
| 32 | 24 | NYGIT | 59 | WMNPNSANTGYAQKFQG | 95 | GLYAAAGDQYYYGMDV | 110 | RASQSISSYLN | 127 | AASTLQS | 153 | QQSDSFPLT |
| 33 | 11 | SYAIS | 60 | VINPSGGGTTYAKKFQG | 96 | GAAFDY | 111 | KSSQSVLYSSNNKNYLA | 145 | WASFRES | 175 | QQYYTTPLT |
| 34 | 25 | GYYMH | 61 | WINPDSGDTNFAQKFQG | 97 | EYGDYGYYYYGMDV | 111 | KSSQSVLYSSNNKNYLA | 146 | WASARES | 176 | QQYKSAPYT |
| 35 | 26 | NYYIH | 59 | WMNPNSANTGYAQKFQG | 98 | GIYYYDSSGGSYYYGMDV | 110 | RASQSISSYLN | 126 | AASSLQS | 177 | QQSNSFPLT |
| 36 | 25 | GYYMH | 38 | WMNPNSGNTGYAQKFQG | 99 | ELSSSWYSYGMDV | 124 | RASQSISRHLN | 126 | AASSLQS | 178 | QQSYQTPLT |
| 37 | 27 | DYGMY | 62 | YISSSGSTIYYADSVKG | 100 | VSGGSWYDRL | 111 | KSSQSVLYSSNNKNYLA | 147 | WASIRES | 179 | QQYYSSPFT |
| 38 | 28 | SYGIN | 63 | RIIPIFGAANYAQKFQG | 101 | TYFDWFFFDY | 116 | RSSQSLLHSNGYNYLD | 148 | DASNLHA | 180 | MQALQAPVT |
| 39 | 29 | SYGIS | 64 | WINPNNGGTNYAQKFQG | 102 | GRYSGHFGVYYYGMDV | 121 | QASQDISKYLN | 126 | AASSLQS | 177 | QQSNSFPLT |

TABLE 1-continued

| Binding Agent | SEQ ID | HCDR1 | SEQ ID | HCDR2 | SEQ ID | HCDR3 | SEQ ID | LCDR1 | SEQ ID | LCDR2 | SEQ ID | LCDR3 |
|---|---|---|---|---|---|---|---|---|---|---|---|---|
| 40 | 30 | SYYMH | 38 | WMNPNSGNTGYAQKFQG | 103 | EPYGDYGFDY | 125 | RASQTVRSYLN | 127 | AASTLQS | 181 | QQTYRTPLT |

TABLE 2

| Binding Agent | SEQ ID | HFW1 | SEQ ID | HFW2 | SEQ ID | HFW3 | SEQ ID | HFW4 |
|---|---|---|---|---|---|---|---|---|
| 1 | 182 | QVQLVQSGAEVKKPGASVKVSCKASGYTFT | 201 | WVRQAPGQGLEWMG | 208 | RVTMTRDTSTSTVYMELSSLRSEDTAVYYCAR | 216 | WGQGTTVTVSS |
| 2 | 183 | QVQLVQSGAEVKKPGASVKVSCKASGYIFT | 201 | WVRQAPGQGLEWMG | 208 | RVTMTRDTSTSTVYMELSSLRSEDTAVYYCAR | 217 | WGRGTLVTVSS |
| 3 | 184 | QVQLVQSGAEVKKPGASVKVSCKASGGTLN | 201 | WVRQAPGQGLEWMG | 208 | RVTMTRDTSTSTVYMELSSLRSEDTAVYYCAR | 218 | WGKGTTVTVSS |
| 4 | 182 | QVQLVQSGAEVKKPGASVKVSCKASGYTFT | 202 | WVRQAPGQGLEWLG | 208 | RVTMTRDTSTSTVYMELSSLRSEDTAVYYCAR | 216 | WGQGTTVTVSS |
| 5 | 182 | QVQLVQSGAEVKKPGASVKVSCKASGYTFT | 201 | WVRQAPGQGLEWMG | 208 | RVTMTRDTSTSTVYMELSSLRSEDTAVYYCAR | 219 | WGQGTMVTVSS |
| 6 | 185 | EVQLLESGGGLVQPGGSLRLSCAASGFTFS | 203 | WVRQAPGKGLEWVS | 209 | RFTISRDNSKNTLYLQMNSLRAEDTAVYYCAR | 216 | WGQGTTVTVSS |
| 7 | 185 | EVQLLESGGGLVQPGGSLRLSCAASGFTFS | 203 | WVRQAPGKGLEWVS | 209 | RFTISRDNSKNTLYLQMNSLRAEDTAVYYCAR | 217 | WGRGTLVTVSS |
| 8 | 182 | QVQLVQSGAEVKKPGASVKVSCKASGYTFT | 201 | WVRQAPGQGLEWMG | 208 | RVTMTRDTSTSTVYMELSSLRSEDTAVYYCAR | 220 | WGQGTLVTVSS |
| 9 | 182 | QVQLVQSGAEVKKPGASVKVSCKASGYTFT | 201 | WVRQAPGQGLEWMG | 208 | RVTMTRDTSTSTVYMELSSLRSEDTAVYYCAR | 220 | WGQGTLVTVSS |
| 10 | 182 | QVQLVQSGAEVKKPGASVKVSCKASGYTFT | 201 | WVRQAPGQGLEWMG | 210 | RVTMTRDTSTSTVYMELSSLRSEDTAVYYCTR | 220 | WGQGTLVTVSS |
| 11 | 186 | QVQLVQSGAEVKKPGASVKVSCKASGYTLT | 201 | WVRQAPGQGLEWMG | 210 | RVTMTRDTSTSTVYMELSSLRSEDTAVYYCTR | 220 | WGQGTLVTVSS |
| 12 | 187 | QVQLVQSGAEVKKPGASVKVSCKASGGTFS | 201 | WVRQAPGQGLEWMG | 208 | RVTMTRDTSTSTVYMELSSLRSEDTAVYYCAR | 216 | WGQGTTVTVSS |
| 13 | 188 | QVQLVQSGVRWRSLGPPVKVSCKASGDTFS | 201 | WVRQAPGQGLEWMG | 211 | RVTITADESTSTAYMELSSLRSEDTAVYYCAR | 217 | WGRGTLVTVSS |
| 14 | 185 | EVQLLESGGGLVQPGGSLRLSCAASGFTFS | 204 | WVRQAPGKGLEWVA | 209 | RFTISRDNSKNTLYLQMNSLRAEDTAVYYCAR | 218 | WGKGTTVTVSS |
| 15 | 183 | QVQLVQSGAEVKKPGASVKVSCKASGYIFT | 201 | WVRQAPGQGLEWMG | 208 | RVTMTRDTSTSTVYMELSSLRSEDTAVYYCAR | 216 | WGQGTTVTVSS |
| 16 | 189 | QVQLVQSGAEVKKPGSSVKVSCKASGYTFT | 201 | WVRQAPGQGLEWMG | 211 | RVTITADESTSTAYMELSSLRSEDTAVYYCAR | 216 | WGQGTTVTVSS |
| 17 | 190 | EVQLLESGGGLVQPGGSLRLSCAASGFIFS | 205 | WVRQAPGKGLEWLS | 209 | RFTISRDNSKNTLYLQMNSLRAEDTAVYYCAR | 220 | WGQGTLVTVSS |
| 18 | 185 | EVQLLESGGGLVQPGGSLRLSCAASGFTFS | 204 | WVRQAPGKGLEWVA | 209 | RFTISRDNSKNTLYLQMNSLRAEDTAVYYCAR | 218 | WGKGTTVTVSS |
| 19 | 191 | EVQLLESGGGLVKPGGSLRLSCAASGFTFS | 203 | WVRQAPGKGLEWVS | 212 | RFTISRDDSKNTLYLQMNSLKTEDTAVYYCAR | 216 | WGQGTTVTVSS |
| 20 | 183 | QVQLVQSGAEVKKPGASVKVSCKASGYIFT | 201 | WVRQAPGQGLEWMG | 208 | RVTMTRDTSTSTVYMELSSLRSEDTAVYYCAR | 219 | WGQGTMVTVSS |
| 21 | 192 | QVQLVQSGAEVKKPGASVKVSCKASEYTFT | 201 | WVRQAPGQGLEWMG | 208 | RVTMTRDTSTSTVYMELSSLRSEDTAVYYCAR | 220 | WGQGTLVTVSS |
| 22 | 193 | QVQLVQSGAEVKKPGSSVKVSCKASGDTFT | 201 | WVRQAPGQGLEWMG | 213 | RVTITADESTSTAYMELSSLRSEDTAVYYCAG | 216 | WGQGTTVTVSS |

TABLE 2-continued

| Binding Agent | SEQ ID | HFW1 | SEQ ID | HFW2 | SEQ ID | HFW3 | SEQ ID | HFW4 |
|---|---|---|---|---|---|---|---|---|
| 23 | 194 | EVQLLESGGGLVQPGGSLRLSCAASTFPFS | 204 | WVRQAPGKGLEWVA | 209 | RFTISRDNSKNTLYLQMNSLRAEDTAVYYCAR | 220 | WGQGTLVTVSS |
| 23a | 185 | EVQLLESGGGLVQPGGSLRLSCAASGFTFS | 204 | WVRQAPGKGLEWVA | 209 | RFTISRDNSKNTLYLQMNSLRAEDTAVYYCAR | 220 | WGQGTLVTVSS |
| 23b | 185 | EVQLLESGGGLVQPGGSLRLSCAASGFTFS | 204 | WVRQAPGKGLEWVA | 209 | RFTISRDNSKNTLYLQMNSLRAEDTAVYYCAR | 220 | WGQGTLVTVSS |
| 24 | 185 | EVQLLESGGGLVQPGGSLRLSCAASGFTFS | 203 | WVRQAPGKGLEWVS | 209 | RFTISRDNSKNTLYLQMNSLRAEDTAVYYCAR | 220 | WGQGTLVTVSS |
| 25 | 195 | QVQLVQSGAEVKKPGASVKVSCKASGYSFT | 201 | WVRQAPGQGLEWMG | 208 | RVTMTRDTSTSTVYMELSSLRSEDTAVYYCAR | 218 | WGKGTTVTVSS |
| 26 | 185 | EVQLLESGGGLVQPGGSLRLSCAASGFTFS | 203 | WVRQAPGKGLEWVS | 209 | RFTISRDNSKNTLYLQMNSLRAEDTAVYYCAR | 220 | WGQGTLVTVSS |
| 27 | 185 | EVQLLESGGGLVQPGGSLRLSCAASGFTFS | 204 | WVRQAPGKGLEWVA | 209 | RFTISRDNSKNTLYLQMNSLRAEDTAVYYCAR | 220 | WGQGTLVTVSS |
| 28 | 185 | EVQLLESGGGLVQPGGSLRLSCAASGFTFS | 203 | WVRQAPGKGLEWVS | 214 | RFTISRDNSKNTLYLQNEQPGAEDTAVYYCAR | 216 | WGQGTTVTVSS |
| 29 | 186 | QVQLVQSGAEVKKPGASVKVSCKASGYTLT | 201 | WVRQAPGQGLEWMG | 210 | RVTMTRDTSTSTVYMELSSLRSEDTAVYYCTR | 220 | WGQGTLVTVSS |
| 30 | 196 | QVQLVQSGAEVKKPGASVKVSCKASGGTGS | 201 | WVRQAPGQGLEWMG | 208 | RVTMTRDTSTSTVYMELSSLRSEDTAVYYCAR | 221 | WGKGTLVTVSS |
| 31 | 182 | QVQLVQSGAEVKKPGASVKVSCKASGYTFT | 201 | WVRQAPGQGLEWMG | 208 | RVTMTRDTSTSTVYMELSSLRSEDTAVYYCAR | 220 | WGQGTLVTVSS |
| 32 | 189 | QVQLVQSGAEVKKPGSSVKVSCKASGYTFT | 206 | WVRQAPGKGLEWMG | 211 | RVTITADESTSTAYMELSSLRSEDTAVYYCAR | 220 | WGQGTLVTVSS |
| 33 | 197 | QVQLVQSGAEVKKPGASVKVSCKASGDTFS | 201 | WVRQAPGQGLEWMG | 208 | RVTMTRDTSTSTVYMELSSLRSEDTAVYYCAR | 220 | WGQGTLVTVSS |
| 34 | 189 | QVQLVQSGAEVKKPGSSVKVSCKASGYTFT | 201 | WVRQAPGQGLEWMG | 211 | RVTITADESTSTAYMELSSLRSEDTAVYYCAR | 219 | WGQGTMVTVSS |
| 35 | 182 | QVQLVQSGAEVKKPGASVKVSCKASGYTFT | 201 | WVRQAPGQGLEWMG | 208 | RVTMTRDTSTSTVYMELSSLRSEDTAVYYCAR | 216 | WGQGTTVTVSS |
| 36 | 182 | QVQLVQSGAEVKKPGASVKVSCKASGYTFT | 201 | WVRQAPGQGLEWMG | 208 | RVTMTRDTSTSTVYMELSSLRSEDTAVYYCAR | 216 | WGQGTTVTVSS |
| 37 | 198 | EVQLLESGGGLVKPGGSLRLSCAASGFTLS | 203 | WVRQAPGKGLEWVS | 212 | RFTISRDDSKNTLYLQMNSLKTEDTAVYYCAR | 222 | LGPGNPVTVSS |
| 38 | 199 | QVQLVQSGAEVKKPGSSVKVSCKASGYTFS | 201 | WVRQAPGQGLEWMG | 215 | RVTITADESTSTAYMELSSLRSEDTAVYYCTR | 220 | WGQGTLVTVSS |
| 39 | 182 | QVQLVQSGAEVKKPGASVKVSCKASGYTFT | 201 | WVRQAPGQGLEWMG | 208 | RVTMTRDTSTSTVYMELSSLRSEDTAVYYCAR | 216 | WGQGTTVTVSS |
| 40 | 200 | QVQLVQSGAEVKKPGASVKVSCKASGYTFS | 207 | WVRQAPGQGLEWMA | 208 | RVTMTRDTSTSTVYMELSSLRSEDTAVYYCAR | 220 | WGQGTLVTVSS |

TABLE 3

| Binding Agent | SEQ ID | LFW1 | SEQ ID | LFW2 | SEQ ID | LFW3 | SEQ ID | LFW4 |
|---|---|---|---|---|---|---|---|---|
| 1 | 223 | DIQMTQSPSSLSASVGDRVTITC | 228 | WYQQKPGKAPKLLIY | 233 | GVPSRFSGSGSGTDFTLTISSLQPEDFATYYC | 237 | FGQGTKVEIK |
| 2 | 223 | DIQMTQSPSSLSASVGDRVTITC | 228 | WYQQKPGKAPKLLIY | 233 | GVPSRFSGSGSGTDFTLTISSLQPEDFATYYC | 238 | FGPGTKVDIK |
| 3 | 223 | DIQMTQSPSSLSASVGDRVTITC | 228 | WYQQKPGKAPKLLIY | 233 | GVPSRFSGSGSGTDFTLTISSLQPEDFATYYC | 239 | FGGGTKVEIK |

TABLE 3-continued

| Binding Agent | SEQ ID | LFW1 | SEQ ID | LFW2 | SEQ ID | LFW3 | SEQ ID | LFW4 |
|---|---|---|---|---|---|---|---|---|
| 4 | 223 | DIQMTQSPSSLSASVGDRVTITC | 228 | WYQQKPGKAPKLLIY | 233 | GVPSRFSGSGSGTDFTLTISSLQPEDFATYYC | 237 | FGQGTKVEIK |
| 5 | 223 | DIQMTQSPSSLSASVGDRVTITC | 228 | WYQQKPGKAPKLLIY | 233 | GVPSRFSGSGSGTDFTLTISSLQPEDFATYYC | 240 | FGQGTRLEIK |
| 6 | 223 | DIQMTQSPSSLSASVGDRVTITC | 228 | WYQQKPGKAPKLLIY | 233 | GVPSRFSGSGSGTDFTLTISSLQPEDFATYYC | 239 | FGGGTKVEIK |
| 7 | 223 | DIQMTQSPSSLSASVGDRVTITC | 228 | WYQQKPGKAPKLLIY | 233 | GVPSRFSGSGSGTDFTLTISSLQPEDFATYYC | 241 | FGQGTKLEIK |
| 8 | 223 | DIQMTQSPSSLSASVGDRVTITC | 228 | WYQQKPGKAPKLLIY | 233 | GVPSRFSGSGSGTDFTLTISSLQPEDFATYYC | 239 | FGGGTKVEIK |
| 9 | 223 | DIQMTQSPSSLSASVGDRVTITC | 228 | WYQQKPGKAPKLLIY | 233 | GVPSRFSGSGSGTDFTLTISSLQPEDFATYYC | 239 | FGGGTKVEIK |
| 10 | 223 | DIQMTQSPSSLSASVGDRVTITC | 228 | WYQQKPGKAPKLLIY | 233 | GVPSRFSGSGSGTDFTLTISSLQPEDFATYYC | 238 | FGPGTKVDIK |
| 11 | 223 | DIQMTQSPSSLSASVGDRVTITC | 228 | WYQQKPGKAPKLLIY | 233 | GVPSRFSGSGSGTDFTLTISSLQPEDFATYYC | 241 | FGQGTKLEIK |
| 12 | 224 | DIVMTQSPDSLAVSLGERATINC | 229 | WYQQKPGQPPKLLIY | 234 | GVPDRFSGSGSGTDFTLTISSLQAEDVAVYYC | 237 | FGQGTKVEIK |
| 13 | 223 | DIQMTQSPSSLSASVGDRVTITC | 228 | WYQQKPGKAPKLLIY | 233 | GVPSRFSGSGSGTDFTLTISSLQPEDFATYYC | 241 | FGQGTKLEIK |
| 14 | 223 | DIQMTQSPSSLSASVGDRVTITC | 228 | WYQQKPGKAPKLLIY | 233 | GVPSRFSGSGSGTDFTLTISSLQPEDFATYYC | 241 | FGQGTKLEIK |
| 15 | 225 | EIVMTQSPATLSVSPGERATLSC | 230 | WYQQKPGQAPRLLIY | 235 | GIPARFSGSGSGTEFTLTISSLQSEDFAVYYC | 240 | FGQGTRLEIK |
| 16 | 223 | DIQMTQSPSSLSASVGDRVTITC | 228 | WYQQKPGKAPKLLIY | 233 | GVPSRFSGSGSGTDFTLTISSLQPEDFATYYC | 238 | FGPGTKVDIK |
| 17 | 223 | DIQMTQSPSSLSASVGDRVTITC | 228 | WYQQKPGKAPKLLIY | 233 | GVPSRFSGSGSGTDFTLTISSLQPEDFATYYC | 237 | FGQGTKVEIK |
| 18 | 223 | DIQMTQSPSSLSASVGDRVTITC | 231 | WYHQKPGKAPKLLIY | 233 | SGVPSRFSGSGSGTDFTLTISSLQPEDFATYYC | 241 | FGQGTKLEIK |
| 19 | 226 | DIVMTQSPLFLPVTGEPASISC | 232 | WYLQKPGQSPQLLIY | 236 | GVPDRFSGSGSGTDFTLKISRVEAEDVGVYYC | 241 | FGQGTKLEIK |
| 20 | 223 | DIQMTQSPSSLSASVGDRVTITC | 228 | WYQQKPGKAPKLLIY | 233 | GVPSRFSGSGSGTDFTLTISSLQPEDFATYYC | 237 | FGQGTKVEIK |
| 21 | 223 | DIQMTQSPSSLSASVGDRVTITC | 228 | WYQQKPGKAPKLLIY | 233 | GVPSRFSGSGSGTDFTLTISSLQPEDFATYYC | 239 | FGGGTKVEIK |
| 22 | 227 | DIVMTQSPLSLPVTGEPASISC | 232 | WYLQKPGQSPQLLIY | 236 | GVPDRFSGSGSGTDFTLKISRVEAEDVGVYYC | 239 | FGGGTKVEIK |
| 23 | 223 | DIQMTQSPSSLSASVGDRVTITC | 228 | WYQQKPGKAPKLLIY | 233 | GVPSRFSGSGSGTDFTLTISSLQPEDFATYYC | 239 | FGGGTKVEIK |
| 23a | 223 | DIQMTQSPSSLSASVGDRVTITC | 228 | WYQQKPGKAPKLLIY | 233 | GVPSRFSGSGSGTDFTLTISSLQPEDFATYYC | 239 | FGGGTKVEIK |
| 23b | 223 | DIQMTQSPSSLSASVGDRVTITC | 228 | WYQQKPGKAPKLLIY | 233 | GVPSRFSGSGSGTDFTLTISSLQPEDFATYYC | 239 | FGGGTKVEIK |
| 24 | 223 | DIQMTQSPSSLSASVGDRVTITC | 228 | WYQQKPGKAPKLLIY | 233 | GVPSRFSGSGSGTDFTLTISSLQPEDFATYYC | 239 | FGGGTKVEIK |
| 25 | 223 | DIQMTQSPSSLSASVGDRVTITC | 228 | WYQQKPGKAPKLLIY | 233 | GVPSRFSGSGSGTDFTLTISSLQPEDFATYYC | 238 | FGPGTKVDIK |
| 26 | 223 | DIQMTQSPSSLSASVGDRVTITC | 228 | WYQQKPGKAPKLLIY | 233 | GVPSRFSGSGSGTDFTLTISSLQPEDFATYYC | 238 | FGPGTKVDIK |

TABLE 3-continued

| Binding Agent | SEQ ID | LFW1 | SEQ ID | LFW2 | SEQ ID | LFW3 | SEQ ID | LFW4 |
|---|---|---|---|---|---|---|---|---|
| 27 | 223 | DIQMTQSPSSLSASVGDRVTITC | 228 | WYQQKPGKAPKLLIY | 233 | GVPSRFSGSGSGTDFTLTISSLQPEDFATYYC | 237 | FGQGTKVEIK |
| 28 | 223 | DIQMTQSPSSLSASVGDRVTITC | 228 | WYQQKPGKAPKLLIY | 233 | GVPSRFSGSGSGTDFTLTISSLQPEDFATYYC | 239 | FGGGTKVEIK |
| 29 | 223 | DIQMTQSPSSLSASVGDRVTITC | 228 | WYQQKPGKAPKLLIY | 233 | GVPSRFSGSGSGTDFTLTISSLQPEDFATYYC | 238 | FGPGTKVDIK |
| 30 | 223 | DIQMTQSPSSLSASVGDRVTITC | 228 | WYQQKPGKAPKLLIY | 233 | GVPSRFSGSGSGTDFTLTISSLQPEDFATYYC | 241 | FGQGTKLEIK |
| 31 | 223 | DIQMTQSPSSLSASVGDRVTITC | 228 | WYQQKPGKAPKLLIY | 233 | GVPSRFSGSGSGTDFTLTISSLQPEDFATYYC | 241 | FGQGTKLEIK |
| 32 | 223 | DIQMTQSPSSLSASVGDRVTITC | 228 | WYQQKPGKAPKLLIY | 233 | GVPSRFSGSGSGTDFTLTISSLQPEDFATYYC | 237 | FGQGTKVEIK |
| 33 | 224 | DIVMTQSPDSLAVSLGERATINC | 229 | WYQQKPGQPPKLLIY | 234 | GVPDRFSGSGSGTDFTLTISSLQAEDVAVYYC | 239 | FGGGTKVEIK |
| 34 | 224 | DIVMTQSPDSLAVSLGERATINC | 229 | WYQQKPGQPPKLLIY | 234 | GVPDRFSGSGSGTDFTLTISSLQAEDVAVYYC | 237 | FGQGTKVEIK |
| 35 | 223 | DIQMTQSPSSLSASVGDRVTITC | 228 | WYQQKPGKAPKLLIY | 233 | GVPSRFSGSGSGTDFTLTISSLQPEDFATYYC | 238 | FGPGTKVDIK |
| 36 | 223 | DIQMTQSPSSLSASVGDRVTITC | 228 | WYQQKPGKAPKLLIY | 233 | GVPSRFSGSGSGTDFTLTISSLQPEDFATYYC | 239 | FGGGTKVEIK |
| 37 | 224 | DIVMTQSPDSLAVSLGERATINC | 229 | WYQQKPGQPPKLLIY | 234 | GVPDRFSGSGSGTDFTLTISSLQAEDVAVYYC | 241 | FGQGTKLEIK |
| 38 | 227 | DIVMTQSPLSLPVTPGEPASISC | 232 | WYLQKPGQSPQLLIY | 236 | GVPDRFSGSGSGTDFTLKISRVEAEDVGVYYC | 240 | FGQGTRLEIK |
| 39 | 223 | DIQMTQSPSSLSASVGDRVTITC | 228 | WYQQKPGKAPKLLIY | 233 | GVPSRFSGSGSGTDFTLTISSLQPEDFATYYC | 242 | FGGGTKLEIK |
| 40 | 223 | DIQMTQSPSSLSASVGDRVTITC | 228 | WYQQKPGKAPKLLIY | 233 | GVPSRFSGSGSGTDFTLTISSLQPEDFATYYC | 237 | FGQGTKVEIK |

TABLE 4

| Binding Agent | SEQ ID | VH |
|---|---|---|
| 1 | 243 | QVQLVQSGAEVKKPGASVKVSCKASGYTFTSYYMQWVRQAPGQGLEWMGWINPKSGGTNYAQKFQGRVTMTRDTSTSTVYMELSSLRSEDTAVYYCARGTYLRTGSSLSGYYYGMDVWGQGTTVTVSS |
| 2 | 244 | QVQLVQSGAEVKKPGASVKVSCKASGYIFTTYYMHWVRQAPGQGLEWMGIINPSGGSTSYAQKFQGRVTMTRDTSTSTVYMELSSLRSEDTAVYYCARSHYGDLNGGFDLWGRGTLVTVSS |
| 3 | 245 | QVQLVQSGAEVKKPGASVKVSCKASGGTLNNFGINWVRQAPGQGLEWMGWINPNSGGANYAQKFQGRVTMTRDTSTSTVYMELSSLRSEDTAVYYCARGVVAARYYYMDVWGKGTTVTVSS |
| 4 | 246 | QVQLVQSGAEVKKPGASVKVSCKASGYTFTSYDINWVRQAPGQGLEWLGWINPNSGATNSAQKFQGRVTMTRDTSTSTVYMELSSLRSEDTAVYYCARAGYSSSWDGYYYYGMDVWGQGTTVTVSS |
| 5 | 247 | QVQLVQSGAEVKKPGASVKVSCKASGYTFTGYYVHWVRQAPGQGLEWMGIIHPNGGSTSYAQKFQGRVTMTRDTSTSTVYMELSSLRSEDTAVYYCARDQAGTGGHGMDVWGQGTMVTVSS |
| 6 | 248 | EVQLLESGGGLVQPGGSLRLSCAASGFTFSSYWMSWVRQAPGKGLEWVSDISGSGRSTYYADSVKGRFTISRDNSKNTLYLQMNSLRAEDTAVYYCARGRYLEWVLSSEDYYFGMDVWGQGTTVTVSS |
| 7 | 249 | EVQLLESGGGLVQPGGSLRLSCAASGFTFSSYWMSWVRQAPGKGLEWVSAISGSGGSTYYADSVKGRFTISRDNSKNTLYLQMNSLRAEDTAVYYCARGRYSRSWERWYFDLWGRGTLVTVSS |
| 8 | 250 | QVQLVQSGAEVKKPGASVKVSCKASGYTFTSQYMHWVRQAPGQGLEWMGWMNPSGNTGYAQKFQGRVTMTRDTSTSTVYMELSSLRSEDTAVYYCARGQYDSSGYYYFDYWGQGTLVTVSS |
| 9 | 251 | QVQLVQSGAEVKKPGASVKVSCKASGYTFTTYYMNWVRQAPGQGLEWMGILSPSGGGTSYAPKFQGRVTMTRDTSTSTVYMELSSLRSEDTAVYYCARATYYDFWSGSLDYWGQGTLVTVSS |

TABLE 4-continued

| Binding Agent | SEQ ID | VH |
|---|---|---|
| 10 | 252 | QVQLVQSGAEVKKPGASVKVSCKASGYTFTSYFMHWVRQAPGQGLEWMGWMNPNNGNTGYAQKFQGRVTMTRDTSTSTVYMELSSLRSEDTAVYYCTRQAGYSSGWDYWGQGTLVTVSS |
| 11 | 253 | QVQLVQSGAEVKKPGASVKVSCKASGYTLTTWYMQWVRQAPGQGLEWMGWISPYTGNTIYAPNVQGRVTMTRDTSTSTVYMELSSLRSEDTAVYYCTRAVYDILTGAYYFDYWGQGTLVTVSS |
| 12 | 254 | QVQLVQSGAEVKKPGASVKVSCKASGGTFSSYAISWVRQAPGQGLEWMGWISTYNGNTNYAQKFQGRVTMTRDTSTSTVYMELSSLRSEDTAVYYCARGRLPPYYYGMDVWGQGTTVTVSS |
| 13 | 255 | QVQLVQSGVRWRSLGPPVKVSCKASGDTFSRYYLHWVRQAPGQGLEWMGRIIPILGIANYAQKFQGRVTITADESTSTAYMELSSLRSEDTAVYYCARMATVTKHTYWYFDLWGRGTLVTVSS |
| 14 | 256 | EVQLLESGGGLVQPGGSLRLSCAASGFTFSGQWVHWVRQAPGKGLEWVALISYDGGSTYYADSVKGRFTISRDNSKNTLYLQMNSLRAEDTAVYYCARAGRSTSRYYYYMDVWGKGTTVTVSS |
| 15 | 257 | QVQLVQSGAEVKKPGASVKVSCKASGYIFTPNYIQWVRQAPGQGLEWMGIINPSGRSTSYAQKFQGRVTMTRDTSTSTVYMELSSLRSEDTAVYYCARSSSGYTTDAFDIWGQGTTVTVSS |
| 16 | 258 | QVQLVQSGAEVKKPGSSVKVSCKASGYTFTASYIHWVRQAPGQGLEWMGGIIPIFGSPNYAQKFQGRVTITADESTSTAYMELSSLRSEDTAVYYCAREYQLMNVGMDVWGQGTTVTVSS |
| 17 | 259 | EVQLLESGGGLVQPGGSLRLSCAASGFIFSDSHLHWVRQAPGKGLEWLSVIYAGGSRYYADSVKGRFTISRDNSKNTLYLQMNSLRAEDTAVYYCARGKQRADAFDIWGQGTLVTVSS |
| 18 | 256 | EVQLLESGGGLVQPGGSLRLSCAASGFTFSGQWVHWVRQAPGKGLEWVALISYDGGSTYYADSVKGRFTISRDNSKNTLYLQMNSLRAEDTAVYYCARAGRSTSRYYYYMDVWGKGTTVTVSS |
| 19 | 260 | EVQLLESGGGLVKPGGSLRLSCAASGFTFSSYWMHWVRQAPGKGLEWVSTISGSGAGTWYADSVKGRFTISRDDSKNTLYLQMNSLKTEDTAVYYCARDVDPSRQSYYHGVDVWGQGTTVTVSS |
| 20 | 261 | QVQLVQSGAEVKKPGASVKVSCKASGYIFTNYWIQWVRQAPGQGLEWMGWINPNSGGTRYARNFQGRVTMTRDTSTSTVYMELSSLRSEDTAVYYCARGRYYYGSGSQYHAFDIWGQGTMVTVSS |
| 21 | 262 | QVQLVQSGAEVKKPGASVKVSCKASEYTFTNYYMHWVRQAPGQGLEWMGWLNPNSGTNYAQKFQGRVTMTRDTSTSTVYMELSSLRSEDTAVYYCARGRYDSSGYYYFDYWGQGTLVTVSS |
| 22 | 263 | QVQLVQSGAEVKKPGSSVKVSCKASGDTFTGYDMQWVRQAPGQGLEWMGIINPSGAGTNYAQKFQGRVTITADESTSTAYMELSSLRSEDTAVYYCAGTVTTPYQYYGMDVWGQGTTVTVSS |
| 23 | 264 | EVQLLESGGGLVQPGGSLRLSCAASTFPFSSYSMNWVRQAPGKGLEWVAVISYDGRIKDYADSVKGRFTISRDNSKNTLYLQMNSLRAEDTAVYYCARVRGFSFWFDPWGQGTLVTVSS |
| 23a | 265 | EVQLLESGGGLVQPGGSLRLSCAASGFTFSSYSMNWVRQAPGKGLEWVAVISYDGRIKDYADSVKGRFTISRDNSKNTLYLQMNSLRAEDTAVYYCARVRGFSFWFDPWGQGTLVTVSS |
| 23b | 324 | EVQLLESGGGLVQPGGSLRLSCAASGFTFSSYSMNWVRQAPGKGLEWVAVISYDGRIKDYADSVKGRFTISRDNSKNTLYLQMNSLRAEDTAVYYCARVRGFSFWFEPWGQGTLVTVSS |
| 24 | 266 | EVQLLESGGGLVQPGGSLRLSCAASGFTFSSYWMSWVRQAPGKGLEWVSGISWNGGKTHYADSVKGRFTISRDNSKNTLYLQMNSLRAEDTAVYYCARGGGYFDYWGQGTLVTVSS |
| 25 | 267 | QVQLVQSGAEVKKPGASVKVSCKASGYSFTGYYIHWVRQAPGQGLEWMGWMNPNSGNTGYAQKFQGRVTMTRDTSTSTVYMELSSLRSEDTAVYYCARGRYGSSGWSPGYYYYYMDVWGKGTTVTVSS |
| 26 | 268 | EVQLLESGGGLVQPGGSLRLSCAASGFTFSSYWMSWVRQAPGKGLEWVSAISGSGGSTYYADSVKGRFTISRDNSKNTLYLQMNSLRAEDTAVYYCARARDSGSPKDFDYWGQGTLVTVSS |
| 27 | 269 | EVQLLESGGGLVQPGGSLRLSCAASGFTFSSYAMHWVRQAPGKGLEWVAGTSLDGNKNYYADSVKGRFTISRDNSKNTLYLQMNSLRAEDTAVYYCARGTMARGSWGQGTLVTVSS |
| 28 | 270 | EVQLLESGGGLVQPGGSLRLSCAASGFTFSSYWMSWVRQAPGKGLEWVSTISGSGGTTYYADSVKGRFTISRDNSKNTLYLQNEQPGAEDTAVYYCARATDYPGMDVWGQGTTVTVSS |
| 29 | 271 | QVQLVQSGAEVKKPGASVKVSCKASGYTLTNYYMHWVRQAPGQGLEWMGWINPHSGGTNYAQKFQGRVTMTRDTSTSTVYMELSSLRSEDTAVYYCTRGRMHYDSSVHYYYYGMDVWGQGTLVTVSS |
| 30 | 272 | QVQLVQSGAEVKKPGASVKVSCKASGGTGSSYAISWVRQAPGQGLEWMGLIDPSPGTTYYAQKFQGRVTMTRDTSTSTVYMELSSLRSEDTAVYYCARVSIVGATPDYYYGMDVWGKGTLVTVSS |
| 31 | 273 | QVQLVQSGAEVKKPGASVKVSCKASGYTFTSYDINWVRQAPGQGLEWMGRINPNSGGTNFAQKFQGRVTMTRDTSTSTVYMELSSLRSEDTAVYYCARVIRGGKFDPWGQGTLVTVSS |
| 32 | 274 | QVQLVQSGAEVKKPGSSVKVSCKASGYTFTNYGITWVRQAPGKGLEWMGWMNPNSANTGYAQKFQGRVTITADESTSTAYMELSSLRSEDTAVYYCARGLYAAAGDQYYYGMDVWGQGTLVTVSS |
| 33 | 275 | QVQLVQSGAEVKKPGASVKVSCKASGDTFSSYAISWVRQAPGQGLEWMGVINPSGGGTTYAKKFQGRVTMTRDTSTSTVYMELSSLRSEDTAVYYCARGAAFDYWGQGTLVTVSS |

TABLE 4-continued

| Binding Agent | SEQ ID | VH |
|---|---|---|
| 34 | 276 | QVQLVQSGAEVKKPGSSVKVSCKASGYTFTGYYMHWVRQAPGQGLEWMGWINPDSGDTNFAQKFQGRVTITADESTSTAYMELSSLRSEDTAVYYCAREYGDYGYYYYGMDVWGQGTMVTVSS |
| 35 | 277 | QVQLVQSGAEVKKPGASVKVSCKASGYTFTNYYIHWVRQAPGQGLEWMGWMNPNSANTGYAQKFQGRVTMTRDTSTSTVYMELSSLRSEDTAVYYCARGIYYYDSSGGSYYYGMDVWGQGTTVTVSS |
| 36 | 278 | QVQLVQSGAEVKKPGASVKVSCKASGYTFTGYYMHWVRQAPGQGLEWMGWMNPNSGNTGYAQKFQGRVTMTRDTSTSTVYMELSSLRSEDTAVYYCARELSSSWYSYGMDVWGQGTTVTVSS |
| 37 | 279 | EVQLLESGGGLVKPGGSLRLSCAASGFTLSDYGMYWVRQAPGKGLEWVSYISSSGSTIYYADSVKGRFTISRDDSKNTLYLQMNSLKTEDTAVYYCARVSGGSWYDRLLGPGNPVTVSS |
| 38 | 280 | QVQLVQSGAEVKKPGSSVKVSCKASGYTFSSYGINWVRQAPGQGLEWMGRIIPIFGAANYAQKFQGRVTITADESTSTAYMELSSLRSEDTAVYYCTRTYFDWFFFDYWGQGTLVTVSS |
| 39 | 281 | QVQLVQSGAEVKKPGASVKVSCKASGYTFTSYGISWVRQAPGQGLEWMGWINPNNGGTNYAQKFQGRVTMTRDTSTSTVYMELSSLRSEDTAVYYCARGRYSGHFGVYYYGMDVWGQGTTVTVSS |
| 40 | 282 | QVQLVQSGAEVKKPGASVKVSCKASGYTFSSYYMHWVRQAPGQGLEWMAWMNPNSGNTGYAQKFQGRVTMTRDTSTSTVYMELSSLRSEDTAVYYCAREPYGDYGFDYWGQGTLVTVSS |

TABLE 5

| Binding Agent | SEQ ID | VL |
|---|---|---|
| 1 | 283 | DIQMTQSPSSLSASVGDRVTITCQASQDISNYLNWYQQKPGKAPKLLIYAASSLQSGVPSRFSGSGSGTDFTLTISSLQPEDFATYYCQQTDSIPITFGQGTKVEIK |
| 2 | 284 | DIQMTQSPSSLSASVGDRVTITCRASQYISSYLAWYQQKPGKAPKLLIYAASTLQSGVPSRFSGSGSGTDFTLTISSLQPEDFATYYCQQSYSTPLTFGPGTKVDIK |
| 3 | 285 | DIQMTQSPSSLSASVGDRVTITCRASQNIGSYLNWYQQKPGKAPKLLIYAASSLQSGVPSRFSGSGSGTDFTLTISSLQPEDFATYYCQQTNSFPLTFGGGTKVEIK |
| 4 | 286 | DIQMTQSPSSLSASVGDRVTITCRASQSISSHLNWYQQKPGKAPKLLIYAASTLQSGVPSRFSGSGSGTDFTLTISSLQPEDFATYYCQQSYSTPLTFGQGTKVEIK |
| 5 | 287 | DIQMTQSPSSLSASVGDRVTITCRASQSINNWLAWYQQKPGKAPKLLIYAASTLQSGVPSRFSGSGSGTDFTLTISSLQPEDFATYYCEQNYRLPITFGQGTRLEIK |
| 6 | 288 | DIQMTQSPSSLSASVGDRVTITCQASQDISNYLNWYQQKPGKAPKLLIYAASSLHPGVPSRFSGSGSGTDFTLTISSLQPEDFATYYCQQSDSFPLTFGGGTKVEIK |
| 7 | 289 | DIQMTQSPSSLSASVGDRVTITCQASQDISNYLNWYQQKPGKAPKLLIYAASNLESGVPSRFSGSGSGTDFTLTISSLQPEDFATYYCQQTNSFPITFGQGTKLEIK |
| 8 | 290 | DIQMTQSPSSLSASVGDRVTITCQASQDIRNYLNWYQQKPGKAPKLLIYAASTLQSGVPSRFSGSGSGTDFTLTISSLQPEDFATYYCQQSYSFPLTFGGGTKVEIK |
| 9 | 291 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTKVEIK |
| 10 | 292 | DIQMTQSPSSLSASVGDRVTITCQASQDISNYLNWYQQKPGKAPKLLIYAAFNLQGGVPSRFSGSGSGTDFTLTISSLQPEDFATYYCQQAHSFPLTFGPGTKVDIK |
| 11 | 293 | DIQMTQSPSSLSASVGDRVTITCRASQSISSYLNWYQQKPGKAPKLLIYGASTLESGVPSRFSGSGSGTDFTLTISSLQPEDFATYYCQQSYSTPITFGQGTKLEIK |
| 12 | 294 | DIVMTQSPDSLAVSLGERATINCKSSQSVLYSSNNKNYLAWYQQKPGQPPKLLIYWASTRESGVPDRFSGSGSGTDFTLTISSLQAEDVAVYYCQQYYSTPLTFGQGTKVEIK |
| 13 | 295 | DIQMTQSPSSLSASVGDRVTITCQASQDISNYLNWYQQKPGKAPKLLIYATSTLQSGVPSRFSGSGSGTDFTLTISSLQPEDFATYYCQQANSLPYSFGQGTKLEIK |
| 14 | 296 | DIQMTQSPSSLSASVGDRVTITCRASENIGNWLAWYQQKPGKAPKLLIYAASTLQSGVPSRFSGSGSGTDFTLTISSLQPEDFATYYCQQGYSTPYTFGQGTKLEIK |
| 15 | 297 | EIVMTQSPATLSVSPGERATLSCRASQSVSSNLAWYQQKPGQAPRLLIYGASTRATGIPARFSGSGSGTEFTLTISSLQSEDFAVYYCQQYGTSPFTFGQGTRLEIK |
| 16 | 298 | DIQMTQSPSSLSASVGDRVTITCRASQGISNNLNWYQQKPGKAPKLLIYAASILQSGVPSRFSGSGSGTDFTLTISSLQPEDFATYYCQQSYTTLTFGPGTKVDIK |

TABLE 5-continued

| Binding Agent | SEQ ID | VL |
|---|---|---|
| 17 | 299 | DIQMTQSPSSLSASVGDRVTITCRASQSISKFLNWYQQKPGKAPKLLIYSASNLQSGVPSRFSGSGSGTDFTLTISSLQPEDFATYYCQQANSFPLTFGQGTKVEIK |
| 18 | 300 | DIQMTQSPSSLSASVGDRVTITCRASENIGNWLAWYHQKPGKAPKLLIYAASTLQSGVPSRFSGSGSGTDFTLTISSLQPEDFATYYCQQGYSTPYTFGQGTKLEIK |
| 19 | 301 | DIVMTQSPLFLPVTPGEPASISCRSSQSLLHSNGYNYLDWYLQKPGQSPQLLIYLGSNRASGVPDRFSGSGSGTDFTLKISRVEAEDVGVYYCMQGAHWPYTFGQGTKLEIK |
| 20 | 302 | DIQMTQSPSSLSASVGDRVTITCRASQSIGSYLNWYQQKPGKAPKLLIYAASRLQSGVPSRFSGSGSGTDFTLTISSLQPEDFATYYCQQSYSTPLTFGQGTKVEIK |
| 21 | 303 | DIQMTQSPSSLSASVGDRVTITCQASQEIGNYLNWYQQKPGKAPKLLIYGASSLQSGVPSRFSGSGSGTDFTLTISSLQPEDFATYYCQQSYSTPLTFGGGTKVEIK |
| 22 | 304 | DIVMTQSPLSLPVTPGEPASISCRSSQSLLHSNGYNYLDWYLQKPGQSPQLLIYAASSLQSGVPDRFSGSGSGTDFTLKISRVEAEDVGVYYCMQALQTPLTFGGGTKVEIK |
| 23 | 305 | DIQMTQSPSSLSASVGDRVTITCRASQSISSYLNWYQQKPGKAPKLLIYLASSLQSGVPSRFSGSGSGTDFTLTISSLQPEDFATYYCQQSYGIPLTFGGGTKVEIK |
| 23a | 305 | DIQMTQSPSSLSASVGDRVTITCRASQSISSYLNWYQQKPGKAPKLLIYLASSLQSGVPSRFSGSGSGTDFTLTISSLQPEDFATYYCQQSYGIPLTFGGGTKVEIK |
| 23b | 305 | DIQMTQSPSSLSASVGDRVTITCRASQSISSYLNWYQQKPGKAPKLLIYLASSLQSGVPSRFSGSGSGTDFTLTISSLQPEDFATYYCQQSYGIPLTFGGGTKVEIK |
| 24 | 306 | DIQMTQSPSSLSASVGDRVTITCQASQDISNYLNWYQQKPGKAPKLLIYKASSLESGVPSRFSGSGSGTDFTLTISSLQPEDFATYYCQQANTFPLTFGGGTKVEIK |
| 25 | 307 | DIQMTQSPSSLSASVGDRVTITCQASQDITNFLNWYQQKPGKAPKLLIYAASSLQSGVPSRFSGSGSGTDFTLTISSLQPEDFATYYCQQTYSFPLTFGPGTKVDIK |
| 26 | 308 | DIQMTQSPSSLSASVGDRVTITCRASQSISTFLNWYQQKPGKAPKLLIYAASSLQTGVPSRFSGSGSGTDFTLTISSLQPEDFATYYCQQSYSTPPFGPGTKVDIK |
| 27 | 309 | DIQMTQSPSSLSASVGDRVTITCQASQDISKYLNWYQQKPGKAPKLLIYAASNLQKGVPSRFSGSGSGTDFTLTISSLQPEDFATYYCQQANSFPRTFGQGTKVEIK |
| 28 | 310 | DIQMTQSPSSLSASVGDRVTITCQASQDIGNYLNWYQQKPGKAPKLLIYAASSLQSGVPSRFSGSGSGTDFTLTISSLQPEDFATYYCLQHNSFPPTFGGGTKVEIK |
| 29 | 311 | DIQMTQSPSSLSASVGDRVTITCRASQDIRNYLAWYQQKPGKAPKLLIYAASTLQSGVPSRFSGSGSGTDFTLTISSLQPEDFATYYCLQAISFPFTFGPGTKVDIK |
| 30 | 312 | DIQMTQSPSSLSASVGDRVTITCQASQDIRNYLNWYQQKPGKAPKLLIYDTSNLETGVPSRFSGSGSGTDFTLTISSLQPEDFATYYCQQAYSLPWTFGQGTKLEIK |
| 31 | 313 | DIQMTQSPSSLSASVGDRVTITCQASQDISNYLNWYQQKPGKAPKLLIYSASNLQSGVPSRFSGSGSGTDFTLTISSLQPEDFATYYCQQSYTTPYTFGQGTKLEIK |
| 32 | 314 | DIQMTQSPSSLSASVGDRVTITCRASQSISSYLNWYQQKPGKAPKLLIYAASTLQSGVPSRFSGSGSGTDFTLTISSLQPEDFATYYCQQSDSFPLTFGQGTKVEIK |
| 33 | 315 | DIVMTQSPDSLAVSLGERATINCKSSQSVLYSSNNKNYLAWYQQKPGQPPKLLIYWASFRESGVPDRFSGSGSGTDFTLTISSLQAEDVAVYYCQQYYTTPLTFGGGTKVEIK |
| 34 | 316 | DIVMTQSPDSLAVSLGERATINCKSSQSVLYSSNNKNYLAWYQQKPGQPPKLLIYWASARESGVPDRFSGSGSGTDFTLTISSLQAEDVAVYYCQQYKSAPYTFGQGTKVEIK |
| 35 | 317 | DIQMTQSPSSLSASVGDRVTITCRASQSISSYLNWYQQKPGKAPKLLIYAASSLQSGVPSRFSGSGSGTDFTLTISSLQPEDFATYYCQQSNSFPLTFGPGTKVDIK |
| 36 | 318 | DIQMTQSPSSLSASVGDRVTITCRASQSISRHLNWYQQKPGKAPKLLIYAASSLQSGVPSRFSGSGSGTDFTLTISSLQPEDFATYYCQQSYQTPLTFGGGTKVEIK |
| 37 | 319 | DIVMTQSPDSLAVSLGERATINCKSSQSVLYSSNNKNYLAWYQQKPGQPPKLLIYWASIRESGVPDRFSGSGSGTDFTLTISSLQAEDVAVYYCQQYYSSPFTFGQGTKLEIK |
| 38 | 320 | DIVMTQSPLSLPVTPGEPASISCRSSQSLLHSNGYNYLDWYLQKPGQSPQLLIYDASNLHAGVPDRFSGSGSGTDFTLKISRVEAEDVGVYYCMQALQAPVTFGQGTRLEIK |
| 39 | 321 | DIQMTQSPSSLSASVGDRVTITCQASQDISKYLNWYQQKPGKAPKLLIYAASSLQSGVPSRFSGSGSGTDFTLTISSLQPEDFATYYCQQSNSFPLTFGGGTKLEIK |

TABLE 5-continued

| Binding Agent | SEQ ID | VL |
|---|---|---|
| 40 | 322 | DIQMTQSPSSLSASVGDRVTITCRASQTVRSYLNWYQQKPGKAPKLLIYAASTLQSGVPSRFSGSGSGTDFTLTISSLQPEDFATYYCQQTYRTPLTFGQGTKVEIK |

TABLE 6

| Binding Agent | SEQ ID | Light Chain Sequence |
|---|---|---|
| 1 | 325 | DIQMTQSPSSLSASVGDRVTITCQASQDISNYLNWYQQKPGKAPKLLIYAASSLQSGVPSRFSGSGSGTDFTLTISSLQPEDFATYYCQQTDSIPITFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 20 | 326 | DIQMTQSPSSLSASVGDRVTITCRASQSIGSYLNWYQQKPGKAPKLLIYAASRLQSGVPSRFSGSGSGTDFTLTISSLQPEDFATYYCQQSYSTPLTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 23a & 23b | 327 | DIQMTQSPSSLSASVGDRVTITCRASQSISSYLNWYQQKPGKAPKLLIYLASSLQSGVPSRFSGSGSGTDFTLTISSLQPEDFATYYCQQSYGIPLTFGGGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |

TABLE 7

| Binding Agent | SEQ ID | Fc mod. | Heavy Chain Sequence |
|---|---|---|---|
| 1 | 328 | (none) | QVQLVQSGAEVKKPGASVKVSCKASGYTFTSYYMQWVRQAPGQGLEWMGWINPKSGGTNYAQKFQGRVTMTRDTSTSTVYMELSSLRSEDTAVYYCARGTYLRTGSSLSGYYYGMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 1 | 329 | SE | QVQLVQSGAEVKKPGASVKVSCKASGYTFTSYYMQWVRQAPGQGLEWMGWINPKSGGTNYAQKFQGRVTMTRDTSTSTVYMELSSLRSEDTAVYYCARGTYLRTGSSLSGYYYGMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVEHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 1 | 330 | ER | QVQLVQSGAEVKKPGASVKVSCKASGYTFTSYYMQWVRQAPGQGLEWMGWINPKSGGTNYAQKFQGRVTMTRDTSTSTVYMELSSLRSEDTAVYYCARGTYLRTGSSLSGYYYGMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPRRPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 1 | 331 | SEER | QVQLVQSGAEVKKPGASVKVSCKASGYTFTSYYMQWVRQAPGQGLEWMGWINPKSGGTNYAQKFQGRVTMTRDTSTSTVYMELSSLRSEDTAVYYCARGTYLRTGSSLSGYYYGMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVEHEDPEVKFNWYVDGVEVHNAKTKPREEQYNSTYRVVSVLTVLHQDWLNGKEYKCKVSNKALPAPIEKTISKAKGQPRRPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK |
| 1 | 332 | NA | QVQLVQSGAEVKKPGASVKVSCKASGYTFTSYYMQWVRQAPGQGLEWMGWINPKSGGTNYAQKFQGRVTMTRDTSTSTVYMELSSLRSEDTAVYYCARGTYLRTGSSLSGYYYGMDVWGQGTTVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYASTYRVVSVLTVLHQDWLNGKEYKCKVSNKALPAPIEKTISKAKGQPREPQVYTLPPSREEMTKNQVSLTC |

TABLE 7-continued

| Binding Agent | SEQ ID | Fc mod. | Heavy Chain Sequence |
|---|---|---|---|
| | | | LVKGFYPSDIAVEWESNGQPENNYKTTPPVLDSDGSFFLYSKLTVDKSRWQQGN VFSCSVMHEALHNHYTQKSLSLSPGK |
| 1 | 333 | GA | QVQLVQSGAEVKKPGASVKVSCKASGYTFTSYYMQWVRQAPGQGLEWMGWINPK SGGTNYAQKFQGRVTMTRDTSTSTVYMELSSLRSEDTAVYYCARGTYLRTGSSL SGYYYGMDVWGQGTTVTVSSASTKGPSVFPLAPSSKSTSGGTAALGCLVKDYFP EPVTVSWNSGALTSGVHTFPAVLQSSGLYSLSSVVTVPSSSLGTQTYICNVNHK PSNTKVDKRVEPKSCDKTHTCPPCPAPELLAGPSVFLFPPKPKDTLMISRTPEV TCVVVDVSHEDPEVKFNWYVDGVEVHNAKTKPREEQYNSTYRVVSVLTVLHQDW LNGKEYKCKVSNKALPAPIEKTISKAKGQPREPQVYTLPPSREEMTKNQVSLTC LVKGFYPSDIAVEWESNGQPENNYKTTPPVLDSDGSFFLYSKLTVDKSRWQQGN VFSCSVMHEALHNHYTQKSLSLSPGK |
| 20 | 334 | (none) | QVQLVQSGAEVKKPGASVKVSCKASGYIFTNYWIQWVRQAPGQGLEWMGWINPN SGGTRYARNFQGRVTMTRDTSTSTVYMELSSLRSEDTAVYYCARGRYYYGSGSQ YHAFDIWGQGTMVTVSSASTKGPSVFPLAPSSKSTSGGTAALGCLVKDYFPEPV TVSWNSGALTSGVHTFPAVLQSSGLYSLSSVVTVPSSSLGTQTYICNVNHKPSN TKVDKRVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTVLHQDWLNG KEYKCKVSNKALPAPIEKTISKAKGQPREPQVYTLPPSREEMTKNQVSLTCLVK GFYPSDIAVEWESNGQPENNYKTTPPVLDSDGSFFLYSKLTVDKSRWQQGNVFS CSVMHEALHNHYTQKSLSLSPGK |
| 20 | 335 | GA | QVQLVQSGAEVKKPGASVKVSCKASGYIFTNYWIQWVRQAPGQGLEWMGWINPN SGGTRYARNFQGRVTMTRDTSTSTVYMELSSLRSEDTAVYYCARGRYYYGSGSQ YHAFDIWGQGTMVTVSSASTKGPSVFPLAPSSKSTSGGTAALGCLVKDYFPEPV TVSWNSGALTSGVHTFPAVLQSSGLYSLSSVVTVPSSSLGTQTYICNVNHKPSN TKVDKRVEPKSCDKTHTCPPCPAPELLAGPSVFLFPPKPKDTLMISRTPEVTCV VVDVSHEDPEVKFNWYVDGVEVHNAKTKPREEQYNSTYRVVSVLTVLHQDWLNG KEYKCKVSNKALPAPIEKTISKAKGQPREPQVYTLPPSREEMTKNQVSLTCLVK GFYPSDIAVEWESNGQPENNYKTTPPVLDSDGSFFLYSKLTVDKSRWQQGNVFS CSVMHEALHNHYTQKSLSLSPGK |
| 20 | 336 | LALA | QVQLVQSGAEVKKPGASVKVSCKASGYIFTNYWIQWVRQAPGQGLEWMGWINPN SGGTRYARNFQGRVTMTRDTSTSTVYMELSSLRSEDTAVYYCARGRYYYGSGSQ YHAFDIWGQGTMVTVSSASTKGPSVFPLAPSSKSTSGGTAALGCLVKDYFPEPV TVSWNSGALTSGVHTFPAVLQSSGLYSLSSVVTVPSSSLGTQTYICNVNHKPSN TKVDKRVEPKSCDKTHTCPPCPAPEAAGGPSVFLFPPKPKDTLMISRTPEVTCV VVDVSHEDPEVKFNWYVDGVEVHNAKTKPREEQYNSTYRVVSVLTVLHQDWLNG KEYKCKVSNKALPAPIEKTISKAKGQPREPQVYTLPPSREEMTKNQVSLTCLVK GFYPSDIAVEWESNGQPENNYKTTPPVLDSDGSFFLYSKLTVDKSRWQQGNVFS CSVMHEALHNHYTQKSLSLSPGK |
| 20 | 337 | NA | QVQLVQSGAEVKKPGASVKVSCKASGYIFTNYWIQWVRQAPGQGLEWMGWINPN SGGTRYARNFQGRVTMTRDTSTSTVYMELSSLRSEDTAVYYCARGRYYYGSGSQ AYHFDIWGQGTMVTVSSASTKGPSVFPLAPSSKSTSGGTAALGCLVKDYFPEPV TVSWNSGALTSGVHTFPAVLQSSGLYSLSSVVTVPSSSLGTQTYICNVNHKPSN TKVDKRVEPKSCDKTHTCPPCPAPELLGGPSVFLFPPKPKDTLMISRTPEVTCV VVDVSHEDPEVKFNWYVDGVEVHNAKTKPREEQYASTYRVVSVLTVLHQDWLNG KEYKCKVSNKALPAPIEKTISKAKGQPREPQVYTLPPSREEMTKNQVSLTCLVK GFYPSDIAVEWESNGQPENNYKTTPPVLDSDGSFFLYSKLTVDKSRWQQGNVFS CSVMHEALHNHYTQKSLSLSPGK |
| 20 | 338 | CS (IgG2) | QVQLVQSGAEVKKPGASVKVSCKASGYIFTNYWIQWVRQAPGQGLEWMGWINPN SGGTRYARNFQGRVTMTRDTSTSTVYMELSSLRSEDTAVYYCARGRYYYGSGSQ YHAFDIWGQGTMVTVSSASTKGPSVFPLAPCSRSTSESTAALGCLVKDYFPEPV TVSWNSGALTSGVHTFPAVLQSSGLYSLSSVVTVPSSNFGTQTYTCNVDHKPSN TKVDKTVERKSCVECPPCPAPPVAGPSVFLFPPKPKDTLMISRTPEVTCVVVDV SHEDPEVQFNWYVDGVEVHNAKTKPREEQFNSTFRVVSVLTVVHQDWLNGKEYK CKVSNKGLPAPIEKTISKTKGQPREPQVYTLPPSREEMTKNQVSLTCLVKGFYP SDIAVEWESNGQPENNYKTTPPMLDSDGSFFLYSKLTVDKSRWQQGNVFSCSVM HEALHNHYTQKSLSLSPGK |
| 20 | 339 | ER | QVQLVQSGAEVKKPGASVKVSCKASGYIFTNYWIQWVRQAPGQGLEWMGWINPN SGGTRYARNFQGRVTMTRDTSTSTVYMELSSLRSEDTAVYYCARGRYYYGSGSQ YHAFDIWGQGTMVTVSSASTKGPSVFPLAPSSKSTSGGTAALGCLVKDYFPEPV TVSWNSGALTSGVHTFPAVLQSSGLYSLSSVVTVPSSSLGTQTYICNVNHKPSN TKVDKRVEPKSCDKTHTCPPCPAPELLGGPSVFLFPPKPKDTLMISRTPEVTCV VVDVSHEDPEVKFNWYVDGVEVHNAKTKPREEQYNSTYRVVSVLTVLHQDWLNG KEYKCKVSNKALPAPIEKTISKAKGQPRRPQVYTLPPSREEMTKNQVSLTCLVK GFYPSDIAVEWESNGQPENNYKTTPPVLDSDGSFFLYSKLTVDKSRWQQGNVFS CSVMHEALHNHYTQKSLSLSPGK |
| 23a | 340 | (none) | EVQLLESGGGLVQPGGSLRLSCAASGFTFSSYSMNWVRQAPGKGLEWVAVISYD GRIKDYADSVKGRFTISRDNSKNTLYLQMNSLRAEDTAVYYCARVRGFSFWFDP WGQGTLVTVSSASTKGPSVFPLAPSSKSTSGGTAALGCLVKDYFPEPVTVSWNS GALTSGVHTFPAVLQSSGLYSLSSVVTVPSSSLGTQTYICNVNHKPSNTKVDKR |

TABLE 7-continued

| Binding Agent | SEQ ID | Fc mod. | Heavy Chain Sequence |
|---|---|---|---|
| | | | VEPKSCDKTHTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLNGKEYKCK<br>VSNKALPAPIEKTISKAKGQPREPQVYTLPPSREEMTKNQVSLTCLVKGFYPSD<br>IAVEWESNGQPENNYKTTPPVLDSDGSFFLYSKLTVDKSRWQQGNVFSCSVMHE<br>ALHNHYTQKSLSLSPGK |
| 23a | 341 | ER | EVQLLESGGGLVQPGGSLRLSCAASGFTFSSYSMNWVRQAPGKGLEWVAVISYD<br>GRIKDYADSVKGRFTISRDNSKNTLYLQMNSLRAEDTAVYYCARVRGFSFWFDP<br>WGQGTLVTVSSASTKGPSVFPLAPSSKSTSGGTAALGCLVKDYFPEPVTVSWNS<br>GALTSGVHTFPAVLQSSGLYSLSSVVTVPSSSLGTQTYICNVNHKPSNTKVDKR<br>VEPKSCDKTHTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLNGKEYKCK<br>VSNKALPAPIEKTISKAKGQPRRPQVYTLPPSREEMTKNQVSLTCLVKGFYPSD<br>IAVEWESNGQPENNYKTTPPVLDSDGSFFLYSKLTVDKSRWQQGNVFSCSVMHE<br>ALHNHYTQKSLSLSPGK |
| 23a | 342 | GA | EVQLLESGGGLVQPGGSLRLSCAASGFTFSSYSMNWVRQAPGKGLEWVAVISYD<br>GRIKDYADSVKGRFTISRDNSKNTLYLQMNSLRAEDTAVYYCARVRGFSFWFDP<br>WGQGTLVTVSSASTKGPSVFPLAPSSKSTSGGTAALGCLVKDYFPEPVTVSWNS<br>GALTSGVHTFPAVLQSSGLYSLSSVVTVPSSSLGTQTYICNVNHKPSNTKVDKR<br>VEPKSCDKTHTCPPCPAPELLAGPSVFLFPPKPKDTLMISRTPEVTCVVVDVSH<br>EDPEVKFNWYVDGVEVHNAKTKPREEQYNSTYRVVSVLTVLHQDWLNGKEYKCK<br>VSNKALPAPIEKTISKAKGQPREPQVYTLPPSREEMTKNQVSLTCLVKGFYPSD<br>IAVEWESNGQPENNYKTTPPVLDSDGSFFLYSKLTVDKSRWQQGNVFSCSVMHE<br>ALHNHYTQKSLSLSPGK |
| 23a | 343 | CS | EVQLLESGGGLVQPGGSLRLSCAASGFTFSSYSMNWVRQAPGKGLEWVAVISYD<br>GRIKDYADSVKGRFTISRDNSKNTLYLQMNSLRAEDTAVYYCARVRGFSFWFDP<br>WGQGTLVTVSSASTKGPSVFPLAPCSRSTSESTAALGCLVKDYFPEPVTVSWNS<br>GALTSGVHTFPAVLQSSGLYSLSSVVTVPSSNFGTQTYTCNVDHKPSNTKVDKT<br>VERKSCVECPPCPAPPVAGPSVFLFPPKPKDTLMISRTPEVTCVVVDVSHEDPE<br>VQFNWYVDGVEVHNAKTKPREEQFNSTFRVVSVLTVVHQDWLNGKEYKCKVSNK<br>GLPAPIEKTISKTKGQPREPQVYTLPPSREEMTKNQVSLTCLVKGFYPSDIAVE<br>WESNGQPENNYKTTPPMLDSDGSFFLYSKLTVDKSRWQQGNVFSCSVMHEALHN<br>HYTQKSLSLSPGK |
| 23a | 344 | LALA | EVQLLESGGGLVQPGGSLRLSCAASGFTFSSYSMNWVRQAPGKGLEWVAVISYD<br>GRIKDYADSVKGRFTISRDNSKNTLYLQMNSLRAEDTAVYYCARVRGFSFWFDP<br>WGQGTLVTVSSASTKGPSVFPLAPSSKSTSGGTAALGCLVKDYFPEPVTVSWNS<br>GALTSGVHTFPAVLQSSGLYSLSSVVTVPSSSLGTQTYICNVNHKPSNTKVDKR<br>VEPKSCDKTHTCPPCPAPEAAGGPSVFLFPPKPKDTLMISRTPEVTCVVVDVSH<br>EDPEVKFNWYVDGVEVHNAKTKPREEQYNSTYRVVSVLTVLHQDWLNGKEYKCK<br>VSNKALPAPIEKTISKAKGQPREPQVYTLPPSREEMTKNQVSLTCLVKGFYPSD<br>IAVEWESNGQPENNYKTTPPVLDSDGSFFLYSKLTVDKSRWQQGNVFSCSVMHE<br>ALHNHYTQKSLSLSPGK |
| 23b | 345 | (none) | EVQLLESGGGLVQPGGSLRLSCAASGFTFSSYSMNWVRQAPGKGLEWVAVISYD<br>GRIKDYADSVKGRFTISRDNSKNTLYLQMNSLRAEDTAVYYCARVRGFSFWFEP<br>WGQGTLVTVSSASTKGPSVFPLAPSSKSTSGGTAALGCLVKDYFPEPVTVSWNS<br>GALTSGVHTFPAVLQSSGLYSLSSVVTVPSSSLGTQTYICNVNHKPSNTKVDKR<br>VEPKSCDKTHTCPPCPAPELLGGPSVFLFPPKPKDTLMISRTPEVTCVVVDVSH<br>EDPEVKFNWYVDGVEVHNAKTKPREEQYNSTYRVVSVLTVLHQDWLNGKEYKCK<br>VSNKALPAPIEKTISKAKGQPREPQVYTLPPSREEMTKNQVSLTCLVKGFYPSD<br>IAVEWESNGQPENNYKTTPPVLDSDGSFFLYSKLTVDKSRWQQGNVFSCSVMHE<br>ALHNHYTQKSLSLSPGK |

As mentioned above, the binding agent can comprise an Ig heavy and/or light chain variable region with at least about 90% identity (e.g. at least about 91%, at least about 92%, at least about 93%, at least about 94%, at least about 95%, at least about 96%, at least about 97%, at least about 98%, or at least about 99% identity) to a specific heavy or light chain variable region sequence provided herein. Similarly, the CDRs of the Ig heavy and/or light chain variable region can have at least about 90% identity (e.g. at least about 91%, at least about 92%, at least about 93%, at least about 94%, at least about 95%, at least about 96%, at least about 97%, at least about 98%, or at least about 99% identity) to a specific CDR sequence provided herein. Thus, the Ig heavy and light chain variable region or CDR sequence can comprise at least one (e.g., 1 or more, 2 or more, 3 or more, 4 or more, 5 or more, 6 or more, 7 or more, 8 or more, 9 or more, or 10 or more, etc., as applicable based on the length of the sequence) amino acid modification (e.g., substitution, addition, or deletion) as compared to the specific sequences provided herein, provided the binding agent maintains the ability to specifically bind Dectin-2, optionally wherein the binding agent maintains the affinity of a binding agent with the specified sequences and/or competes with a binding agent having the specified sequences for binding to Dectin-2.

The amino acids of the sequences provided can be substituted with any other amino acid. Amino acids include naturally-occurring α-amino acids and their stereoisomers, as well as non-naturally occurring amino acids and their stereoisomers. "Stereoisomers" of a given amino acid refer to isomers having the same molecular formula and intramolecular bonds but different three-dimensional arrangements of bonds and atoms (e.g., an L-amino acid and the corresponding D-amino acid). The amino acids can be glycosylated (e.g., N-linked glycans, O-linked glycans, phosphoglycans, C-linked glycans, or glypiation) or deglycosylated.

Naturally-occurring amino acids are those encoded by the genetic code, as well as those amino acids that are later modified, e.g., hydroxyproline, γ-carboxyglutamate, and Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

Non-naturally occurring amino acids include, without limitation, amino acid analogs, amino acid mimetics, synthetic amino acids, N-substituted glycines, and N-methyl amino acids in either the L- or D-configuration that function in a manner similar to the naturally-occurring amino acids. For example, "amino acid analogs" can be unnatural amino acids that have the same basic chemical structure as naturally-occurring amino acids (i.e., a carbon that is bonded to a hydrogen, a carboxyl group, an amino group) but have modified side-chain groups or modified peptide backbones, e.g., homoserine, norleucine, methionine sulfoxide, and methionine methyl sulfonium. "Amino acid mimetics" refer to chemical compounds that have a structure that is different from the general chemical structure of an amino acid, but that functions in a manner similar to a naturally-occurring amino acid.

Amino acids may be referred to herein by either the commonly known three letter symbols or by the one-letter symbols recommended by the IUPAC-IUB Biochemical Nomenclature Commission.

The amino acid substitution can be conservative, semiconservative, or non-conservative with respect to the basic properties of the original amino acid residue. A "conservative" substitution refers to the replacement of one amino acid by another amino acid with a common property. A functional way to define common properties between individual amino acids is to analyze the normalized frequencies of amino acid changes between corresponding proteins of homologous organisms (Schulz and Schirmer, *Principles of Protein Structure*, Springer-Verlag, New York (1979)). According to such analyses, groups of amino acids may be defined where amino acids within a group exchange preferentially with each other, and therefore resemble each other most in their impact on the overall protein structure (Schulz and Schirmer, supra).

Amino acids are broadly grouped as "aromatic" or "aliphatic." An aromatic amino acid includes an aromatic ring. Examples of "aromatic" amino acids include histidine (H or His), phenylalanine (F or Phe), tyrosine (Y or Tyr), and tryptophan (W or Trp). Non-aromatic amino acids are broadly grouped as "aliphatic." Examples of "aliphatic" amino acids include glycine (G or Gly), alanine (A or Ala), valine (V or Val), leucine (L or Leu), isoleucine (I or Ile), methionine (M or Met), serine (S or Ser), threonine (T or Thr), cysteine (C or Cys), proline (P or Pro), glutamic acid (E or Glu), aspartic acid (D or Asp), asparagine (N or Asn), glutamine (Q or Gln), lysine (K or Lys), and arginine (R or Arg).

Aliphatic amino acids may be sub-divided into four sub-groups. The "large aliphatic non-polar sub-group" consists of valine, leucine, and isoleucine. The "aliphatic slightly-polar sub-group" consists of methionine, serine, threonine, and cysteine. The "aliphatic polar/charged sub-group" consists of glutamic acid, aspartic acid, asparagine, glutamine, lysine, and arginine. The "small-residue sub-group" consists of glycine and alanine. The group of charged/polar amino acids may be sub-divided into three sub-groups: the "positively-charged sub-group" consisting of lysine and arginine, the "negatively-charged sub-group" consisting of glutamic acid and aspartic acid, and the "polar sub-group" consisting of asparagine and glutamine.

Aromatic amino acids may be sub-divided into two sub-groups: the "nitrogen ring sub-group" consisting of histidine and tryptophan and the "phenyl sub-group" consisting of phenylalanine and tyrosine.

Examples of conservative amino acid substitutions include substitutions of amino acids within the sub-groups described above, for example, lysine for arginine and vice versa such that a positive charge may be maintained, glutamic acid for aspartic acid and vice versa such that a negative charge may be maintained, serine for threonine such that a free —OH can be maintained, and glutamine for asparagine such that a free —NH$_2$ can be maintained.

"Semi-conservative mutations" include amino acid substitutions of amino acids within the same groups listed above, but not within the same sub-group. For example, the substitution of aspartic acid for asparagine, or asparagine for lysine, involves amino acids within the same group, but different sub-groups. "Non-conservative mutations" involve amino acid substitutions between different groups, for example, lysine for tryptophan, or phenylalanine for serine, etc.

In addition, one or more amino acids can be inserted into the aforementioned immunoglobulin heavy or light chain variable region polypeptides. Any number of any suitable amino acids can be inserted into the amino acid sequence of the immunoglobulin heavy or light chain variable region polypeptide. In this respect, at least one amino acid (e.g., 2 or more, 5 or more, or 10 or more amino acids), but not more than 20 amino acids (e.g., 18 or less, 15 or less, or 12 or less amino acids), can be inserted into the amino acid sequence of the immunoglobulin heavy or light chain variable region polypeptide. Preferably, 1-10 amino acids (e.g., 1, 2, 3, 4, 5, 6, 7, 8, 9, or 10 amino acids) are inserted into the amino acid sequence of the immunoglobulin heavy or light chain variable region polypeptide. In this respect, the amino acid(s) can be inserted into any one of the aforementioned immunoglobulin heavy or light chain variable region polypeptides in any suitable location. In some embodiments, the amino acid(s) are inserted into a CDR (e.g., CDR1, CDR2, or CDR3) of the immunoglobulin heavy or light chain variable region polypeptide; in other embodiments, the amino acids are inserted into a framework region.

Further provided is a Dectin-2 binding agent (e.g., antibody or antibody fragment) that competes with a Dectin-2 binding agent (e.g., antibody or antibody fragment) having an immunoglobulin heavy and light chain variable region specifically provided herein (e.g., one of the binding agents provided herein), and preferably retains the biological activity of the Dectin-2 binding agent.

The "biological activity" of a Dectin-2 binding agent refers to, for example, binding affinity for Dectin-2 or a particular Dectin-2 epitope, pharmacokinetics, and cross-reactivity (e.g., with non-human homologs or orthologs of the Dectin-2 protein, or with other proteins or tissues). In some embodiments, the biological activity of the Dectin-2 binding agent includes the ability to increase Dectin-2 activity in vivo and/or in vitro. Examples of Dectin-2 activity include increased or enhanced expression and/or production of pro-inflammatory cytokines, increased expression of costimulatory molecules, such as CD40, CD86, and major histocompatibility complex (MHC) molecules, and increased phagocytosis. Examples of pro-inflammatory cytokines include Tumor Necrosis Factor (TNF) alpha, IL-1β, IL-2, IL-6, IL-23p19, IFNγ, IL-12p40, and IL-12p70.

The term "increase" or "enhance" as used in reference to Dectin-2 activity (e.g., Dectin-2 mediated signaling) means to increase or enhance such binding or signaling in any way and to any degree (e.g., act as an agonist). In some embodiments, Dectin-2 mediated signaling is increased sufficiently to reduce or alleviate any symptom of a disease or condition associated with deficient Dectin-2 activity, or which benefits from enhanced Dectin-2 activity, or to reverse, slow, or stop the progression or severity of such a disease or condition. The Dectin-2 binding agent of the invention preferably increases the activity of Dectin-2 by at least about 20%, about 30%, about 40%, about 50%, about 60%, about 70%, about 80%, about 90%, about 95%, about 100%, about 150%, about 200%, about 300%, or a range defined by any two of the foregoing values, as compared to the activity of Dectin-2 in Dectin-2 expressing cells in the absence of the Dectin-2 agent.

Other biological properties or characteristics of an antigen-binding agent recognized in the art include, for example, avidity, selectivity, solubility, folding, immunotoxicity, expression, and formulation. The aforementioned properties or characteristics can be observed, measured, and/or assessed using standard techniques including, but not limited to, ELISA, competitive ELISA, surface plasmon resonance analysis (BIACORE™), or KINEXA™, in vitro or in vivo neutralization assays, receptor-ligand binding assays, cytokine or growth factor production and/or secretion assays, and signal transduction and immunohistochemistry assays.

In some embodiments, the Dectin-2 binding agent (e.g., antibody or antibody fragment) increases or enhances Dectin-2 expression in cells of myeloid lineage, such as, for example, monocytes, macrophages, and dendritic cells, in comparison to Dectin-2 expression in cells of myeloid lineage not exposed to the Dectin-2 binding agent. This increase or enhancement in Dectin-2 expression can lead to an increased innate immune response. Without wishing to be bound by any particular theory, activation of the Dectin-2 signaling pathway is known to, for example, increase phagocytic activity and to activate MAPK and NF-κB signaling pathways, leading to the production of pro-inflammatory cytokines such as, for instance, TNFα, IL-1β, IL-2, IL-6, IL-23p19, IFNγ, IL-12p40, and IL-12p70.

In some embodiments, the Dectin-2 binding agent (e.g., antibody or antibody fragment) exhibits antibody dependent cell-mediated cytotoxicity (ADCC). ADCC is a mechanism of cell-mediated immune defense whereby an effector cell of the immune system lyses a target cell whose membrane-surface antigens have been bound by specific antibodies. ADCC is independent of the immune complement system that also lyses targets but does not require any other cell and is part of the adaptive immune response.

In some embodiments, the Dectin-2 binding agent (e.g., antibody or antibody fragment) promotes antibody dependent cell-mediated phagocytosis (ADCP). ADCP is a cellular process by which effector cells with phagocytic potential, such as monocytes and macrophages, can internalize target cells. Once phagocytosed, the target cell resides in a phagosome, which fuses with a lysosome to begin degradation of the target cell via an oxygen-dependent or independent mechanism. This function is dependent on opsonization, or identification of the target cell with a binding agent, which then also serves as a bridge between the target cell and the phagocytic cell. Mechanistically, the binding agent binds its cognate antigen on the target cell through its antigen recognition domain, and then recruits the phagocytic cell to the target with its Fc region. Once bound to the Fc receptor of the phagocytic cell, the target cell is ingested and degraded. This process also leads to the production of soluble factors by the effector cells that help initiate and drive the immune response.

In some embodiments, the Dectin-2 binding agent (e.g., antibody or antibody fragment) exhibits complement dependent cytotoxicity (CDC). CDC is an effector function of IgG and IgM antibodies. When the binding agents are bound to surface antigen, the classical complement pathway is triggered, resulting in formation of a membrane attack complex (MAC) and target cell lysis.

In some embodiments, the binding agents comprise an Fc region containing one or more modifications (e.g., amino acid insertion, deletion, and/or substitution) in the Fc region that results in modulated binding (e.g., increased binding or decreased binding) to one or more Fc receptors (e.g., FcγRI (CD64), FcγRIIA (CD32A), FcγRIIB (CD32B), FcγRIIIA (CD16a), and/or FcγRIIIB (CD16b)) as compared to a binding agent or antibody with the native Fc region lacking the mutation. In some embodiments, the binding agents contain one or more modifications (e.g., amino acid insertion, deletion, and/or substitution) in the Fc region that reduce the binding of the Fc region to FcγRIIB In some embodiments, the binding agents contain one or more modifications (e.g., amino acid insertion, deletion, and/or substitution) in the Fc region of the antibody that reduce the binding to FcγRIIB while maintaining the same binding or having increased binding to FcγRI (CD64), FcγRIIA (CD32A), and/or FcRγIIIA (CD16a) as compared to a binding agent or antibody with a native Fc region lacking the mutation. In some embodiments, the binding agents contain one of more modifications in the Fc region that increase the binding of the Fc region to FcγRIIB In some embodiments, the modifications substantially reduce or eliminate antibody effector functions.

The Fc region mutations can be in a CH2 domain, a CH3 domain, or a combination thereof. A "native Fc region" is synonymous with a "wild-type Fc region" and comprises an amino acid sequence that is identical to the amino acid sequence of an Fc region found in nature or identical to the amino acid sequence of the Fc region found in a native antibody. Native human Fc regions include a native sequence human IgG1 Fc region, native sequence human IgG2 Fc region, native sequence human IgG3 Fc region, and native sequence human IgG4 Fc region, as well as naturally occurring variants thereof. Native sequence Fc includes the various allotypes of Fcs (see, e.g., Jefferis et al., *mAbs,* 1(4): 332-338 (2009)).

In some embodiments, the Dectin-2 binding agent comprises an IgG (e.g., IgG1) Fc region or at least the CH2 domain thereof (e.g., a chimeric Fc comprising CH1, CH2, and CH3 regions of IgG1, but hinge region from a different Ig, such as IgG2). In some embodiments, the Dectin-2 binding agent comprises one or more of the following mutations or groups of mutations: SD (S239D), SDIE (S239D/I332E), SE (S267E), SEER (S267E/E345R), SELF (S267E/L328F), SDIEAL (S239D/I332E/A330L), GA (G236A), ALIE (A330L/I332E), GASDALIE (G236A/5239D/A330L/I332E), V9 (G237D/P238D/P271G/A330R), LALA (L234A/L235A), CS (C219S), NA (N297A), and V11 (G237D/P238D/H268D/P271G/A330R), and/or one or more mutations at the following amino acids: E345R, E233, G237, P238, H268, P271, N297, L328 and A330. All numbering refers to the EU numbering of human IgG (e.g., IgG1); however, the same mutations at corresponding positions of a different Ig (e.g., a chimeric Ig) can be used. In an embodiment, the mutation is SD. In an embodiment, the mutation is SDIE. In an embodiment, the mutation is SE. In an embodiment, the mutation is SELF. In an embodiment, the mutation is SDIEAL. In an embodiment, the mutation is GA. In an embodiment, the mutation is ALIE. In an embodiment, the mutation is GASDALIE. In an embodiment, the mutation is V9. In an embodiment, the mutation is LALA. In an embodiment, the mutation is CS. In an embodiment, the mutation is V11. In an embodiment, the mutation is E345R. In an embodiment, the mutation is NA. In an embodiment, the mutation is SEER. In an embodiment, the Dectin-2 binding agent comprises an Fc region with G236A, LALA and/or CS mutations, optionally wherein the Fc region is afucosylated (i.e., non-fucosylated). In some embodiments, the Dectin-2 binding agent comprises an Fc region with one or more of the above-listed mutations or groups of mutations, wherein the Fc region is afucosylated. Additional Fc region modifications for modulating Fc receptor binding are described in, for example, U.S. Patent Application Publication 2016/0145350 and U.S. Pat. No. 7,416,726 and which are hereby incorporated by reference in their entireties herein.

In an embodiment, the Dectin-2 binding agent is Binding Agent 1 disclosed herein (VH and VL regions respectively SEQ ID NOs: 243 and 283). In an embodiment, the Dectin-2 binding agent is Binding Agent 1 further comprising an Fc region. In another embodiment, the Dectin-2 binding agent is Binding Agent 1, wherein the Fc region is IgG1. In another embodiment, the Dectin-2 binding agent is Binding Agent 1, wherein the Fc region is IgG2. In another embodiment, the Dectin-2 binding agent is Binding Agent 1, wherein the Fc region is IgG1, and comprises the SE mutation. In another embodiment, the Dectin-2 binding agent is Binding Agent 1, wherein the Fc region is IgG1, and comprises the E345R mutation. In another embodiment, the Dectin-2 binding agent is Binding Agent 1, wherein the Fc region is IgG1, and comprises the SEER mutation. In another embodiment, the Dectin-2 binding agent is Binding Agent 1, wherein the Fc region is IgG1, and comprises the NA mutation. In another embodiment, the Dectin-2 binding agent is Binding Agent 1, wherein the Fc region is IgG1, and comprises the GA mutation. In another embodiment, the Dectin-2 binding agent is Binding Agent 1, wherein the Fc region is IgG1, comprises the GA mutation, and is also afucosylated. In another embodiment, the Dectin-2 binding agent is Binding Agent 1, wherein the Fc region is IgG1, and is afucosylated.

In an embodiment, the Dectin-2 binding agent is Binding Agent 20 disclosed herein (VH and VL regions respectively SEQ ID NOs: 261 and 302). In an embodiment, the Dectin-2 binding agent is Binding Agent 20 further comprising an Fc region. In another embodiment, the Dectin-2 binding agent is Binding Agent 20, wherein the Fc region is IgG1. In another embodiment, the Dectin-2 binding agent is Binding Agent 20, wherein the Fc region is IgG2. In another embodiment, the Dectin-2 binding agent is Binding Agent 20, wherein the Fc region is IgG1, and is afucosylated. In another embodiment, the Dectin-2 binding agent is Binding Agent 20, wherein the Fc region is IgG1, and comprises the GA mutation. In another embodiment, the Dectin-2 binding agent is Binding Agent 20, wherein the Fc region is IgG1, and comprises the LALA mutation. In another embodiment, the Dectin-2 binding agent is Binding Agent 20, wherein the Fc region is IgG1, and comprises the NA mutation. In another embodiment, the Dectin-2 binding agent is Binding Agent 20, wherein the Fc region is IgG1, and comprises the CS mutation. In another embodiment, the Dectin-2 binding agent is Binding Agent 20, wherein the Fc region is IgG2, and comprises the CS mutation. In another embodiment, the Dectin-2 binding agent is Binding Agent 20, wherein the Fc region comprises the E345R mutation. In another embodiment, the Dectin-2 binding agent is Binding Agent 20, wherein the Fc region is IgG1, comprises the GA mutation, and is also afucosylated.

In an embodiment, the Dectin-2 binding agent is Binding Agent 23a disclosed herein (VH and VL regions respectively SEQ ID NOs: 265 and 305). In an embodiment, the Dectin-2 binding agent is Binding Agent 23a further comprising an Fc region. In another embodiment, the Dectin-2 binding agent is Binding Agent 23a, wherein the Fc region is IgG1. In another embodiment, the Dectin-2 binding agent is Binding Agent 23a, wherein the Fc region is IgG2. In another embodiment, the Dectin-2 binding agent is Binding Agent 23a, wherein the Fc region is IgG1, and is afucosylated. In another embodiment, the Dectin-2 binding agent is Binding Agent 23a, wherein the Fc region is IgG1, and comprises the E345R mutation. In another embodiment, the Dectin-2 binding agent is Binding Agent 23a, wherein the Fc region is IgG1, and comprises the GA mutation. In another embodiment, the Dectin-2 binding agent is Binding Agent 23a, wherein the Fc region comprises the NA mutation. In another embodiment, the Dectin-2 binding agent is Binding Agent 23a, wherein the Fc region is IgG1, comprises the GA mutation, and is also afucosylated. In another embodiment, the Dectin-2 binding agent is Binding Agent 23a, wherein the Fc region is IgG2, and comprises the CS mutation. In another embodiment, the Dectin-2 binding agent is Binding Agent 23a, wherein the Fc region comprises the LALA mutation. In another embodiment, the Dectin-2 binding agent is Binding Agent 23b disclosed herein (VH and VL regions respectively SEQ ID NOs: 324 and 305), wherein the Fc region is IgG1, and wherein the heavy chain variable region includes a D101E mutation (Kabat numbering).

In some embodiments, the Fc region of the binding agents are modified to have an altered glycosylation pattern of the Fc region compared to the native non-modified Fc region.

Human immunoglobulin is glycosylated at the Asn297 residue in the Cγ2 domain of each heavy chain. This N-linked oligosaccharide is composed of a core heptasaccharide, N-acetylglucosamine4Mannose3 (G1cNAc4Man3). Removal of the heptasaccharide with endoglycosidase or PNGase F is known to lead to conformational changes in the Fc region, which can significantly reduce binding affinity to activating FcγR and lead to decreased effector function. The core heptasaccharide is often decorated with galactose, bisecting GlcNAc, fucose, or sialic acid, which differentially impacts Fc binding to activating and inhibitory FcγR. Additionally, it has been demonstrated that a2,6-sialyation enhances anti-inflammatory activity in vivo, while defucosylation leads to improved FcγRIIIa binding and a 10-fold increase in antibody-dependent cellular cytotoxicity and antibody-dependent phagocytosis. Specific glycosylation patterns, therefore, can be used to control inflammatory effector functions.

In some embodiments, the modification to alter the glycosylation pattern is a mutation. For example, a substitution at Asn297. In some embodiments, Asn297 is mutated to glutamine (N297Q). Methods for controlling immune response with antibodies that modulate FcγR-regulated signaling are described, for example, in U.S. Pat. No. 7,416,726 and U.S. Patent Application Publications 2007/0014795 and 2008/0286819, which are hereby incorporated by reference in their entireties.

In some embodiments, the binding agents are modified to contain an engineered Fab region with a non-naturally occurring glycosylation pattern. For example, hybridomas can be genetically engineered to secrete afucosylated mAb, desialylated mAb or deglycosylated Fc with specific mutations that enable increased FeRγIIIa binding and effector function. In some embodiments, the binding agents are engineered to be afucosylated.

In some embodiments, the entire Fc region is exchanged with a different Fc region, so that the Fab region is conjugated to a non-native Fc region. For example, the Fab region of atezolizumab, which normally comprises an IgG1 Fc region, can be conjugated to IgG2, IgG3, IgG4, or IgA, or the Fab region of nivolumab, which normally comprises an IgG4 Fc region, can be conjugated to IgG1, IgG2, IgG3, IgA1, or IgG2. In some embodiments, the Fc modified binding agent with a non-native Fc domain also comprises one or more additional amino acid modification, such as the S228P mutation within the IgG4 Fc, that modulate the stability of the Fc domain described. In some embodiments, the Fc modified binding agent with a non-native Fc domain also comprises one or more amino acid modifications described herein that modulate Fc binding to FcR.

In some embodiments, the modifications that modulate the binding of the Fc region to FcR do not alter the binding of the Fab region to its antigen when compared to the non-modified Fab. In other embodiments, the modifications that modulate the binding of the Fc region to FcR also increase the binding of the Fab region to its antigen when compared to the non-modified Fab.

In some embodiments, the Fc region is modified by attachment or inclusion of a transforming growth factor beta 1 (TGFβ1) receptor, or a fragment thereof, that is capable of binding TGFβ1. For example, the receptor can be TGFβ receptor II (TGFβRII) (see U.S. Pat. No. 9,676,863, incorporated herein in its entirety). In some embodiments, the TGFβ receptor is a human TGFβ receptor. In some embodiments, the Fc region (e.g., IgG) has a C-terminal fusion to a TGFβ receptor (e.g., TGFβRII) extracellular domain (ECD; e.g., amino acids 24-159 of SEQ ID NO: 9 of U.S. Pat. No. 9,676,863). An "Fc linker" may be used to attach the TGFβR extracellular domain to the Fc region (e.g., IgG), for example, a G4S4G linker. The Fc linker may be a short, flexible peptide that allows for the proper three-dimensional folding of the molecule while maintaining the binding-specificity to the targets. In some embodiments, the N-terminus of the TGFβ receptor is fused to the Fc region (with or without an Fc linker). In some embodiments, the C-terminus of the immunoglobulin heavy chain is fused to the TGFβ receptor (with or without an Fc linker), such as at the N-terminus of the TGFβ receptor. In some embodiments, the C-terminal lysine residue of the antibody heavy chain is mutated to alanine.

The Dectin-2 binding agent can have any suitable affinity to a Dectin-2 protein or an epitope thereof. The term "affinity" refers to the equilibrium constant for the reversible binding of two agents and is expressed as the dissociation constant ($K_D$). Affinity of a binding agent to a ligand, such as affinity of an antibody for an epitope, can be, for example, from about 1 picomolar (pM) to about 1 micromolar (μM) (e.g., from about 1 picomolar (pM) to about 1 nanomolar (nM), or from about 1 nM to about 1 micromolar (μM)). In one embodiment, the Dectin-2 binding agent can bind to a human Dectin-2 protein with a $K_D$ less than or equal to 1 micromolar (e.g., 0.9 μM, 0.8 μM, 0.7 μM, 0.6 μM, 0.5 μM, 0.4 μM, 0.3 μM, 0.2 μM, 0.1 μM, 0.05 μM, 0.025 μM, 0.01 μM, 0.001 μM, or a range defined by any two of the foregoing values). In one embodiment, the Dectin-2 binding agent can bind to a human Dectin-2 protein with a $K_D$ less than or equal to 200 nanomolar (e.g., 190 nM, 175 nM, 150 nM, 125 nM, 110 nM, 100 nM, 90 nM, 80 nM, 75 nM, 60 nM, 50 nM, 40 nM, 30 nM, 25 nM, 20 nM, 15 nM, 10 nM, 5 nM, 1 nM, or a range defined by any two of the foregoing values). In one embodiment, the Dectin-2 binding agent can bind to a human Dectin-2 protein with a $K_D$ less than or equal to 1 nanomolar (e.g., 0.9 nM, 0.8 nM, 0.7 nM, 0.6 nM, 0.5 nM, 0.4 nM, 0.3 nM, 0.2 nM, 0.1 nM, 0.05 nM, 0.025 nM, 0.01 nM, 0.001 nM, or a range defined by any two of the foregoing values). In another embodiment, the Dectin-2 binding agent can bind to human Dectin-2 with a $K_D$ less than or equal to 200 pM (e.g., 190 pM, 175 pM, 150 pM, 125 pM, 110 pM, 100 pM, 90 pM, 80 pM, 75 pM, 60 pM, 50 pM, 40 pM, 30 pM, 25 pM, 20 pM, 15 pM, 10 pM, 5 pM, 1 pM, or a range defined by any two of the foregoing values).

In some embodiments, the Dectin-2 binding agent also binds to a non-human species of Dectin-2 protein that is useful for development in animal models (e.g., tox screens and the like). In some embodiments, the Dectin-2 binding agent has an affinity for human Dectin-2 as described above, and also has an affinity for cynomolgus monkey or rat Dectin-2 that is within the above-mentioned ranges of affinity for human Dectin-2.

Immunoglobulin affinity for an antigen or epitope of interest can be measured using any art-recognized assay. Such methods include, for example, fluorescence activated cell sorting (FACS), separable beads (e.g., magnetic beads), surface plasmon resonance (SPR), solution phase competition (KINEXA™), antigen panning, and/or ELISA (see, Janeway et al. (eds.), *Immunobiology, 9th Ed.*, Garland Publishing, New York, NY (2017)). In some embodiments, the binding agent (e.g., an antibody or antigen-binding antibody fragment) has an affinity to human Dectin-2 as described above as determined by SPR or as determined by solution-phase competition assay. In some embodiments, the binding agent (e.g., an antibody or antigen-binding antibody fragment) has an affinity to human Dectin-2 as described above as determined by ELISA or as determined by FACs.

Nucleic Acids

The invention also provides nucleic acids that encode the immunoglobulin heavy chain polypeptide and/or the immunoglobulin light chain polypeptide of the Dectin-2 binding agent.

The term "nucleic acid sequence" is intended to encompass a polymer of DNA or RNA, i.e., a polynucleotide, which can be single-stranded or double-stranded and which can contain non-natural or altered nucleotides. The terms "nucleic acid" and "polynucleotide" as used herein refer to a polymeric form of nucleotides of any length, either ribonucleotides (RNA) or deoxyribonucleotides (DNA). These terms refer to the primary structure of the molecule, and thus include double- and single-stranded DNA, and double- and single-stranded RNA. The terms include, as equivalents, analogs of either RNA or DNA made from nucleotide analogs and modified polynucleotides such as, though not limited to, methylated and/or capped polynucleotides. Nucleic acids are typically linked via phosphate bonds to form nucleic acid sequences or polynucleotides, though many other linkages are known in the art (e.g., phosphorothioates, boranophosphates, and the like).

The nucleic acid can be part of a vector. Thus, also provided is a vector comprising one or more nucleic acid sequences encoding the immunoglobulin heavy chain polypeptide, the immunoglobulin light chain polypeptide, or both, of the Dectin-2 binding agent. Any type of vector can be used, particularly an expression vector useful for expressing the polypeptides in a cell. The vector can be, for example, a plasmid, episome, cosmid, viral vector (e.g., retroviral or adenoviral), or phage. Suitable vectors and methods of vector preparation are well known in the art (see, e.g., Sambrook et al., *Molecular Cloning, a Laboratory Manual*, 3rd edition, Cold Spring Harbor Press, Cold Spring Harbor, N.Y. (2001), and Ausubel et al., *Current Protocols in Molecular Biology*, Greene Publishing Associates and John Wiley & Sons, New York, N.Y. (1994)).

The vector preferably comprises expression control sequences, such as promoters, enhancers, polyadenylation signals, transcription terminators, internal ribosome entry sites (IRES), and the like, that provide for the expression of the coding sequence in a host cell. Exemplary expression control sequences are known in the art and described in, for example, Goeddel, *Gene Expression Technology: Methods in Enzymology*, Vol. 185, Academic Press, San Diego, Calif. (1990).

A large number of promoters, including constitutive, inducible, and repressible promoters, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the American Type Culture Collection (ATCC) as well as other commercial or individual sources. Promoters can be unidirectional (i.e., initiate transcription in one direction) or bi-directional (i.e., initiate transcription in either a 3' or 5' direction). Non-limiting examples of promoters include, for example, the T7 bacterial expression system, pBAD (araA) bacterial expression system, the cytomegalovirus (CMV) promoter, the SV40 promoter, the RSV promoter. Inducible promoters include, for example, the Tet system (U.S. Pat. Nos. 5,464,758 and 5,814,618), the Ecdysone inducible system (No et al., *Proc. Natl. Acad. Sci.*, 93: 3346-3351 (1996)), the T-REX™ system (Invitrogen, Carlsbad, CA), LACSWITCH™ system (Stratagene, San Diego, CA), and the Cre-ERT tamoxifen inducible recombinase system (Indra et al., *Nuc. Acid. Res.*, 27: 4324-4327 (1999); *Nuc. Acid. Res.*, 28: e99 (2000); U.S. Pat. No. 7,112,715; and Kramer & Fussenegger, *Methods Mol. Biol.*, 308: 123-144 (2005)).

The term "enhancer" as used herein, refers to a DNA sequence that increases transcription of, for example, a nucleic acid sequence to which it is operably linked. Enhancers can be located many kilobases away from the coding region of the nucleic acid sequence and can mediate the binding of regulatory factors, patterns of DNA methylation, or changes in DNA structure. A large number of enhancers from a variety of different sources are well known in the art and are available as or within cloned polynucleotides (from, e.g., depositories such as the ATCC as well as other commercial or individual sources). A number of polynucleotides comprising promoters (such as the commonly-used CMV promoter) also comprise enhancer sequences. Enhancers can be located upstream, within, or downstream of coding sequences.

The vector also can comprise a "selectable marker gene." The term "selectable marker gene," as used herein, refers to a nucleic acid sequence that allow cells expressing the nucleic acid sequence to be specifically selected for or against, in the presence of a corresponding selective agent. Suitable selectable marker genes are known in the art and described in, e.g., International Patent Application Publications WO 1992/008796 and WO 1994/028143; Wigler et al., *Proc. Natl. Acad. Sci. USA*, 77: 3567-3570 (1980); O'Hare et al., *Proc. Natl. Acad. Sci. USA*, 78: 1527-1531 (1981); Mulligan & Berg, *Proc. Natl. Acad. Sci. USA*, 78: 2072-2076 (1981); Colberre-Garapin et al., *J. Mol. Biol.*, 150: 1-14 (1981); Santerre et al., *Gene*, 30: 147-156 (1984); Kent et al., *Science*, 237: 901-903 (1987); Wigler et al., *Cell*, 11: 223-232 (1977); Szybalska & Szybalski, *Proc. Natl. Acad. Sci. USA*, 48: 2026-2034 (1962); Lowy et al., *Cell*, 22: 817-823 (1980); and U.S. Pat. Nos. 5,122,464 and 5,770,359.

In some embodiments, the vector is an "episomal expression vector" or "episome," which is able to replicate in a host cell, and persists as an extrachromosomal segment of DNA within the host cell in the presence of appropriate selective pressure (see, e.g., Conese et al., *Gene Therapy*, 11: 1735-1742 (2004)). Representative commercially available episomal expression vectors include, but are not limited to, episomal plasmids that utilize Epstein Barr Nuclear Antigen 1 (EBNA1) and the Epstein Barr Virus (EBV) origin of replication (oriP). The vectors pREP4, pCEP4, pREP7, and pcDNA3.1 from Invitrogen (Carlsbad, CA) and pBK-CMV from Stratagene (La Jolla, CA) represent non-limiting examples of an episomal vector that uses T-antigen and the SV40 origin of replication in lieu of EBNA1 and oriP.

Other suitable vectors include integrating expression vectors, which may randomly integrate into the host cell's DNA, or may include a recombination site to enable the specific recombination between the expression vector and the host cell's chromosome. Such integrating expression vectors may utilize the endogenous expression control sequences of the host cell's chromosomes to effect expression of the desired protein. Examples of vectors that integrate in a site specific manner include, for example, components of the flp-in system from Invitrogen (Carlsbad, CA) (e.g., pcDNA™5/FRT), or the cre-lox system, such as can be found in the pExchange-6 Core Vectors from Stratagene (La Jolla, CA). Examples of vectors that randomly integrate into host cell chromosomes include, for example, pcDNA3.1 (when introduced in the absence of T-antigen) from Invitrogen (Carlsbad, CA), UCOE from Millipore (Billerica, MA), and pCI or pFN10A (ACT) FLEXI™ from Promega (Madison, WI).

Viral vectors also can be used. Representative commercially available viral expression vectors include, but are not limited to, the adenovirus-based Per.C6 system available from Crucell, Inc. (Leiden, The Netherlands), the lentiviral-based pLP1 from Invitrogen (Carlsbad, CA), and the retroviral vectors pFB-ERV plus pCFB-EGSH from Stratagene (La Jolla, CA).

Cells

Nucleic acid sequences encoding the heavy and light chain immunoglobulin sequences can be provided to a cell on the same vector (i.e., in cis). A unidirectional promoter can be used to control expression of each nucleic acid sequence. In another embodiment, a combination of bidirectional and unidirectional promoters can be used to control expression of multiple nucleic acid sequences. Nucleic acid sequences encoding the inventive amino acid sequences alternatively can be provided to the population of cells on separate vectors (i.e., in trans). Each of the nucleic acid sequences in each of the separate vectors can comprise the same or different expression control sequences. The separate vectors can be provided to cells simultaneously or sequentially.

The vector(s) comprising the nucleic acid(s) encoding the inventive amino acid sequences can be introduced into a host cell that is capable of expressing the polypeptides encoded thereby, including any suitable prokaryotic or eukaryotic cell. As such, the invention provides an in vitro (isolated) cell or cell line comprising the inventive vector, which expresses the immunoglobulin heavy and light chain polypeptides. Preferred host cells are those that can be easily and reliably grown, have reasonably fast growth rates, have well characterized expression systems, and can be transformed or transfected easily and efficiently.

Examples of suitable prokaryotic cells include, but are not limited to, cells from the genera *Bacillus* (such as *Bacillus subtilis* and *Bacillus brevis*), *Escherichia* (such as *E. coli*), *Pseudomonas, Streptomyces, Salmonella*, and *Erwinia*. Particularly useful prokaryotic cells include the various strains of *Escherichia coli* (e.g., K12, HB101 (ATCC No. 33694), DH5a, DH10, MC1061 (ATCC No. 53338), and CC102).

Preferably, the vector is introduced into a eukaryotic cell. Suitable eukaryotic cells are known in the art and include, for example, yeast cells, insect cells, and mammalian cells. Examples of suitable yeast cells include those from the genera *Kluyveromyces, Pichia*, Rhino-sporidium, *Saccharomyces*, and *Schizosaccharomyces*. Preferred yeast cells include, for example, *Saccharomyces cerivisae* and *Pichia pastoris*.

Suitable insect cells are described in, for example, Kitts et al., Biotechniques, 14: 810-817 (1993); Lucklow, *Curr. Opin. Biotechnol.*, 4: 564-572 (1993); and Lucklow et al., *J. Virol.*, 67: 4566-4579 (1993). Preferred insect cells include Sf-9 and HI5 (Invitrogen, Carlsbad, CA).

Preferably, mammalian cells are utilized in the invention. A number of suitable mammalian host cells are known in the art, and many are available from ATCC. Examples of suitable mammalian cells include, but are not limited to, Chinese hamster ovary cells (CHO) cells, such as CHO-K1 cells (ATCC No. CCL61), CHO DHFR-cells (Urlaub et al., *Proc. Natl. Acad. Sci. USA*, 97: 4216-4220 (1980)), human embryonic kidney (HEK) 293 or 293T cells (ATCC No. CRL1573), and 3T3 cells (ATCC No. CCL92). Other suitable mammalian cell lines are the monkey COS-1 (ATCC No. CRL1650) and COS-7 cell lines (ATCC No. CRL1651), as well as the CV-1 cell line (ATCC No. CCL70). Further exemplary mammalian host cells include primate cell lines and rodent cell lines, including transformed cell lines. Normal diploid cells, cell strains derived from in vitro culture of primary tissue, as well as primary explants, are also suitable. Other suitable mammalian cell lines include, but are not limited to, mouse neuroblastoma N2A cells, HeLa, mouse L-929 cells, and BHK or HaK hamster cell lines, all of which are available from the ATCC. Suitable cell lines also include hybridomas. Methods for selecting suitable mammalian host cells and methods for transformation, culture, amplification, screening, and purification of cells are known in the art.

The mammalian cell can be a human cell. For example, the mammalian cell can be a human lymphoid or lymphoid derived cell line, such as a cell line of pre-B lymphocyte origin. Examples of human lymphoid cells lines include, without limitation, RAMOS (CRL-1596), Daudi (CCL-213), EB-3 (CCL-85), DT40 (CRL-2111), 18-81 (Jack et al., *Proc. Natl. Acad. Sci. USA*, 85: 1581-1585 (1988)), Raji cells (CCL-86), and derivatives thereof.

A nucleic acid sequence encoding the inventive amino acid sequence may be introduced into a cell by "transfection," "transformation," or "transduction." "Transfection," "transformation," or "transduction," as used herein, refer to the introduction of one or more exogenous polynucleotides into a host cell by using physical or chemical methods. Many transfection techniques are known in the art and include, for example, calcium phosphate DNA co-precipitation (see, e.g., Murray E. J. (ed.), *Methods in Molecular Biology*, Vol. 7, *Gene Transfer and Expression Protocols*, Humana Press (1991)); DEAE-dextran; electroporation; cationic liposome-mediated transfection; tungsten particle-facilitated microparticle bombardment (Johnston, Nature, 346: 776-777 (1990)); and strontium phosphate DNA co-precipitation (Brash et al., *Mol. Cell Biol.*, 7: 2031-2034 (1987)). Phage or viral vectors can be introduced into host cells, after growth of infectious particles in suitable packaging cells, many of which are commercially available.

Compositions

The invention provides a composition comprising the Dectin-2 binding agent or nucleic acid(s) encoding same optionally in a vector. Preferably, the composition is a pharmaceutically acceptable (e.g., physiologically acceptable) composition, which comprises a carrier, preferably a pharmaceutically acceptable (e.g., physiologically acceptable) carrier, and the Dectin-2 binding agent or nucleic acid(s) encoding same. Any suitable carrier can be used within the context of the invention, and such carriers are well known in the art. The choice of carrier will be determined, in part, by the particular site to which the composition may be administered and the particular method used to administer the composition. The composition optionally can be sterile. The composition can be frozen or lyophilized for storage and reconstituted in a suitable sterile carrier prior to use. The compositions can be generated in accordance with conventional techniques described in, e.g., Remington: *The Science and Practice of Pharmacy*, 21st Edition, Lippincott Williams & Wilkins, Philadelphia, PA (2001).

The composition can be formulated for parenteral administration, such as IV administration or administration into a body cavity or lumen of an organ. Alternatively, the composition can be injected intra-tumorally. Compositions for injection will commonly comprise the active ingredient dissolved or suspended in a pharmaceutically acceptable carrier. Among the acceptable vehicles and solvents that can be employed are water and an isotonic solution of one or more salts such as sodium chloride, e.g., Ringer's solution. In addition, sterile fixed oils can conventionally be employed as a solvent or suspending medium. For this purpose, any bland fixed oil can be employed, including synthetic monoglycerides or diglycerides. In addition, fatty acids such as oleic acid can likewise be used in the preparation of injectables. These compositions desirably are sterile and generally free of undesirable matter. These compositions can be sterilized by conventional, well known sterilization techniques. The compositions can contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like.

The composition can contain any suitable concentration of the Dectin-2 binding agent or nucleic acid(s) encoding same optionally in a vector, in some embodiments, a concentration effective to elicit a therapeutic response. The concentration can vary widely, and will be selected primarily based on fluid volumes, viscosities, body weight, and the like, in accordance with the particular mode of administration selected and the patient's needs. In certain embodiments, the concentration of the inventive immunoglobulin heavy chain polypeptide, the inventive immunoglobulin light chain polypeptide, the inventive Dectin-2 binding agent, the inventive nucleic acid sequence encoding any of the foregoing, or the inventive vector comprising the inventive nucleic acid sequence in a solution formulation for injection will range from about 0.1% (w/w) to about 10% (w/w).

Methods

The Dectin-2 binding agents provided herein can be used for any suitable purpose. For instance, the Dectin-2 binding agents can agonistically bind Dectin-2 expressing cells, and be used to activate or enhance Dectin-2 signaling therein (e.g., for therapeutic purposes). Accordingly, one aspect of the disclosure provides a method of treating a disease, condition, or disorder responsive to the activation and/or enhancement of Dectin-2 signaling in a mammal by administering a Dectin-2 binding agent, or composition comprising same, as described herein, to the mammal.

In some embodiments, the Dectin-2 binding agents can stimulate an antigen presenting cell (APC). Stimulation can occur by contacting an APC with a Dectin-2 binding agent at a dose and for a period of time sufficient to enhance Dectin-2 signaling in the APC, thereby generating a stimulated APC. In some embodiments, the APC is a cell of myeloid lineage. Examples of cells of myeloid lineage include monocytes, macrophages, and dendritic cells. In some embodiments, stimulated APCs produce at least one pro-inflammatory cytokine, examples of which include Tumor Necrosis Factor alpha, IL-1β, IL-2, IL-6, IL-23p19, IFNγ, IL-12p40, and IL-12p70. In some embodiments, stimulated APCs exhibit increased phagocytosis in comparison to APCs that have not been contacted by a Dectin-2 binding agent. In some embodiments, the stimulated APC is contacted with a cancer antigen to produce an antigen-contacted APC. The cancer antigen can be, for example, present in a cancer cell lysate or be part of a cancer cell. The cancer cell lysate or cancer cell can be taken or derived from an individual. In some embodiments, the individual has cancer.

In some embodiments, the stimulated APC or the antigen-contacted APC is introduced into an individual. In embodiments wherein the antigen used to contact the APC is taken or derived from an individual to produce an antigen-contacted APC, the antigen-contacted APC can be introduced into the individual. Such a stimulated APC or antigen-contacted APC can be autologous to the individual.

In some embodiments, the antigen-contacted APC is contacted with a T cell. The T cell can be introduced into an individual. The T cell and the antigen-contacted APC, with which the T cell is contacted, can each be autologous to the individual. In some embodiments, the individual has cancer.

As used herein, the terms "treat," "treatment," and "treating" refer to any indicia of success in the treatment or amelioration of an injury, pathology, condition (e.g., cancer), or symptom, including any objective or subjective parameter such as abatement; remission; diminishing of symptoms or making the symptom, injury, pathology, or condition more tolerable to the patient; reduction in the rate of symptom progression; decreasing the frequency or duration of the symptom or condition; or, in some situations, preventing the onset of the symptom. The treatment or amelioration of symptoms can be based on any objective or subjective parameter, including, for example, the result of a physical examination.

The terms "reduce" or "alleviate," as used herein with respect to the activity of a Dectin-2 binding agent, refer to the ability to substantially prohibit, prevent, restrain, slow, disrupt, alter, eliminate, stop, or reverse the progression or severity of a disease or condition (e.g., cancer) associated with a Dectin-2 protein.

The terms "cancer," "neoplasm," and "tumor" are used herein to refer to cells which exhibit autonomous, unregulated growth, such that the cells exhibit an aberrant growth phenotype characterized by a significant loss of control over cell proliferation. Cells of interest for detection, analysis, and/or treatment in the context of the invention include cancer cells (e.g., cancer cells from an individual with cancer), malignant cancer cells, pre-metastatic cancer cells, metastatic cancer cells, and non-metastatic cancer cells. Cancers of virtually every tissue are known. The phrase "cancer burden" refers to the quantum of cancer cells or cancer volume in a subject. Reducing cancer burden accordingly refers to reducing the number of cancer cells or the cancer cell volume in a subject. The term "cancer cell" as used herein refers to any cell that is a cancer cell (e.g., from any of the cancers for which an individual can be treated, e.g., isolated from an individual having cancer) or is derived from a cancer cell, e.g., clone of a cancer cell. For example, a cancer cell can be from an established cancer cell line, can be a primary cell isolated from an individual with cancer, can be a progeny cell from a primary cell isolated from an individual with cancer, and the like. In some embodiments, the term can also refer to a portion of a cancer cell, such as a sub-cellular portion, a cell membrane portion, or a cell lysate of a cancer cell. Many types of cancers are known to those of skill in the art, including solid tumors such as carcinomas, sarcomas, glioblastomas, melanomas, lymphomas, and myelomas, and circulating cancers such as leukemias.

As used herein, the term "cancer" includes any form of cancer, including but not limited to, solid tumor cancers (e.g., skin, lung, prostate, breast, gastric, bladder, colon, ovarian, pancreas, kidney, liver, glioblastoma, medulloblastoma, leiomyosarcoma, head & neck squamous cell carcinomas, melanomas, and neuroendocrine) and liquid cancers (e.g., hematological cancers); carcinomas; soft tissue tumors; sarcomas; teratomas; melanomas; leukemias; lymphomas; and brain cancers, including minimal residual disease, and including both primary and metastatic tumors.

Any cancer that can be influenced by cells expressing Dectin-2 is a suitable cancer to be treated by the subject methods and compositions. As used herein "Dectin-2 expression" refers to a cell that has a Dectin-2 receptor on the cell's surface.

Carcinomas are malignancies that originate in the epithelial tissues. Epithelial cells cover the external surface of the body, line the internal cavities, and form the lining of glandular tissues. Examples of carcinomas include, but are not limited to, adenocarcinoma (cancer that begins in glandular (secretory) cells such as cancers of the breast, pancreas, lung, prostate, stomach, gastroesophageal junction, and colon); adrenocortical carcinoma; hepatocellular carcinoma; renal cell carcinoma; ovarian carcinoma; carcinoma in situ; ductal carcinoma; carcinoma of the breast; basal cell carcinoma; squamous cell carcinoma (e.g., head and neck squamous cell carcinoma); transitional cell carcinoma; colon carcinoma; nasopharyngeal carcinoma; multilocular cystic renal cell carcinoma; oat cell carcinoma; large cell lung carcinoma; small cell lung carcinoma; non-small cell lung carcinoma; and the like. Carcinomas may be found in prostate, pancreas, colon, brain (usually as secondary metastases), lung, breast, and skin.

Soft tissue tumors are a highly diverse group of rare tumors that are derived from connective tissue. Examples of soft tissue tumors include, but are not limited to, alveolar soft part sarcoma; angiomatoid fibrous histiocytoma; chondromyoxid fibroma; skeletal chondrosarcoma; extraskeletal myxoid chondrosarcoma; clear cell sarcoma; desmoplastic small round-cell tumor; dermatofibrosarcoma protuberans; endometrial stromal tumor; Ewing's sarcoma; fibromatosis (Desmoid); fibrosarcoma, infantile; gastrointestinal stromal tumor; bone giant cell tumor; tenosynovial giant cell tumor; inflammatory myofibroblastic tumor; uterine leiomyoma; leiomyosarcoma; lipoblastoma; typical lipoma; spindle cell or pleomorphic lipoma; atypical lipoma; chondroid lipoma; well-differentiated liposarcoma; myxoid/round cell liposarcoma; pleomorphic liposarcoma; myxoid malignant fibrous histiocytoma; high-grade malignant fibrous histiocytoma; myxofibrosarcoma; malignant peripheral nerve sheath tumor; mesothelioma; neuroblastoma; osteochondroma; osteosarcoma; primitive neuroectodermal tumor; alveolar rhabdomyosarcoma; embryonal rhabdomyosarcoma; benign or malignant schwannoma; synovial sarcoma; Evan's tumor; nodular fasciitis; desmoid-type fibromatosis; solitary fibrous tumor; dermatofibrosarcoma protuberans (DF SP); angiosarcoma; epithelioid hemangioendothelioma; tenosynovial giant cell tumor (TGCT); pigmented villonodular synovitis (PVNS); fibrous dysplasia; myxofibrosarcoma; fibrosarcoma; synovial sarcoma; malignant peripheral nerve sheath tumor; neurofibroma; pleomorphic adenoma of soft tissue; and neoplasias derived from fibroblasts, myofibroblasts, histiocytes, vascular cells/endothelial cells, and nerve sheath cells.

A sarcoma is a rare type of cancer that arises in cells of mesenchymal origin, e.g., in bone or in the soft tissues of the body, including cartilage, fat, muscle, blood vessels, fibrous tissue, or other connective or supportive tissue. Different types of sarcoma are based on where the cancer forms. For example, osteosarcoma forms in bone, liposarcoma forms in fat, and rhabdomyosarcoma forms in muscle. Examples of sarcomas include, but are not limited to, askin's tumor; sarcoma botryoides; chondrosarcoma; ewing's sarcoma; malignant hemangioendothelioma; malignant schwannoma; osteosarcoma; and soft tissue sarcomas (e.g., alveolar soft part sarcoma; angiosarcoma; cystosarcoma phyllodesdermatofibrosarcoma protuberans (DFSP); desmoid tumor; desmoplastic small round cell tumor; epithelioid sarcoma; extraskeletal chondrosarcoma; extraskeletal osteosarcoma; fibrosarcoma; gastrointestinal stromal tumor (GIST); hemangiopericytoma; hemangiosarcoma (more commonly referred to as "angiosarcoma"); kaposi's sarcoma; leiomyosarcoma; liposarcoma; lymphangiosarcoma; malignant peripheral nerve sheath tumor (MPNST); neurofibrosarcoma; synovial sarcoma; and undifferentiated pleomorphic sarcoma).

A teratoma is a type of germ cell tumor that may contain several different types of tissue (e.g., can include tissues derived from any and/or all of the three germ layers: endoderm, mesoderm, and ectoderm), including, for example, hair, muscle, and bone. Teratomas occur most often in the ovaries in women, the testicles in men, and the tailbone in children.

Melanoma is a form of cancer that begins in melanocytes (cells that make the pigment melanin). Melanoma may begin in a mole (skin melanoma), but can also begin in other pigmented tissues, such as in the eye or in the intestines.

Merkel cell carcinoma is a rare type of skin cancer that usually appears as a flesh-colored or bluish-red nodule. It frequently appears on the face, head or neck. Merkel cell carcinoma is also called neuroendocrine carcinoma of the skin. In some embodiments, the Merkel cell carcinoma has metastasized when administration occurs.

Leukemias are cancers that start in blood-forming tissue, such as the bone marrow, and cause large numbers of abnormal blood cells to be produced and enter the bloodstream. For example, leukemias can originate in bone marrow-derived cells that normally mature in the bloodstream. Leukemias are named for how quickly the disease develops and progresses (e.g., acute versus chronic) and for the type of white blood cell that is affected (e.g., myeloid versus lymphoid). Myeloid leukemias are also called myelogenous or myeloblastic leukemias. Lymphoid leukemias are also called lymphoblastic or lymphocytic leukemia. Lymphoid leukemia cells may collect in the lymph nodes, which can become swollen. Examples of leukemias include, but are not limited to, Acute myeloid leukemia (AML), Acute lymphoblastic leukemia (ALL), Chronic myeloid leukemia (CIVIL), and Chronic lymphocytic leukemia (CLL).

Lymphomas ace cancers that begin in cells of the immune system. For example, lymphomas can originate in bone marrow-derived cells that normally mature in the lymphatic system. There are two basic categories of lymphomas. One category of lymphoma is Hodgkin lymphoma (HL), which is marked by the presence of a type of cell called the Reed-Sternberg cell. There are currently 6 recognized types of HL. Examples of Hodgkin lymphomas include nodular sclerosis classical Hodgkin lymphoma (CHL), mixed cellularity CHL, lymphocyte-depletion CHL, lymphocyte-rich CHL, and nodular lymphocyte predominant HL.

The other category of lymphoma is non-Hodgkin lymphomas (NHL), which includes a large, diverse group of cancers of immune system cells. Non-Hodgkin lymphomas can be further divided into cancers that have an indolent (slow-growing) course and those that have an aggressive (fast-growing) course. There are currently 61 recognized types of NHL. Examples of non-Hodgkin lymphomas include, but are not limited to, AIDS-related Lymphomas, anaplastic large-cell lymphoma, angioimmunoblastic lymphoma, blastic NK-cell lymphoma, Burkitt's lymphoma, Burkitt-like lymphoma (small non-cleaved cell lymphoma), chronic lymphocytic leukemia/small lymphocytic lymphoma, cutaneous T-Cell lymphoma, diffuse large B-Cell lymphoma, enteropathy-type T-Cell lymphoma, follicular lymphoma, hepatosplenic gamma-delta T-Cell lymphomas, T-Cell leukemias, lymphoblastic lymphoma, mantle cell lymphoma, marginal zone lymphoma, nasal T-Cell lymphoma, pediatric lymphoma, peripheral T-Cell lymphomas, primary central nervous system lymphoma, transformed lymphomas, treatment-related T-Cell lymphomas, and Waldenstrom's macroglobulinemia.

Brain cancers include any cancer of the brain tissues. Examples of brain cancers include, but are not limited to, gliomas (e.g., glioblastomas, astrocytomas, oligodendrogliomas, ependymomas, and the like), meningiomas, pituitary adenomas, and vestibular schwannomas, primitive neuroectodermal tumors (medulloblastomas).

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, and invasion of surrounding or distant tissues or organs, such as lymph nodes.

As used herein, the phrases "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs, therefore, tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable amount of cancerous cells in an organ or body part that is not directly connected to the organ of the original cancerous tumor. Metastasis can also be defined as several steps of a process, such as the departure of cancer cells from an original tumor site, and migration and/or invasion of cancer cells to other parts of the body.

As used herein the phrases "effective amount" and "therapeutically effective amount" refer to a dose of a substance such as a binding agent that produces therapeutic effects for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, Dosage Calculations (1999); *Goodman & Gilman's The Pharmacological Basis of Therapeutics*, 11$^{th}$ Edition (McGraw-Hill, 2006); and *Remington: The Science and Practice of Pharmacy*, 22$^{nd}$ Edition, (Pharmaceutical Press, London, 2012)).

As used herein, the terms "recipient," "individual," "subject," "host," and "patient" are used interchangeably and refer to any mammalian subject for whom diagnosis, treatment, or therapy is desired (e.g., humans). "Mammal" for purposes of treatment refers to any animal classified as a mammal, including humans, domestic and farm animals, and zoo, sports, or pet animals, such as dogs, horses, cats, cows, sheep, goats, pigs, camels, etc. In certain embodiments, the mammal is human.

As used herein, the term "administering" refers to parenteral, intravenous, intraperitoneal, intramuscular, intratumoral, intralesional, intranasal, or subcutaneous administration, oral administration, administration as a suppository, topical contact, intrathecal administration, or the implantation of a slow-release device, e.g., a mini-osmotic pump, to the subject.

Administration of a composition comprising the inventive immunoglobulin heavy chain polypeptide, the inventive immunoglobulin light chain polypeptide, the inventive Dectin-2 binding agent, the inventive nucleic acid sequence encoding any of the foregoing, or the inventive vector comprising the inventive nucleic acid sequence induces an immune response against a cancer in a mammal. An "immune response" can entail, for example, activation (induction) of one or more Dectin-2-associated pathways (signaling) in Dectin-2 expressing cells, which can lead to the expression of pro-inflammatory cytokines and/or increased phagocytosis in Dectin-2 expressing cells.

The inventive methods comprise administering a "therapeutically effective amount" of the binding agent. A "therapeutically effective amount" refers to an amount effective, at dosages and for periods of time necessary, to achieve a desired therapeutic result. The therapeutically effective amount may vary according to factors such as the disease state, age, sex, and weight of the individual, and the ability of the binding agent to elicit a desired response in the individual. For example, a therapeutically effective amount of a binding agent of the invention is an amount enhances the immune response against a cancer.

Alternatively, the pharmacologic and/or physiologic effect may be prophylactic, i.e., the effect completely or partially prevents a disease or symptom thereof. In this respect, the inventive method comprises administering a "prophylactically effective amount" of the binding agent. A "prophylactically effective amount" refers to an amount effective, at dosages and for periods of time necessary, to achieve a desired prophylactic result (e.g., prevention of disease onset).

A typical dose can be, for example, in the range of 1 µg/kg to 20 mg/kg of animal or human body weight; however, doses below or above this exemplary range are within the scope of the invention. The daily parenteral dose can be about 0.00001 µg/kg to about 20 mg/kg of total body weight (e.g., about 0.001 µg/kg, about 0.1 µg/kg, about 1 µg/kg, about 5 µg/kg, about 10 µg/kg, about 100 µg/kg, about 500 µg/kg, about 1 mg/kg, about 5 mg/kg, about 10 mg/kg, or a range defined by any two of the foregoing values), preferably from about 0.1 µg/kg to about 10 mg/kg of total body weight (e.g., about 0.5 µg/kg, about 1 µg/kg, about 50 µg/kg, about 150 µg/kg, about 300 µg/kg, about 750 µg/kg, about 1.5 mg/kg, about 5 mg/kg, or a range defined by any two of the foregoing values), more preferably from about 1 µg/kg to 5 mg/kg of total body weight (e.g., about 3 µg/kg, about 15 µg/kg, about 75 µg/kg, about 300 µg/kg, about 900 µg/kg, about 2 mg/kg, about 4 mg/kg, or a range defined by any two of the foregoing values), and even more preferably from about 0.5 to 15 mg/kg body weight per day (e.g., about 1 mg/kg, about 2.5 mg/kg, about 3 mg/kg, about 6 mg/kg, about 9 mg/kg, about 11 mg/kg, about 13 mg/kg, or a range defined by any two of the foregoing values). Therapeutic or prophylactic efficacy can be monitored by periodic assessment of treated patients. For repeated administrations over several days or longer, depending on the condition, the treatment can be repeated until a desired suppression of disease symptoms occurs. However, other dosage regimens may be useful and are within the scope of the invention. The desired dosage can be delivered by a single bolus administration of the composition, by multiple bolus administrations of the composition, or by continuous infusion administration of the composition.

The composition comprising an effective amount of the inventive immunoglobulin heavy chain polypeptide, the inventive immunoglobulin light chain polypeptide, the inventive binding agent, the inventive nucleic acid sequence encoding any of the foregoing, or the inventive vector comprising the inventive nucleic acid sequence can be administered to a mammal using standard administration techniques, including oral, intravenous, intraperitoneal, subcutaneous, pulmonary, transdermal, intramuscular, intranasal, buccal, sublingual, or suppository administration. The composition preferably is suitable for parenteral administration. The term "parenteral," as used herein, includes intravenous, intramuscular, subcutaneous, rectal, vaginal, and intraperitoneal administration. More preferably, the composition is administered to a mammal using peripheral systemic delivery by intravenous, intraperitoneal, or subcutaneous injection.

Once administered to a mammal (e.g., a human), the biological activity of the inventive binding agent can be measured by any suitable method known in the art. For example, the biological activity can be assessed by determining the stability of a particular binding agent. In one embodiment of the invention, the binding agent (e.g., an antibody) has an in vivo half life between about 30 minutes and 45 days (e.g., about 30 minutes, about 45 minutes, about 1 hour, about 2 hours, about 4 hours, about 6 hours, about 10 hours, about 12 hours, about 1 day, about 5 days, about 10 days, about 15 days, about 25 days, about 35 days, about 40 days, about 45 days, or a range defined by any two of the foregoing values). In another embodiment, the Dectin-2 binding agent has an in vivo half life between about 2 hours and 20 days (e.g., about 5 hours, about 10 hours, about 15 hours, about 20 hours, about 2 days, about 3 days, about 7 days, about 12 days, about 14 days, about 17 days, about 19 days, or a range defined by any two of the foregoing values). In another embodiment, the binding agent has an in vivo half life between about 10 days and about 40 days (e.g., about 10 days, about 13 days, about 16 days, about 18 days, about 20 days, about 23 days, about 26 days, about 29 days, about 30 days, about 33 days, about 37 days, about 38 days, about 39 days, about 40 days, or a range defined by any two of the foregoing values).

In addition to therapeutic uses, the binding agent described herein can be used in diagnostic or research applications. In this respect, the binding agent can be used in a method to diagnose a cancer. In a similar manner, the binding agent can be used in an assay to monitor Dectin-2 protein levels in a subject being tested for a disease or disorder that is associated with abnormal Dectin-2 expression. Research applications include, for example, methods that utilize the binding agent and a label to detect a Dectin-2 protein in a sample, e.g., in a human body fluid or in a cell or tissue extract. The binding agent can be used with or without modification, such as covalent or non-covalent labeling with a detectable moiety. For example, the detectable moiety can be a radioisotope (e.g., $^3$H, $^{14}$C, $^{32}$P, $^{35}$S, or $^{12}$I) a fluorescent or chemiluminescent compound (e.g., fluorescein isothiocyanate, rhodamine, or luciferin), an enzyme (e.g., alkaline phosphatase, beta-galactosidase, or horseradish peroxidase), or prosthetic groups. Any method known in the art for separately conjugating an antigen-binding agent (e.g., an antibody) to a detectable moiety may be employed in the context of the invention (see, e.g., Hunter et al., Nature, 194: 495-496 (1962); David et al., Biochemistry, 13: 1014-1021 (1974); Pain et al., J. Immunol. Meth., 40: 219-230 (1981); and Nygren, J. Histochem. and Cytochem., 30: 407-412 (1982)).

Dectin-2 protein levels can be measured using the inventive binding agent by any suitable method known in the art. Such methods include, for example, immunohistochemistry, immunofluorescence, radioimmunoassay (MA), and FACS. Normal or standard expression values of Dectin-2 protein can be established using any suitable technique, e.g., by combining a sample comprising, or suspected of comprising, a Dectin-2 polypeptide with a Dectin-2 specific antibody under conditions suitable to form an antigen-antibody complex. The antibody is directly or indirectly labeled with a detectable substance to facilitate detection of the bound or unbound antibody. Suitable detectable substances include various enzymes, prosthetic groups, fluorescent materials, luminescent materials, and radioactive materials (see, e.g., Zola, Monoclonal Antibodies: A Manual of Techniques, CRC Press, Inc. (1987)). The amount of Dectin-2 polypeptide expressed in a sample is then compared with a standard value.

Kits

The binding agent can be provided in a kit, i.e., a packaged combination of reagents in predetermined amounts with instructions for performing a diagnostic assay. If the binding agent is labeled with an enzyme, the kit desirably includes substrates and cofactors required by the enzyme (e.g., a substrate precursor which provides a detectable chromophore or fluorophore). In addition, other additives may be included in the kit, such as stabilizers, buffers (e.g., a blocking buffer or lysis buffer), and the like. The relative amounts of the various reagents can be varied to provide for concentrations in solution of the reagents which substantially optimize the sensitivity of the assay. The reagents may be provided as dry powders (typically lyophilized), including excipients which on dissolution will provide a reagent solution having the appropriate concentration.

Examples of Non-Limiting Aspects of the Disclosure

Aspects, including embodiments, of the invention described herein may be beneficial alone or in combination, with one or more other aspects or embodiments. Without limiting the foregoing description, certain non-limiting aspects of the disclosure numbered (1)-(33) are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below:

(1) A Dectin-2 binding agent comprising an immunoglobulin heavy chain variable region polypeptide and an immunoglobulin light chain variable region polypeptide, wherein:

the immunoglobulin heavy chain variable region polypeptide comprises a complementarity determining region 1 (HCDR1) comprising any one of SEQ ID NOs: 1-30, a complementarity determining region 2 (HCDR2) comprising any one of SEQ ID NOs: 31-64, and a complementarity determining region 3 (HCDR3) comprising any one of SEQ ID NOs: 65-103 or 323; or the immunoglobulin light chain variable region polypeptide comprises a complementarity determining region 1 (LCDR1) comprising any one of SEQ ID NOs: 104-125, a complementarity determining region 2 (LCDR2) comprising any one of SEQ ID NOs: 126-148, and a complementarity determining region 3 (LCDR3) comprising any one of SEQ ID NOs: 149-181.

(2) A Dectin-2 binding agent comprising an immunoglobulin heavy chain variable region of any one of SEQ ID NOs: 243-282 or 324, or at least the CDRs thereof; and an immunoglobulin light chain variable region of any one of SEQ ID NOs: 283-322 or at least the CDRs thereof.

(3) A Dectin-2 binding agent comprising an immunoglobulin heavy chain variable region polypeptide with an amino acid sequence that is at least 90% identical to any one of SEQ ID NOs: 243-282 or 324, and an immunoglobulin light chain variable region polypeptide with an amino acid sequence that is at least 90% identical to any one of SEQ ID NOs: 284-322.

(4) The Dectin-2 binding agent of any one of aspects 1-3, which comprises the heavy and light chain immunoglobulin polypeptides, or at least the CDRs thereof, of a Dectin-2 binding agent of Table 1.

(5) The Dectin-2 binding agent of any one of aspects 1-4, wherein the binding agent is an antibody, an antibody conjugate, or an antigen-binding fragment thereof.

(6) The Dectin-2 binding agent of aspect 5, wherein the binding agent is an antibody fragment selected from F(ab')2, Fab', Fab, Fv, scFv, dsFv, dAb, and a single chain binding polypeptide.

(7) The Dectin-2 binding agent of aspect 5, wherein the binding agent is an antibody.

(8) The Dectin-2 binding agent of any one of aspects 5-7, wherein the antibody is an IgG, IgM, IgA, IgD or IgE antibody.

(9) The Dectin-2 binding agent of any one of aspects 5-8, wherein the antibody is an IgG antibody.

(10) The Dectin-2 binding agent of aspect 9, wherein the IgG antibody comprises one or more mutations in the Fc region that result in modulated binding to one or more Fc receptors.

(11) The Dectin-2 binding agent of any one of aspects 7-10, wherein the antibody exhibits antibody dependent cell-mediated cytotoxicity (ADCC), antibody-dependent cell-mediated phagocytosis (ADCP), or complement dependent cytotoxicity (CDC).

(12) The Dectin-2 binding agent of any of aspects 1-11, wherein the binding agent is part of a bispecific antibody, chimeric antigen receptor, chimeric T cell receptor, or bispecific T-cell engager.

(13) A nucleic acid encoding the heavy chain immunoglobulin polypeptide of the Dectin-2 binding agent of any one of aspects 1-12.

(14) A nucleic acid encoding the light chain immunoglobulin polypeptide of the Dectin-2 binding agent of any one of aspects 1-12.

(15) A nucleic acid encoding the heavy chain immunoglobulin polypeptide and the light chain immunoglobulin polypeptide of the Dectin-2 binding agent of any one of aspects 1-12.

(16) A vector comprising the nucleic acid sequence of any one of aspects 13-15.

(17) An isolated cell comprising the nucleic acid of any one of aspects 13-15, optionally in a vector.

(18) A method of providing a Dectin-2 binding agent of any of aspects 1-12, the method comprising expressing in a cell in vitro one or more nucleic acids encoding the immunoglobulin heavy and light chain polypeptides thereof.

(19) A composition comprising the Dectin-2 binding agent of any one of aspects 1-12 or nucleic acid of any one of aspects 13-15, optionally in a vector, and a pharmaceutically acceptable carrier.

(20) The Dectin-2 binding agent of any one of aspects 1-12 or conjugate comprising same, or the composition of aspect 19, for use as a medicament for treating a disease, disorder, or condition in a mammal that is responsive to Dectin-2 inhibition or binding.

(21) The Dectin-2 binding agent or composition of aspect 20, wherein the disease, disorder, or condition is cancer.

(22) The Dectin-2 binding agent of any one of aspects 1-12 or the composition of aspect 19 for use as a medicament for enhancing an immune response in a mammal.

(23) The Dectin-2 binding agent for use according to aspect 22, wherein the immune response is an anti-tumor immune response.

(24) A method for treating a disease, disorder, or condition in a mammal that is responsive to Dectin-2 binding or inhibition, the method comprising administering the Dectin-2 binding agent of any one of aspects 1-12 or conjugate comprising same, or the composition of aspect 19, to the mammal.

(25) The method of aspect 24, wherein the disease, disorder, or condition is cancer.

(26) A hybridoma or cell line that expresses a Dectin-2 binding agent of any of aspects 1-12.

(27) A method of stimulating an antigen presenting cell (APC), the method comprising contacting an APC with a Dectin-2 binding agent of aspects 1-12 at a dose and for a period of time sufficient to enhance Dectin-2 signaling in the APC, thereby generating a stimulated APC.

(28) The method according to aspect 27, wherein the APC is a cell of myeloid lineage.

(29) The method according to aspect 28, wherein the myeloid cell is a monocyte, macrophage, or a dendritic cell.

(30) The method according to aspects 27-29, wherein the stimulated APC produces at least one pro-inflammatory cytokine and/or exhibits increased phagocytosis as compared to an APC that has not been contacted by a Dectin-2 binding agent.

(31) The method according to aspect 30, wherein the at least one pro-inflammatory cytokine is selected from the group consisting of TNFα, IL-1β, IL-2, IL-6, IL-23p19, IFNγ, IL-12p40, and IL-12p70.

(32) The method according to any of aspects 27-31, comprising contacting the stimulated APC with a cancer antigen to produce an antigen-contacted APC.

(33) The method according to any of aspects 28-32, wherein the cancer antigen is present in a cancer cell lysate or is part of a cancer cell.

EXAMPLES

Human monocytes were isolated from LRS chambers obtained from the Stanford Blood Center (Palo Alto, CA; chamber is a byproduct from leukapheresis) using RosetteSep™ Human Monocyte Enrichment Cocktail (STEMCELL Technologies Inc.) followed by the EasySep™ Human Monocyte Enrichment Kit without CD16 Depletion (STEMCELL Technologies Inc.) according to the manufacturer's instructions. The isolated human monocytes were used in the following experiments.

Example 1

In a first experiment, the isolated human monocytes were cultured in complete RPMI medium (10% FBS, P/S, glutamine) supplemented with 100 ng/mL hGM-CSF (PeproTech, Inc.). Following two days' incubation, the treated monocytes were harvested with a cell scraper and added to TC-treated 96-well plates (Corning Inc., Corning, NY) which were pre-coated with one of the antibody clones listed in FIG. 1. The antibody-coated 96-well plates used in this experiment were prepared by diluting the indicated antibody to 25 µg/mL in PBS, and incubating overnight at 4° C., followed by several PBS washes. After an 18 hour incubation, supernatants were collected and TNFα levels were measured by ELISA according to the manufacturer's instructions (Invitrogen eBioscience Human TNF alpha ELISA Ready-SET-Go!). The results of the first experiment are shown in FIG. 1. As can be seen in FIG. 1, a number of the tested antibodies triggered a significant increase in TNFα expression.

The tested antibodies correspond to Binding Agents 1-40 disclosed herein, as follows:

TABLE 8

| Tested Antibody | Binding Agent (VH and VL SEQ ID NOs) |
|---|---|
| R3H-P1C02 | 1 (SEQ ID NOs: 243 and 283) |
| R3H-P3A02 | 2 (SEQ ID NOs: 244 and 284) |
| R3H-P3H07 | 3 (SEQ ID NOs: 245 and 285) |
| R3M-P2C06 | 4 (SEQ ID NOs: 246 and 286) |
| R3C-PIE10 | 5 (SEQ ID NOs: 247 and 287) |
| R3H-P1D01 | 6 (SEQ ID NOs: 248 and 288) |
| R3H-P1C10 | 7 (SEQ ID NOs: 249 and 289) |
| R3H-P2D03 | 8 (SEQ ID NOs: 250 and 290) |
| R4H-P1G05 | 9 (SEQ ID NOs: 251 and 291) |
| R3M-P1C03 | 10 (SEQ ID NOs: 252 and 292) |
| R3H-P2G03 | 11 (SEQ ID NOs: 253 and 293) |
| R4H-P1G11 | 12 (SEQ ID NOs: 254 and 294) |
| R3H-P1B01 | 13 (SEQ ID NOs: 255 and 295) |
| R3C-PIC09 | 14 (SEQ ID NOs: 256 and 296) |
| R3H-P1G03 | 15 (SEQ ID NOs: 257 and 297) |
| R3M-P3B04 | 16 (SEQ ID NOs: 258 and 298) |
| R3H-P2F02 | 17 (SEQ ID NOs: 259 and 299) |
| R3M-P3B11 | 18 (SEQ ID NOs: 256 and 300) |
| R3M-PID05 | 19 (SEQ ID NOs: 260 and 301) |
| R3H-P1F05 | 20 (SEQ ID NOs: 261 and 302) |
| R3H-P1E01 | 21 (SEQ ID NOs: 262 and 303) |
| R3C-P2B08 | 22 (SEQ ID NOs: 263 and 304) |
| R3C-PIG05 | 23 (SEQ ID NOs: 264 and 305) |
| R3H-P1B11 | 24 (SEQ ID NOs: 266 and 306) |
| R3H-P2B10 | 25 (SEQ ID NOs: 267 and 307) |
| R3C-P3C07 | 26 (SEQ ID NOs: 268 and 308) |
| R3H-P3A06 | 27 (SEQ ID NOs: 269 and 309) |
| R3H-P3D01 | 28 (SEQ ID NOs: 270 and 310) |
| R3M-P2D05 | 29 (SEQ ID NOs: 271 and 311) |
| R3C-P2D05 | 30 (SEQ ID NOs: 272 and 312) |
| R3H-P2D12 | 31 (SEQ ID NOs: 273 and 313) |
| R3H-P2A09 | 32 (SEQ ID NOs: 274 and 314) |
| R3H-P2G01 | 33 (SEQ ID NOs: 275 and 315) |
| R3M-P3E03 | 34 (SEQ ID NOs: 276 and 316) |
| R3H-P3B09 | 35 (SEQ ID NOs: 277 and 317) |
| R4C-P1F06 | 36 (SEQ ID NOs: 278 and 318) |
| R3H-P2D07 | 37 (SEQ ID NOs: 279 and 319) |
| R3M-P3C04 | 38 (SEQ ID NOs: 280 and 320) |
| R3H-P1C12 | 39 (SEQ ID NOs: 281 and 321) |
| R3C-P1C01 | 40 (SEQ ID NOs: 282 and 322) |

Example 2

Figure 2:
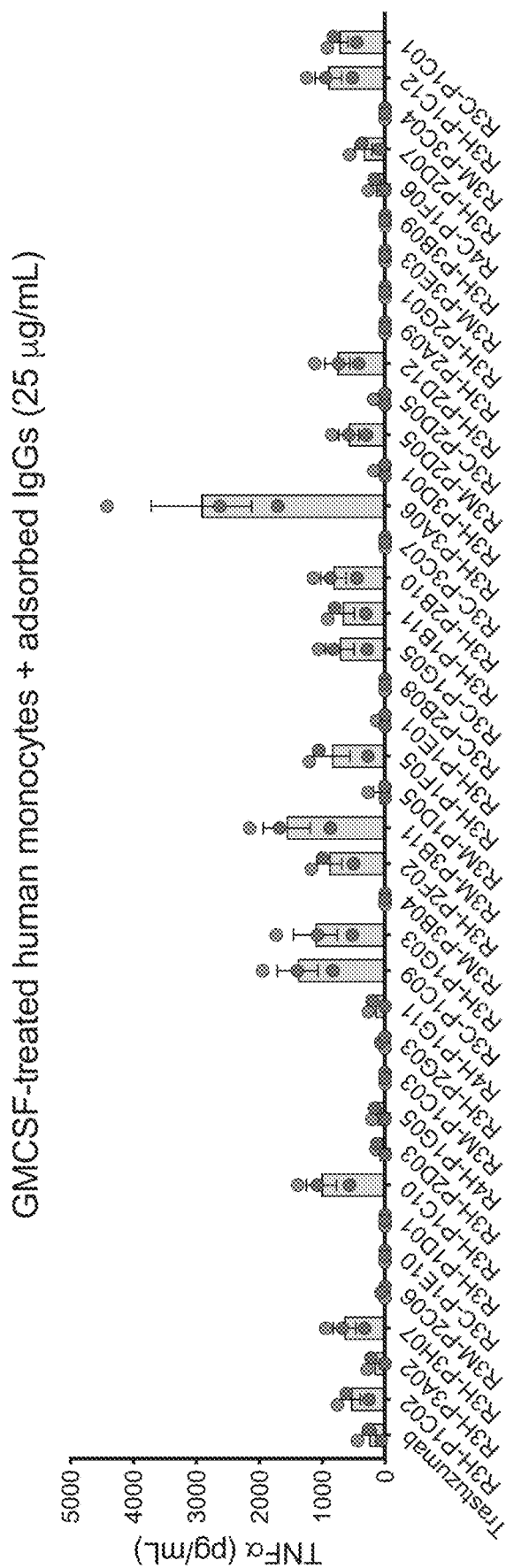
FIG. 2 is a bar graph of TNFα (pg/mL) secreted by GM-CSF-treated human monocytes which have been exposed to certain plate-adsorbed anti-Dectin-2 antibodies at a concentration of 25 μg/mL.

In a second experiment, isolated human monocytes were cultured in complete RPMI medium (10% FBS, P/S, glutamine) supplemented with 200 ng/mL hGM-CSF (PeproTech, Inc.). Following three days' incubation, the treated monocytes were harvested with a cell scraper and added to TC-treated 96 well plates (Corning Inc., Corning, NY), wherein the monocytes were stimulated with one of the antibody clones listed in FIG. 2 (in soluble form) at 100 µg/mL. After an 18 hour incubation, supernatants were collected and TNFα levels were measured by ELISA according to the manufacturer's instructions (Invitrogen eBioscience Human TNF alpha ELISA Ready-SET-Go!). The results of the first experiment are shown in FIG. 2. As can be seen in FIG. 2, a number of the tested antibodies triggered a significant increase in TNFα expression. The tested antibodies correspond to the Binding Agents disclosed herein as shown in Table 8.

Example 3

Figure 3:
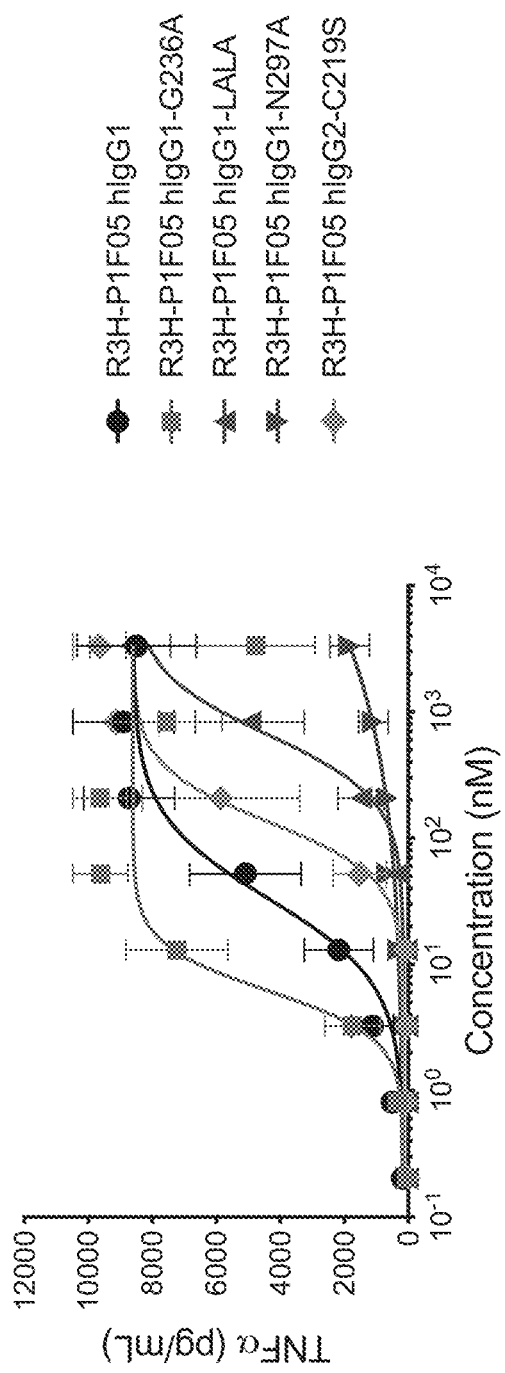
FIG. 3 is a graph of TNFα (pg/mL) secreted by GM-CSF-treated human monocytes stimulated with different concentrations (nM) of each of the indicated antibodies.

In a third experiment, isolated human monocytes were cultured in complete RPMI medium (10% FBS, P/S, gluta-mine) supplemented with human GM-CSF (PeproTech, Inc.). Following 6 days of incubation, macrophages were harvested and added to TC-treated 96 well plates (Corning Inc., Corning, NY), wherein the macrophages were stimulated with a dose titration of each of the indicated antibodies. After an 18 hour incubation, supernatants were collected and TNFα levels were measured by ELISA according to the manufacturer's instructions (Invitrogen eBioscience Human TNF alpha ELISA Ready-SET-Go!). As can be seen in FIG. 3, a number of the tested antibodies triggered a significant increase in TNFα expression. The tested antibodies were each R3H-P1F05 (corresponding to Binding Agent 20 disclosed herein, (i.e., comprising VH and VL regions respectively SEQ ID NOs: 261 and 302)), each with or without certain modifications to the Fc region of the antibody as shown on FIG. 3, including, for example, use of an IgG2 Fc domain instead of an IgG1 Fc domain.

Specifically, R3H-P1F05 comprises SEQ ID NOs: 326 and 334, R3H-P1F05 hIgG1-G236A comprises SEQ ID NOs 326 and 335, R3H-P1F05 hIgG1-LALA comprises SEQ ID NOs: 326 and 336, R3H-P1F05 hIgG1-N297A comprises SEQ ID NOs: 326 and 337, and R3H-P1F05 hIgG1-C219S comprises SEQ ID NOs: 326 and 338.

Example 4

Figure 4:
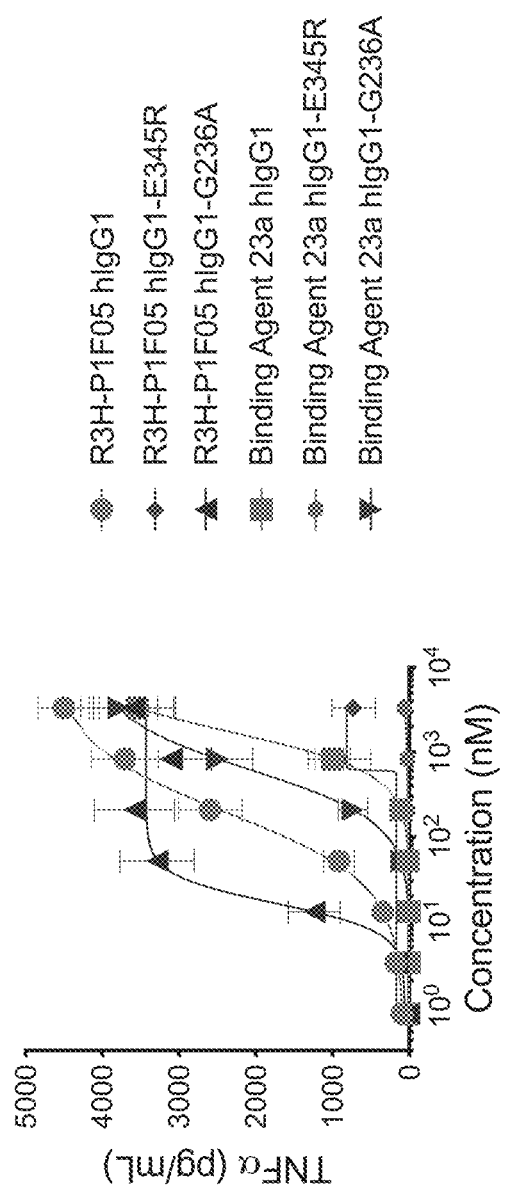
FIG. 4 is a graph of TNFα (pg/mL) secreted by GM-CSF-treated human monocytes stimulated with different concentrations (nM) of each of the indicated antibodies.

In a fourth experiment, isolated human monocytes were cultured in complete RPMI medium (10% FBS, P/S, glutamine) supplemented with human GM-CSF (PeproTech, Inc.). Following 5 days of incubation, macrophages were harvested and added to TC-treated 96 well plates (Corning Inc., Corning, NY), wherein the macrophages were stimulated with a dose titration of each of the indicated antibodies. After a 20 hour incubation, supernatants were collected and TNFα levels were measured by ELISA according to the manufacturer's instructions (Invitrogen eBioscience Human TNF alpha ELISA Ready-SET-Go!). As can be seen in FIG. 4, a number of the tested antibodies triggered a significant increase in TNFα expression. The tested antibodies were each R3H-P1F05 (corresponding to Binding Agent 20 disclosed herein (VH and VL regions respectively SEQ ID NOs: 261 and 302)), or an antibody corresponding to Binding Agent 23a disclosed herein (i.e., comprising VH and VL regions respectively SEQ ID NOs: 265 and 305), each with or without certain modifications to the Fc region of the antibody as shown in FIG. 4.

Specifically, R3H-P1F05 comprises SEQ ID NOs: 326 and 334, R3H-P1F05-E345R comprises SEQ ID NOs: 326 and 339, R3H-P1F05 hIgG1-G236A comprises SEQ ID NOs 326 and 335, Binding Agent 23a hIgG1 comprises SEQ ID NOs: 327 and 340, Binding Agent 23a hIgG1-E345R comprises SEQ ID NOs: 327 and 341, and Binding Agent 23a hIgG1-G236A comprises SEQ ID NOs: 327 and 342.

Example 5

In a fifth experiment, isolated human monocytes were cultured in complete RPMI medium (10% FBS, P/S, glutamine) supplemented with human M-CSF (PeproTech, Inc.). Following 6 days incubation, macrophages were harvested and added to TC-treated 96 well plates (Corning Inc., Corning, NY), wherein the macrophages were stimulated with a dose titration of each of the indicated antibodies. After a 20 hour incubation, supernatants were collected and TNFα levels were measured by ELISA according to the manufacturer's instructions (Invitrogen eBioscience Human TNF alpha ELISA Ready-SET-Go!). As can be seen in FIGS. 5A and 5B, a number of the tested antibodies triggered a significant increase in TNFα expression. The tested antibodies were each R3H-P1F05 (FIG. 5A) (corresponding to Binding Agent 20 disclosed herein (i.e., comprising VH and VL regions respectively SEQ ID NOs: 261 and 302)), or Binding Agent 23a disclosed herein (FIG. 5B) (i.e., comprising VH and VL regions respectively SEQ ID NOs: 265 and 305), each with or without certain modifications to the Fc region of the antibody as shown in FIGS. 5A and 5B, wherein "nf" stands for non-fucosylated (i.e, afucosylated).

Specifically, in FIG. 5A, R3H-P1F05 and R3H-P1F05-nf each comprise SEQ ID NOs: 326 and 334, and R3H-P1F05 hIgG1-G236A and R3H-P1F05 hIgG1-G236A-nf each comprise SEQ ID NOs 326 and 335. In FIG. 5B, Binding Agent 23a hIgG1 and Binding Agent 23a hIgG1-nf each comprise SEQ ID NOs: 327 and 340, and Binding Agent 23a hIgG1-G236A and Binding Agent 23a hIgG1-G236A-nf each comprise SEQ ID NOs: 327 and 342.

Example 6

In a sixth experiment, isolated human monocytes were cultured in complete RPMI medium (10% FBS, P/S, glutamine) supplemented with human M-CSF (PeproTech, Inc.). Following 5 days incubation, macrophages were harvested and added to TC-treated 96 well plates (Corning Inc., Corning, NY), wherein the macrophages were stimulated with a dose titration of each of the indicated antibodies. After a 20 hour incubation, supernatants were collected and TNFα levels were measured by ELISA according to the manufacturer's instructions (Invitrogen eBioscience Human TNF alpha ELISA Ready-SET-Go!). As can be seen in FIG. 6, a number of the tested antibodies triggered a significant increase in TNFα expression. The tested antibodies were each an antibody corresponding to Binding Agent 23a disclosed herein (i.e., comprising VH and VL regions respectively SEQ ID NOs: 265 and 305), or an antibody corresponding to Binding Agent 23b disclosed herein (i.e., comprising VH and VL regions respectively SEQ ID NOs: 324 and 305), each with or without certain modifications to the Fc region of the antibody as shown in FIG. 6, including use of an IgG2 domain instead of an IgG1 domain.

Specifically, Binding Agent 23a hIgG1 comprises SEQ ID NOs: 327 and 340, Binding Agent 23a hIgG1-G236A comprises SEQ ID NOs: 327 and 342, Binding Agent 23b hIgG1 comprises SEQ ID NOs: 327 and 345, Binding Agent 23a hIgG2-C219S comprises SEQ ID NOs: 327 and 343, and Binding Agent 23a hIgG1-LALA comprises SEQ ID NOs: 327 and 344.

Example 7

Figure 7:
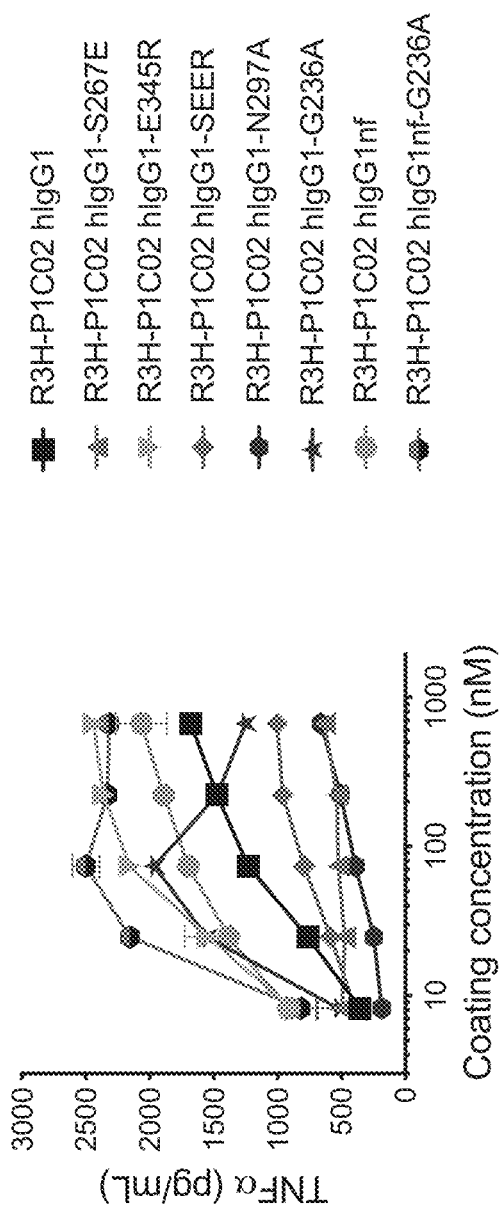
FIG. 7 is a graph of TNFα (pg/mL) secreted by GM-CSF-treated human monocytes stimulated with different concentrations (nM) of each of the indicated antibodies.

In a seventh experiment, isolated human monocytes were cultured in complete RPMI medium (10% FBS, P/S, glutamine) supplemented with human GM-CSF (PeproTech, Inc.). Following 3 days incubation, macrophages were harvested and added to TC-treated 96 well plates (Corning Inc., Corning, NY), which were pre-coated with the indicated antibodies. The antibody-coated 96-well plates used in this experiment were prepared by diluting the indicated antibody in PBS and incubating overnight at 4° C., followed by several PBS washes. After a 20 hour incubation, supernatants were collected and TNFα levels were measured by ELISA according to the manufacturer's instructions (Invitrogen eBioscience Human TNF alpha ELISA Ready-SET-Go!). As can be seen in FIG. 7, a number of the tested antibodies triggered a significant increase in TNFα expression. The tested antibodies were each R3H-P1C02 (corresponding to Binding Agent 1 disclosed herein (i.e., comprising VH and VL regions respectively SEQ ID NOs: 243 and 283)), with or without certain modifications to the Fc region of the antibody as shown in FIG. 7, wherein "nf" stands for non-fucosylated (i.e, afucosylated).

Specifically, each of R3H-P1C02 hIgG1 and R3H-P1C02 hIgG1nf comprises SEQ ID NOs: 325 and 328, R3H-P1CO2 hIgG1-S267E comprises SEQ ID NOs: 325 and 329, R3H-P1C02 hIgG1-E345R comprises SEQ ID NOs: 325 and 330, R3H-P1C02 hIgG1-SEER comprises SEQ ID NOs: 325 and 331, R3H-P1CO2 hIgG1-N297A comprises SEQ ID NOs: 325 and 332, and each of R3H-P1C02 hIgG1-G236A and R3H-P1C02 hIgG1nf-G236A comprises SEQ ID NOs: 325 and 333.

The terms "about" and "around," as used herein to modify a numerical value, indicate a close range surrounding the numerical value. Thus, if "X" is the value, "about X" or "around X" indicates a value of from 0.9× to 1.1×, e.g., from 0.95× to 1.05× or from 0.99× to 1.01×. A reference to "about X" or "around X" specifically indicates at least the values X, 0.95×, 0.96×, 0.97×, 0.98×, 0.99×, 1.01×, 1.02×, 1.03×, 1.04×, and 1.05×. Accordingly, "about X" and "around X" are intended to teach and provide written description support for a claim limitation of, e.g., "0.98×."

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A Dectin-2 binding agent comprising an immunoglobulin heavy chain variable region polypeptide and an immunoglobulin light chain variable region polypeptide, wherein, according to Kabat numbering:
the immunoglobulin heavy chain variable region polypeptide comprises a complementarity determining region 1 (HCDR1) comprising SEQ ID NO: 21, a complementarity determining region 2 (HCDR2) comprising SEQ ID NO: 52, and a complementarity determining region 3 (HCDR3) comprising SEQ ID NO: 86, and
the immunoglobulin light chain variable region polypeptide comprises a complementarity determining region 1 (LCDR1) comprising SEQ ID NO: 110, a complementarity determining region 2 (LCDR2) SEQ ID NO: 140, and a complementarity determining region 3 (LCDR3) comprising SEQ ID NO: 166.

2. A Dectin-2 binding agent of claim 1, wherein the immunoglobulin heavy chain variable region polypeptide has an amino acid sequence that is at least 90% identical to SEQ ID NO: 265, and the immunoglobulin light chain variable region polypeptide has an amino acid sequence that is at least 90% identical to SEQ ID NO: 305.

3. The Dectin-2 binding agent of claim 1, wherein the binding agent is an antibody, an antibody conjugate, or an antigen-binding fragment thereof.

4. The Dectin-2 binding agent of claim 3, wherein the binding agent is an antibody fragment selected from F(ab')$_2$, Fab', Fab, Fv, scFv, dsFv, and a single chain binding polypeptide.

5. The Dectin-2 binding agent of claim 3, wherein the binding agent is an antibody.

6. The Dectin-2 binding agent of claim 3, wherein the antibody is an IgG, IgM, IgA, IgD or IgE antibody.

7. The Dectin-2 binding agent of claim 3, wherein the antibody is an IgG antibody.

8. The Dectin-2 binding agent of claim 7, wherein the IgG antibody comprises one or more mutations in the Fc region that result in modulated binding to one or more Fc receptors.

9. The Dectin-2 binding agent of claim 5, wherein the antibody exhibits antibody dependent cell-mediated cytotoxicity (ADCC), antibody-dependent cell-mediated phagocytosis (ADCP), or complement dependent cytotoxicity (CDC).

10. The Dectin-2 binding agent of claim 1, wherein the binding agent is, or is part of, a multispecific or bispecific antibody, chimeric antigen receptor, chimeric T cell receptor, bispecific T-cell engager, multivalent antibody, diabody, triabody, tetrabody, hexabody, bis-scFV fragment, Fab dimer, or Fab trimer.

11. A Dectin-2 binding agent comprising an immunoglobulin heavy chain variable region polypeptide comprising complementarity determining regions of SEQ ID NO: 265 and an immunoglobulin light chain variable region polypeptide comprising complementarity determining regions of SEQ ID NO: 305.

12. A Dectin-2 binding agent comprising an immunoglobulin heavy chain variable region polypeptide of SEQ ID NO: 265 and an immunoglobulin light chain variable region polypeptide of SEQ ID NO: 305.

13. The Dectin-2 binding agent of claim 12, wherein the binding agent is an antibody, an antibody conjugate, or an antigen-binding fragment thereof.

14. The Dectin-2 binding agent of claim 13, wherein the antibody is an IgG antibody.

15. The Dectin-2 binding agent of claim 14, wherein the IgG antibody is an IgG1 antibody comprising a Fc region with alanine at position 236.

16. The Dectin-2 binding agent of claim 15, wherein the Fc region of the IgG1 antibody is afucosylated.

17. The Dectin-2 binding agent of claim 14, wherein the IgG antibody is an IgG1 antibody comprising a Fc region that is afucosylated.

18. A composition comprising the Dectin-2 binding agent of claim 1, and a pharmaceutically acceptable carrier.

19. A hybridoma or cell line that expresses a Dectin-2 binding agent of claim 1.

20. A method for enhancing an immune response in a mammal, the method comprising administering the Dectin-2 binding agent of claim 1 to the mammal, wherein the mammal has a cancer selected from the group consisting of head and neck squamous cell carcinoma, breast cancer, colorectal cancer, non-small cell lung cancer, ovarian cancer, pancreatic ductal adenocarcinoma, and renal cell carcinoma.

21. The method of claim 20, wherein the immune response is an anti-tumor immune response.

22. A method for treating a disease, disorder, or condition in a mammal that is responsive to Dectin-2 binding or activation, the method comprising administering the Dectin-2 binding agent of claim 1 to the mammal, wherein the disease, disorder, or condition is a cancer selected from the group consisting of head and neck squamous cell carcinoma, breast cancer, colorectal cancer, non-small cell lung cancer, ovarian cancer, pancreatic ductal adenocarcinoma, and renal cell carcinoma.

23. A method of stimulating an antigen presenting cell (APC) in a mammal having a cancer selected from the group consisting of head and neck squamous cell carcinoma, breast cancer, colorectal cancer, non-small cell lung cancer, ovarian cancer, pancreatic ductal adenocarcinoma, and renal cell carcinoma, the method comprising contacting an APC with a Dectin-2 binding agent of claim 1 at a dose and for a period of time sufficient to enhance Dectin-2 signaling in the APC, thereby generating a stimulated APC.

24. The method according to claim 23, wherein the APC is a cell of myeloid lineage.

25. The method according to claim 24, wherein the myeloid cell is a monocyte, macrophage, or a dendritic cell.

26. The method according to claim 13, wherein the stimulated APC produces at least one pro-inflammatory cytokine and/or exhibits increased phagocytosis as compared to an APC that has not been contacted by a Dectin-2 binding agent.

27. The method according to claim 26, wherein the at least one pro-inflammatory cytokine is selected from the group consisting of TNFα, IL-10, IL-2, IL-6, IL-23p19, IFNγ, IL-12p40, and IL-12p70.

28. The method according to claim 23, comprising contacting the stimulated APC with a cancer antigen to produce an antigen-contacted APC.

29. The method according to claim 28, wherein the cancer antigen is present in a cancer cell lysate or is part of a cancer cell.

* * * * *

```
                              SEQUENCE LISTING

Sequence total quantity: 346
SEQ ID NO: 1            moltype = AA   length = 5
FEATURE                 Location/Qualifiers
REGION                  1..5
                        note = Synthetic
source                  1..5
                        mol_type = protein
                        organism = synthetic construct
SEQUENCE: 1
SYYMQ                                                                     5

SEQ ID NO: 2            moltype = AA   length = 5
FEATURE                 Location/Qualifiers
REGION                  1..5
                        note = Synthetic
source                  1..5
                        mol_type = protein
                        organism = synthetic construct
SEQUENCE: 2
TYYMH                                                                     5

SEQ ID NO: 3            moltype = AA   length = 5
FEATURE                 Location/Qualifiers
REGION                  1..5
                        note = Synthetic
source                  1..5
                        mol_type = protein
                        organism = synthetic construct
SEQUENCE: 3
NFGIN                                                                     5

SEQ ID NO: 4            moltype = AA   length = 5
FEATURE                 Location/Qualifiers
REGION                  1..5
                        note = Synthetic
source                  1..5
                        mol_type = protein
                        organism = synthetic construct
SEQUENCE: 4
SYDIN                                                                     5

SEQ ID NO: 5            moltype = AA   length = 5
FEATURE                 Location/Qualifiers
REGION                  1..5
                        note = Synthetic
source                  1..5
                        mol_type = protein
                        organism = synthetic construct
SEQUENCE: 5
GYYVH                                                                     5

SEQ ID NO: 6            moltype = AA   length = 5
FEATURE                 Location/Qualifiers
REGION                  1..5
                        note = Synthetic
source                  1..5
                        mol_type = protein
                        organism = synthetic construct
SEQUENCE: 6
SYWMS                                                                     5

SEQ ID NO: 7            moltype = AA   length = 5
FEATURE                 Location/Qualifiers
REGION                  1..5
                        note = Synthetic
source                  1..5
                        mol_type = protein
                        organism = synthetic construct
SEQUENCE: 7
SQYMH                                                                     5

SEQ ID NO: 8            moltype = AA   length = 5
FEATURE                 Location/Qualifiers
```

```
REGION               1..5
                     note = Synthetic
source               1..5
                     mol_type = protein
                     organism = synthetic construct
SEQUENCE: 8
TYYMN                                                                   5

SEQ ID NO: 9         moltype = AA  length = 5
FEATURE              Location/Qualifiers
REGION               1..5
                     note = Synthetic
source               1..5
                     mol_type = protein
                     organism = synthetic construct
SEQUENCE: 9
SYFMH                                                                   5

SEQ ID NO: 10        moltype = AA  length = 5
FEATURE              Location/Qualifiers
REGION               1..5
                     note = Synthetic
source               1..5
                     mol_type = protein
                     organism = synthetic construct
SEQUENCE: 10
TWYMQ                                                                   5

SEQ ID NO: 11        moltype = AA  length = 5
FEATURE              Location/Qualifiers
REGION               1..5
                     note = Synthetic
source               1..5
                     mol_type = protein
                     organism = synthetic construct
SEQUENCE: 11
SYAIS                                                                   5

SEQ ID NO: 12        moltype = AA  length = 5
FEATURE              Location/Qualifiers
REGION               1..5
                     note = Synthetic
source               1..5
                     mol_type = protein
                     organism = synthetic construct
SEQUENCE: 12
RYYLH                                                                   5

SEQ ID NO: 13        moltype = AA  length = 5
FEATURE              Location/Qualifiers
REGION               1..5
                     note = Synthetic
source               1..5
                     mol_type = protein
                     organism = synthetic construct
SEQUENCE: 13
GQWVH                                                                   5

SEQ ID NO: 14        moltype = AA  length = 5
FEATURE              Location/Qualifiers
REGION               1..5
                     note = Synthetic
source               1..5
                     mol_type = protein
                     organism = synthetic construct
SEQUENCE: 14
PNYIQ                                                                   5

SEQ ID NO: 15        moltype = AA  length = 5
FEATURE              Location/Qualifiers
REGION               1..5
                     note = Synthetic
source               1..5
                     mol_type = protein
                     organism = synthetic construct
SEQUENCE: 15
ASYIH                                                                   5

SEQ ID NO: 16        moltype = AA  length = 5
```

```
                        -continued

FEATURE                 Location/Qualifiers
REGION                  1..5
                        note = Synthetic
source                  1..5
                        mol_type = protein
                        organism = synthetic construct
SEQUENCE: 16
DSHLH                                                                      5

SEQ ID NO: 17           moltype = AA  length = 5
FEATURE                 Location/Qualifiers
REGION                  1..5
                        note = Synthetic
source                  1..5
                        mol_type = protein
                        organism = synthetic construct
SEQUENCE: 17
SYWMH                                                                      5

SEQ ID NO: 18           moltype = AA  length = 5
FEATURE                 Location/Qualifiers
REGION                  1..5
                        note = Synthetic
source                  1..5
                        mol_type = protein
                        organism = synthetic construct
SEQUENCE: 18
NYWIQ                                                                      5

SEQ ID NO: 19           moltype = AA  length = 5
FEATURE                 Location/Qualifiers
REGION                  1..5
                        note = Synthetic
source                  1..5
                        mol_type = protein
                        organism = synthetic construct
SEQUENCE: 19
NYYMH                                                                      5

SEQ ID NO: 20           moltype = AA  length = 5
FEATURE                 Location/Qualifiers
REGION                  1..5
                        note = Synthetic
source                  1..5
                        mol_type = protein
                        organism = synthetic construct
SEQUENCE: 20
GYDMQ                                                                      5

SEQ ID NO: 21           moltype = AA  length = 5
FEATURE                 Location/Qualifiers
REGION                  1..5
                        note = Synthetic
source                  1..5
                        mol_type = protein
                        organism = synthetic construct
SEQUENCE: 21
SYSMN                                                                      5

SEQ ID NO: 22           moltype = AA  length = 5
FEATURE                 Location/Qualifiers
REGION                  1..5
                        note = Synthetic
source                  1..5
                        mol_type = protein
                        organism = synthetic construct
SEQUENCE: 22
GYYIH                                                                      5

SEQ ID NO: 23           moltype = AA  length = 5
FEATURE                 Location/Qualifiers
REGION                  1..5
                        note = Synthetic
source                  1..5
                        mol_type = protein
                        organism = synthetic construct
SEQUENCE: 23
SYAMH                                                                      5
```

| | | |
|---|---|---|
| SEQ ID NO: 24<br>FEATURE<br>REGION<br><br>source | moltype = AA   length = 5<br>Location/Qualifiers<br>1..5<br>note = Synthetic<br>1..5<br>mol_type = protein<br>organism = synthetic construct | |
| SEQUENCE: 24<br>NYGIT | | 5 |
| SEQ ID NO: 25<br>FEATURE<br>REGION<br><br>source | moltype = AA   length = 5<br>Location/Qualifiers<br>1..5<br>note = Synthetic<br>1..5<br>mol_type = protein<br>organism = synthetic construct | |
| SEQUENCE: 25<br>GYYMH | | 5 |
| SEQ ID NO: 26<br>FEATURE<br>REGION<br><br>source | moltype = AA   length = 5<br>Location/Qualifiers<br>1..5<br>note = Synthetic<br>1..5<br>mol_type = protein<br>organism = synthetic construct | |
| SEQUENCE: 26<br>NYYIH | | 5 |
| SEQ ID NO: 27<br>FEATURE<br>REGION<br><br>source | moltype = AA   length = 5<br>Location/Qualifiers<br>1..5<br>note = Synthetic<br>1..5<br>mol_type = protein<br>organism = synthetic construct | |
| SEQUENCE: 27<br>DYGMY | | 5 |
| SEQ ID NO: 28<br>FEATURE<br>REGION<br><br>source | moltype = AA   length = 5<br>Location/Qualifiers<br>1..5<br>note = Synthetic<br>1..5<br>mol_type = protein<br>organism = synthetic construct | |
| SEQUENCE: 28<br>SYGIN | | 5 |
| SEQ ID NO: 29<br>FEATURE<br>REGION<br><br>source | moltype = AA   length = 5<br>Location/Qualifiers<br>1..5<br>note = Synthetic<br>1..5<br>mol_type = protein<br>organism = synthetic construct | |
| SEQUENCE: 29<br>SYGIS | | 5 |
| SEQ ID NO: 30<br>FEATURE<br>REGION<br><br>source | moltype = AA   length = 5<br>Location/Qualifiers<br>1..5<br>note = Synthetic<br>1..5<br>mol_type = protein<br>organism = synthetic construct | |
| SEQUENCE: 30<br>SYYMH | | 5 |
| SEQ ID NO: 31<br>FEATURE<br>REGION<br><br>source | moltype = AA   length = 17<br>Location/Qualifiers<br>1..17<br>note = Synthetic<br>1..17<br>mol_type = protein<br>organism = synthetic construct | |
| SEQUENCE: 31<br>WINPKSGGTN YAQKFQG | | 17 |

```
SEQ ID NO: 32          moltype = AA  length = 17
FEATURE                Location/Qualifiers
REGION                 1..17
                       note = Synthetic
source                 1..17
                       mol_type = protein
                       organism = synthetic construct
SEQUENCE: 32
IINPSGGSTS YAQKFQG                                                  17

SEQ ID NO: 33          moltype = AA  length = 17
FEATURE                Location/Qualifiers
REGION                 1..17
                       note = Synthetic
source                 1..17
                       mol_type = protein
                       organism = synthetic construct
SEQUENCE: 33
WINPNSGGAN YAQKFQG                                                  17

SEQ ID NO: 34          moltype = AA  length = 17
FEATURE                Location/Qualifiers
REGION                 1..17
                       note = Synthetic
source                 1..17
                       mol_type = protein
                       organism = synthetic construct
SEQUENCE: 34
WINPNSGATN SAQKFQG                                                  17

SEQ ID NO: 35          moltype = AA  length = 17
FEATURE                Location/Qualifiers
REGION                 1..17
                       note = Synthetic
source                 1..17
                       mol_type = protein
                       organism = synthetic construct
SEQUENCE: 35
IIHPNGGSTS YAQKFQG                                                  17

SEQ ID NO: 36          moltype = AA  length = 17
FEATURE                Location/Qualifiers
REGION                 1..17
                       note = Synthetic
source                 1..17
                       mol_type = protein
                       organism = synthetic construct
SEQUENCE: 36
DISGSGRSTY YADSVKG                                                  17

SEQ ID NO: 37          moltype = AA  length = 17
FEATURE                Location/Qualifiers
REGION                 1..17
                       note = Synthetic
source                 1..17
                       mol_type = protein
                       organism = synthetic construct
SEQUENCE: 37
AISGSGGSTY YADSVKG                                                  17

SEQ ID NO: 38          moltype = AA  length = 17
FEATURE                Location/Qualifiers
REGION                 1..17
                       note = Synthetic
source                 1..17
                       mol_type = protein
                       organism = synthetic construct
SEQUENCE: 38
WMNPNSGNTG YAQKFQG                                                  17

SEQ ID NO: 39          moltype = AA  length = 17
FEATURE                Location/Qualifiers
REGION                 1..17
                       note = Synthetic
source                 1..17
                       mol_type = protein
                       organism = synthetic construct
SEQUENCE: 39
```

```
ILSPSGGGTS YAPKFQG                                                    17

SEQ ID NO: 40            moltype = AA   length = 17
FEATURE                  Location/Qualifiers
REGION                   1..17
                         note = Synthetic
source                   1..17
                         mol_type = protein
                         organism = synthetic construct
SEQUENCE: 40
WMNPNNGNTG YAQKFQG                                                    17

SEQ ID NO: 41            moltype = AA   length = 17
FEATURE                  Location/Qualifiers
REGION                   1..17
                         note = Synthetic
source                   1..17
                         mol_type = protein
                         organism = synthetic construct
SEQUENCE: 41
WISPYTGNTI YAPNVQG                                                    17

SEQ ID NO: 42            moltype = AA   length = 17
FEATURE                  Location/Qualifiers
REGION                   1..17
                         note = Synthetic
source                   1..17
                         mol_type = protein
                         organism = synthetic construct
SEQUENCE: 42
WISTYNGNTN YAQKFQG                                                    17

SEQ ID NO: 43            moltype = AA   length = 17
FEATURE                  Location/Qualifiers
REGION                   1..17
                         note = Synthetic
source                   1..17
                         mol_type = protein
                         organism = synthetic construct
SEQUENCE: 43
RIIPILGIAN YAQKFQG                                                    17

SEQ ID NO: 44            moltype = AA   length = 17
FEATURE                  Location/Qualifiers
REGION                   1..17
                         note = Synthetic
source                   1..17
                         mol_type = protein
                         organism = synthetic construct
SEQUENCE: 44
LISYDGGSTY YADSVKG                                                    17

SEQ ID NO: 45            moltype = AA   length = 17
FEATURE                  Location/Qualifiers
REGION                   1..17
                         note = Synthetic
source                   1..17
                         mol_type = protein
                         organism = synthetic construct
SEQUENCE: 45
IINPSGRSTS YAQKFQG                                                    17

SEQ ID NO: 46            moltype = AA   length = 17
FEATURE                  Location/Qualifiers
REGION                   1..17
                         note = Synthetic
source                   1..17
                         mol_type = protein
                         organism = synthetic construct
SEQUENCE: 46
GIIPIFGSPN YAQKFQG                                                    17

SEQ ID NO: 47            moltype = AA   length = 16
FEATURE                  Location/Qualifiers
REGION                   1..16
                         note = Synthetic
source                   1..16
                         mol_type = protein
                         organism = synthetic construct
```

-continued

```
SEQUENCE: 47
VIYAGGSRYY ADSVKG                                                        16

SEQ ID NO: 48           moltype = AA  length = 17
FEATURE                 Location/Qualifiers
REGION                  1..17
                        note = Synthetic
source                  1..17
                        mol_type = protein
                        organism = synthetic construct
SEQUENCE: 48
TISGSGAGTW YADSVKG                                                       17

SEQ ID NO: 49           moltype = AA  length = 17
FEATURE                 Location/Qualifiers
REGION                  1..17
                        note = Synthetic
source                  1..17
                        mol_type = protein
                        organism = synthetic construct
SEQUENCE: 49
WINPNSGGTR YARNFQG                                                       17

SEQ ID NO: 50           moltype = AA  length = 16
FEATURE                 Location/Qualifiers
REGION                  1..16
                        note = Synthetic
source                  1..16
                        mol_type = protein
                        organism = synthetic construct
SEQUENCE: 50
WLNPNSGTNY AQKFQG                                                        16

SEQ ID NO: 51           moltype = AA  length = 17
FEATURE                 Location/Qualifiers
REGION                  1..17
                        note = Synthetic
source                  1..17
                        mol_type = protein
                        organism = synthetic construct
SEQUENCE: 51
IINPSGAGTN YAQKFQG                                                       17

SEQ ID NO: 52           moltype = AA  length = 17
FEATURE                 Location/Qualifiers
REGION                  1..17
                        note = Synthetic
source                  1..17
                        mol_type = protein
                        organism = synthetic construct
SEQUENCE: 52
VISYDGRIKD YADSVKG                                                       17

SEQ ID NO: 53           moltype = AA  length = 17
FEATURE                 Location/Qualifiers
REGION                  1..17
                        note = Synthetic
source                  1..17
                        mol_type = protein
                        organism = synthetic construct
SEQUENCE: 53
GISWNGGKTH YADSVKG                                                       17

SEQ ID NO: 54           moltype = AA  length = 17
FEATURE                 Location/Qualifiers
REGION                  1..17
                        note = Synthetic
source                  1..17
                        mol_type = protein
                        organism = synthetic construct
SEQUENCE: 54
GTSLDGNKNY YADSVKG                                                       17

SEQ ID NO: 55           moltype = AA  length = 17
FEATURE                 Location/Qualifiers
REGION                  1..17
                        note = Synthetic
source                  1..17
                        mol_type = protein
```

```
                           organism = synthetic construct
SEQUENCE: 55
TISGSGGTTY YADSVKG                                                          17

SEQ ID NO: 56              moltype = AA  length = 17
FEATURE                    Location/Qualifiers
REGION                     1..17
                           note = Synthetic
source                     1..17
                           mol_type = protein
                           organism = synthetic construct
SEQUENCE: 56
WINPHSGGTN YAQKFQG                                                          17

SEQ ID NO: 57              moltype = AA  length = 17
FEATURE                    Location/Qualifiers
REGION                     1..17
                           note = Synthetic
source                     1..17
                           mol_type = protein
                           organism = synthetic construct
SEQUENCE: 57
LIDPSPGTTY YAQKFQG                                                          17

SEQ ID NO: 58              moltype = AA  length = 17
FEATURE                    Location/Qualifiers
REGION                     1..17
                           note = Synthetic
source                     1..17
                           mol_type = protein
                           organism = synthetic construct
SEQUENCE: 58
RINPNSGGTN FAQKFQG                                                          17

SEQ ID NO: 59              moltype = AA  length = 17
FEATURE                    Location/Qualifiers
REGION                     1..17
                           note = Synthetic
source                     1..17
                           mol_type = protein
                           organism = synthetic construct
SEQUENCE: 59
WMNPNSANTG YAQKFQG                                                          17

SEQ ID NO: 60              moltype = AA  length = 17
FEATURE                    Location/Qualifiers
REGION                     1..17
                           note = Synthetic
source                     1..17
                           mol_type = protein
                           organism = synthetic construct
SEQUENCE: 60
VINPSGGGTT YAKKFQG                                                          17

SEQ ID NO: 61              moltype = AA  length = 17
FEATURE                    Location/Qualifiers
REGION                     1..17
                           note = Synthetic
source                     1..17
                           mol_type = protein
                           organism = synthetic construct
SEQUENCE: 61
WINPDSGDTN FAQKFQG                                                          17

SEQ ID NO: 62              moltype = AA  length = 17
FEATURE                    Location/Qualifiers
REGION                     1..17
                           note = Synthetic
source                     1..17
                           mol_type = protein
                           organism = synthetic construct
SEQUENCE: 62
YISSSGSTIY YADSVKG                                                          17

SEQ ID NO: 63              moltype = AA  length = 17
FEATURE                    Location/Qualifiers
REGION                     1..17
                           note = Synthetic
source                     1..17
```

```
                            mol_type = protein
                            organism = synthetic construct
SEQUENCE: 63
RIIPIFGAAN YAQKFQG                                                       17

SEQ ID NO: 64               moltype = AA   length = 17
FEATURE                     Location/Qualifiers
REGION                      1..17
                            note = Synthetic
source                      1..17
                            mol_type = protein
                            organism = synthetic construct
SEQUENCE: 64
WINPNNGGTN YAQKFQG                                                       17

SEQ ID NO: 65               moltype = AA   length = 19
FEATURE                     Location/Qualifiers
REGION                      1..19
                            note = Synthetic
source                      1..19
                            mol_type = protein
                            organism = synthetic construct
SEQUENCE: 65
GTYLRTGSSL SGYYYGMDV                                                     19

SEQ ID NO: 66               moltype = AA   length = 12
FEATURE                     Location/Qualifiers
REGION                      1..12
                            note = Synthetic
source                      1..12
                            mol_type = protein
                            organism = synthetic construct
SEQUENCE: 66
SHYGDLNGGF DL                                                            12

SEQ ID NO: 67               moltype = AA   length = 12
FEATURE                     Location/Qualifiers
REGION                      1..12
                            note = Synthetic
source                      1..12
                            mol_type = protein
                            organism = synthetic construct
SEQUENCE: 67
GVVAARYYYM DV                                                            12

SEQ ID NO: 68               moltype = AA   length = 17
FEATURE                     Location/Qualifiers
REGION                      1..17
                            note = Synthetic
source                      1..17
                            mol_type = protein
                            organism = synthetic construct
SEQUENCE: 68
AGYSSSWDGY YYYGMDV                                                       17

SEQ ID NO: 69               moltype = AA   length = 12
FEATURE                     Location/Qualifiers
REGION                      1..12
                            note = Synthetic
source                      1..12
                            mol_type = protein
                            organism = synthetic construct
SEQUENCE: 69
DQAGTGGHGM DV                                                            12

SEQ ID NO: 70               moltype = AA   length = 19
FEATURE                     Location/Qualifiers
REGION                      1..19
                            note = Synthetic
source                      1..19
                            mol_type = protein
                            organism = synthetic construct
SEQUENCE: 70
GRYLEWVLSS EDYYFGMDV                                                     19

SEQ ID NO: 71               moltype = AA   length = 14
FEATURE                     Location/Qualifiers
REGION                      1..14
                            note = Synthetic
```

```
source                  1..14
                        mol_type = protein
                        organism = synthetic construct
SEQUENCE: 71
GRYSRSWERW YFDL                                                              14

SEQ ID NO: 72           moltype = AA  length = 13
FEATURE                 Location/Qualifiers
REGION                  1..13
                        note = Synthetic
source                  1..13
                        mol_type = protein
                        organism = synthetic construct
SEQUENCE: 72
GQYDSSGYYY FDY                                                               13

SEQ ID NO: 73           moltype = AA  length = 13
FEATURE                 Location/Qualifiers
REGION                  1..13
                        note = Synthetic
source                  1..13
                        mol_type = protein
                        organism = synthetic construct
SEQUENCE: 73
ATYYDFWSGS LDY                                                               13

SEQ ID NO: 74           moltype = AA  length = 10
FEATURE                 Location/Qualifiers
REGION                  1..10
                        note = Synthetic
source                  1..10
                        mol_type = protein
                        organism = synthetic construct
SEQUENCE: 74
QAGYSSGWDY                                                                   10

SEQ ID NO: 75           moltype = AA  length = 14
FEATURE                 Location/Qualifiers
REGION                  1..14
                        note = Synthetic
source                  1..14
                        mol_type = protein
                        organism = synthetic construct
SEQUENCE: 75
AVYDILTGAY YFDY                                                              14

SEQ ID NO: 76           moltype = AA  length = 12
FEATURE                 Location/Qualifiers
REGION                  1..12
                        note = Synthetic
source                  1..12
                        mol_type = protein
                        organism = synthetic construct
SEQUENCE: 76
GRLPPYYYGM DV                                                                12

SEQ ID NO: 77           moltype = AA  length = 14
FEATURE                 Location/Qualifiers
REGION                  1..14
                        note = Synthetic
source                  1..14
                        mol_type = protein
                        organism = synthetic construct
SEQUENCE: 77
MATVTKHTYW YFDL                                                              14

SEQ ID NO: 78           moltype = AA  length = 15
FEATURE                 Location/Qualifiers
REGION                  1..15
                        note = Synthetic
source                  1..15
                        mol_type = protein
                        organism = synthetic construct
SEQUENCE: 78
AGRSTSRYYY YYMDV                                                             15

SEQ ID NO: 79           moltype = AA  length = 12
FEATURE                 Location/Qualifiers
REGION                  1..12
```

```
                        note = Synthetic
source                  1..12
                        mol_type = protein
                        organism = synthetic construct
SEQUENCE: 79
SSSGYTTDAF DI                                                              12

SEQ ID NO: 80           moltype = AA  length = 11
FEATURE                 Location/Qualifiers
REGION                  1..11
                        note = Synthetic
source                  1..11
                        mol_type = protein
                        organism = synthetic construct
SEQUENCE: 80
EYQLMNVGMD V                                                               11

SEQ ID NO: 81           moltype = AA  length = 10
FEATURE                 Location/Qualifiers
REGION                  1..10
                        note = Synthetic
source                  1..10
                        mol_type = protein
                        organism = synthetic construct
SEQUENCE: 81
GKQRADAFDI                                                                 10

SEQ ID NO: 82           moltype = AA  length = 15
FEATURE                 Location/Qualifiers
REGION                  1..15
                        note = Synthetic
source                  1..15
                        mol_type = protein
                        organism = synthetic construct
SEQUENCE: 82
DVDPSRQSYY HGVDV                                                           15

SEQ ID NO: 83           moltype = AA  length = 16
FEATURE                 Location/Qualifiers
REGION                  1..16
                        note = Synthetic
source                  1..16
                        mol_type = protein
                        organism = synthetic construct
SEQUENCE: 83
GRYYYGSGSQ YHAFDI                                                          16

SEQ ID NO: 84           moltype = AA  length = 13
FEATURE                 Location/Qualifiers
REGION                  1..13
                        note = Synthetic
source                  1..13
                        mol_type = protein
                        organism = synthetic construct
SEQUENCE: 84
GRYDSSGYYY FDY                                                             13

SEQ ID NO: 85           moltype = AA  length = 13
FEATURE                 Location/Qualifiers
REGION                  1..13
                        note = Synthetic
source                  1..13
                        mol_type = protein
                        organism = synthetic construct
SEQUENCE: 85
TVTTPYQYYG MDV                                                             13

SEQ ID NO: 86           moltype = AA  length = 10
FEATURE                 Location/Qualifiers
REGION                  1..10
                        note = Synthetic
source                  1..10
                        mol_type = protein
                        organism = synthetic construct
SEQUENCE: 86
VRGFSFWFDP                                                                 10

SEQ ID NO: 87           moltype = AA  length = 7
FEATURE                 Location/Qualifiers
```

```
REGION                    1..7
                          note = Synthetic
source                    1..7
                          mol_type = protein
                          organism = synthetic construct
SEQUENCE: 87
GGGYFDY                                                                    7

SEQ ID NO: 88             moltype = AA  length = 19
FEATURE                   Location/Qualifiers
REGION                    1..19
                          note = Synthetic
source                    1..19
                          mol_type = protein
                          organism = synthetic construct
SEQUENCE: 88
GRYGSSGWSP GYYYYYMDV                                                      19

SEQ ID NO: 89             moltype = AA  length = 12
FEATURE                   Location/Qualifiers
REGION                    1..12
                          note = Synthetic
source                    1..12
                          mol_type = protein
                          organism = synthetic construct
SEQUENCE: 89
ARDSGSPKDF DY                                                             12

SEQ ID NO: 90             moltype = AA  length = 7
FEATURE                   Location/Qualifiers
REGION                    1..7
                          note = Synthetic
source                    1..7
                          mol_type = protein
                          organism = synthetic construct
SEQUENCE: 90
GTMARGS                                                                    7

SEQ ID NO: 91             moltype = AA  length = 9
FEATURE                   Location/Qualifiers
REGION                    1..9
                          note = Synthetic
source                    1..9
                          mol_type = protein
                          organism = synthetic construct
SEQUENCE: 91
ATDYPGMDV                                                                  9

SEQ ID NO: 92             moltype = AA  length = 18
FEATURE                   Location/Qualifiers
REGION                    1..18
                          note = Synthetic
source                    1..18
                          mol_type = protein
                          organism = synthetic construct
SEQUENCE: 92
GRMHYDSSVH YYYYGMDV                                                       18

SEQ ID NO: 93             moltype = AA  length = 16
FEATURE                   Location/Qualifiers
REGION                    1..16
                          note = Synthetic
source                    1..16
                          mol_type = protein
                          organism = synthetic construct
SEQUENCE: 93
VSIVGATPDY YYGMDV                                                         16

SEQ ID NO: 94             moltype = AA  length = 9
FEATURE                   Location/Qualifiers
REGION                    1..9
                          note = Synthetic
source                    1..9
                          mol_type = protein
                          organism = synthetic construct
SEQUENCE: 94
VIRGGKFDP                                                                  9

SEQ ID NO: 95             moltype = AA  length = 16
```

```
FEATURE                 Location/Qualifiers
REGION                  1..16
                        note = Synthetic
source                  1..16
                        mol_type = protein
                        organism = synthetic construct
SEQUENCE: 95
GLYAAAGDQY YYGMDV                                                       16

SEQ ID NO: 96           moltype = AA  length = 6
FEATURE                 Location/Qualifiers
REGION                  1..6
                        note = Synthetic
source                  1..6
                        mol_type = protein
                        organism = synthetic construct
SEQUENCE: 96
GAAFDY                                                                   6

SEQ ID NO: 97           moltype = AA  length = 14
FEATURE                 Location/Qualifiers
REGION                  1..14
                        note = Synthetic
source                  1..14
                        mol_type = protein
                        organism = synthetic construct
SEQUENCE: 97
EYGDYGYYYY GMDV                                                         14

SEQ ID NO: 98           moltype = AA  length = 18
FEATURE                 Location/Qualifiers
REGION                  1..18
                        note = Synthetic
source                  1..18
                        mol_type = protein
                        organism = synthetic construct
SEQUENCE: 98
GIYYYDSSGG SYYYGMDV                                                     18

SEQ ID NO: 99           moltype = AA  length = 13
FEATURE                 Location/Qualifiers
REGION                  1..13
                        note = Synthetic
source                  1..13
                        mol_type = protein
                        organism = synthetic construct
SEQUENCE: 99
ELSSSWYSYG MDV                                                          13

SEQ ID NO: 100          moltype = AA  length = 10
FEATURE                 Location/Qualifiers
REGION                  1..10
                        note = Synthetic
source                  1..10
                        mol_type = protein
                        organism = synthetic construct
SEQUENCE: 100
VSGGSWYDRL                                                              10

SEQ ID NO: 101          moltype = AA  length = 10
FEATURE                 Location/Qualifiers
REGION                  1..10
                        note = Synthetic
source                  1..10
                        mol_type = protein
                        organism = synthetic construct
SEQUENCE: 101
TYFDWFFFDY                                                              10

SEQ ID NO: 102          moltype = AA  length = 16
FEATURE                 Location/Qualifiers
REGION                  1..16
                        note = Synthetic
source                  1..16
                        mol_type = protein
                        organism = synthetic construct
SEQUENCE: 102
GRYSGHFGVY YYGMDV                                                       16
```

```
SEQ ID NO: 103          moltype = AA   length = 10
FEATURE                 Location/Qualifiers
REGION                  1..10
                        note = Synthetic
source                  1..10
                        mol_type = protein
                        organism = synthetic construct
SEQUENCE: 103
EPYGDYGFDY                                                                10

SEQ ID NO: 104          moltype = AA   length = 11
FEATURE                 Location/Qualifiers
REGION                  1..11
                        note = Synthetic
source                  1..11
                        mol_type = protein
                        organism = synthetic construct
SEQUENCE: 104
QASQDISNYL N                                                              11

SEQ ID NO: 105          moltype = AA   length = 11
FEATURE                 Location/Qualifiers
REGION                  1..11
                        note = Synthetic
source                  1..11
                        mol_type = protein
                        organism = synthetic construct
SEQUENCE: 105
RASQYISSYL A                                                              11

SEQ ID NO: 106          moltype = AA   length = 11
FEATURE                 Location/Qualifiers
REGION                  1..11
                        note = Synthetic
source                  1..11
                        mol_type = protein
                        organism = synthetic construct
SEQUENCE: 106
RASQNIGSYL N                                                              11

SEQ ID NO: 107          moltype = AA   length = 11
FEATURE                 Location/Qualifiers
REGION                  1..11
                        note = Synthetic
source                  1..11
                        mol_type = protein
                        organism = synthetic construct
SEQUENCE: 107
RASQSISSHL N                                                              11

SEQ ID NO: 108          moltype = AA   length = 11
FEATURE                 Location/Qualifiers
REGION                  1..11
                        note = Synthetic
source                  1..11
                        mol_type = protein
                        organism = synthetic construct
SEQUENCE: 108
RASQSINNWL A                                                              11

SEQ ID NO: 109          moltype = AA   length = 11
FEATURE                 Location/Qualifiers
REGION                  1..11
                        note = Synthetic
source                  1..11
                        mol_type = protein
                        organism = synthetic construct
SEQUENCE: 109
QASQDIRNYL N                                                              11

SEQ ID NO: 110          moltype = AA   length = 11
FEATURE                 Location/Qualifiers
REGION                  1..11
                        note = Synthetic
source                  1..11
                        mol_type = protein
                        organism = synthetic construct
SEQUENCE: 110
RASQSISSYL N                                                              11
```

-continued

```
SEQ ID NO: 111           moltype = AA   length = 17
FEATURE                  Location/Qualifiers
REGION                   1..17
                         note = Synthetic
source                   1..17
                         mol_type = protein
                         organism = synthetic construct
SEQUENCE: 111
KSSQSVLYSS NNKNYLA                                                         17

SEQ ID NO: 112           moltype = AA   length = 11
FEATURE                  Location/Qualifiers
REGION                   1..11
                         note = Synthetic
source                   1..11
                         mol_type = protein
                         organism = synthetic construct
SEQUENCE: 112
RASENIGNWL A                                                               11

SEQ ID NO: 113           moltype = AA   length = 11
FEATURE                  Location/Qualifiers
REGION                   1..11
                         note = Synthetic
source                   1..11
                         mol_type = protein
                         organism = synthetic construct
SEQUENCE: 113
RASQSVSSNL A                                                               11

SEQ ID NO: 114           moltype = AA   length = 11
FEATURE                  Location/Qualifiers
REGION                   1..11
                         note = Synthetic
source                   1..11
                         mol_type = protein
                         organism = synthetic construct
SEQUENCE: 114
RASQGISNNL N                                                               11

SEQ ID NO: 115           moltype = AA   length = 11
FEATURE                  Location/Qualifiers
REGION                   1..11
                         note = Synthetic
source                   1..11
                         mol_type = protein
                         organism = synthetic construct
SEQUENCE: 115
RASQSISKFL N                                                               11

SEQ ID NO: 116           moltype = AA   length = 16
FEATURE                  Location/Qualifiers
REGION                   1..16
                         note = Synthetic
source                   1..16
                         mol_type = protein
                         organism = synthetic construct
SEQUENCE: 116
RSSQSLLHSN GYNYLD                                                          16

SEQ ID NO: 117           moltype = AA   length = 11
FEATURE                  Location/Qualifiers
REGION                   1..11
                         note = Synthetic
source                   1..11
                         mol_type = protein
                         organism = synthetic construct
SEQUENCE: 117
RASQSIGSYL N                                                               11

SEQ ID NO: 118           moltype = AA   length = 11
FEATURE                  Location/Qualifiers
REGION                   1..11
                         note = Synthetic
source                   1..11
                         mol_type = protein
                         organism = synthetic construct
SEQUENCE: 118
```

QASQEIGNYL N 11

SEQ ID NO: 119     moltype = AA   length = 11
FEATURE            Location/Qualifiers
REGION             1..11
                   note = Synthetic
source             1..11
                   mol_type = protein
                   organism = synthetic construct
SEQUENCE: 119
QASQDITNFL N 11

SEQ ID NO: 120     moltype = AA   length = 11
FEATURE            Location/Qualifiers
REGION             1..11
                   note = Synthetic
source             1..11
                   mol_type = protein
                   organism = synthetic construct
SEQUENCE: 120
RASQSISTFL N 11

SEQ ID NO: 121     moltype = AA   length = 11
FEATURE            Location/Qualifiers
REGION             1..11
                   note = Synthetic
source             1..11
                   mol_type = protein
                   organism = synthetic construct
SEQUENCE: 121
QASQDISKYL N 11

SEQ ID NO: 122     moltype = AA   length = 11
FEATURE            Location/Qualifiers
REGION             1..11
                   note = Synthetic
source             1..11
                   mol_type = protein
                   organism = synthetic construct
SEQUENCE: 122
QASQDIGNYL N 11

SEQ ID NO: 123     moltype = AA   length = 11
FEATURE            Location/Qualifiers
REGION             1..11
                   note = Synthetic
source             1..11
                   mol_type = protein
                   organism = synthetic construct
SEQUENCE: 123
RASQDIRNYL A 11

SEQ ID NO: 124     moltype = AA   length = 11
FEATURE            Location/Qualifiers
REGION             1..11
                   note = Synthetic
source             1..11
                   mol_type = protein
                   organism = synthetic construct
SEQUENCE: 124
RASQSISRHL N 11

SEQ ID NO: 125     moltype = AA   length = 11
FEATURE            Location/Qualifiers
REGION             1..11
                   note = Synthetic
source             1..11
                   mol_type = protein
                   organism = synthetic construct
SEQUENCE: 125
RASQTVRSYL N 11

SEQ ID NO: 126     moltype = AA   length = 7
FEATURE            Location/Qualifiers
REGION             1..7
                   note = Synthetic
source             1..7
                   mol_type = protein
                   organism = synthetic construct

```
SEQUENCE: 126
AASSLQS                                                                                    7

SEQ ID NO: 127           moltype = AA  length = 7
FEATURE                  Location/Qualifiers
REGION                   1..7
                         note = Synthetic
source                   1..7
                         mol_type = protein
                         organism = synthetic construct
SEQUENCE: 127
AASTLQS                                                                                    7

SEQ ID NO: 128           moltype = AA  length = 7
FEATURE                  Location/Qualifiers
REGION                   1..7
                         note = Synthetic
source                   1..7
                         mol_type = protein
                         organism = synthetic construct
SEQUENCE: 128
AASSLHP                                                                                    7

SEQ ID NO: 129           moltype = AA  length = 7
FEATURE                  Location/Qualifiers
REGION                   1..7
                         note = Synthetic
source                   1..7
                         mol_type = protein
                         organism = synthetic construct
SEQUENCE: 129
AASNLES                                                                                    7

SEQ ID NO: 130           moltype = AA  length = 7
FEATURE                  Location/Qualifiers
REGION                   1..7
                         note = Synthetic
source                   1..7
                         mol_type = protein
                         organism = synthetic construct
SEQUENCE: 130
AAFNLQG                                                                                    7

SEQ ID NO: 131           moltype = AA  length = 7
FEATURE                  Location/Qualifiers
REGION                   1..7
                         note = Synthetic
source                   1..7
                         mol_type = protein
                         organism = synthetic construct
SEQUENCE: 131
GASTLES                                                                                    7

SEQ ID NO: 132           moltype = AA  length = 7
FEATURE                  Location/Qualifiers
REGION                   1..7
                         note = Synthetic
source                   1..7
                         mol_type = protein
                         organism = synthetic construct
SEQUENCE: 132
WASTRES                                                                                    7

SEQ ID NO: 133           moltype = AA  length = 7
FEATURE                  Location/Qualifiers
REGION                   1..7
                         note = Synthetic
source                   1..7
                         mol_type = protein
                         organism = synthetic construct
SEQUENCE: 133
ATSTLQS                                                                                    7

SEQ ID NO: 134           moltype = AA  length = 7
FEATURE                  Location/Qualifiers
REGION                   1..7
                         note = Synthetic
source                   1..7
                         mol_type = protein
```

```
                         organism = synthetic construct
SEQUENCE: 134
GASTRAT                                                                     7

SEQ ID NO: 135           moltype = AA   length = 7
FEATURE                  Location/Qualifiers
REGION                   1..7
                         note = Synthetic
source                   1..7
                         mol_type = protein
                         organism = synthetic construct
SEQUENCE: 135
AASILQS                                                                     7

SEQ ID NO: 136           moltype = AA   length = 7
FEATURE                  Location/Qualifiers
REGION                   1..7
                         note = Synthetic
source                   1..7
                         mol_type = protein
                         organism = synthetic construct
SEQUENCE: 136
SASNLQS                                                                     7

SEQ ID NO: 137           moltype = AA   length = 7
FEATURE                  Location/Qualifiers
REGION                   1..7
                         note = Synthetic
source                   1..7
                         mol_type = protein
                         organism = synthetic construct
SEQUENCE: 137
LGSNRAS                                                                     7

SEQ ID NO: 138           moltype = AA   length = 7
FEATURE                  Location/Qualifiers
REGION                   1..7
                         note = Synthetic
source                   1..7
                         mol_type = protein
                         organism = synthetic construct
SEQUENCE: 138
AASRLQS                                                                     7

SEQ ID NO: 139           moltype = AA   length = 7
FEATURE                  Location/Qualifiers
REGION                   1..7
                         note = Synthetic
source                   1..7
                         mol_type = protein
                         organism = synthetic construct
SEQUENCE: 139
GASSLQS                                                                     7

SEQ ID NO: 140           moltype = AA   length = 7
FEATURE                  Location/Qualifiers
REGION                   1..7
                         note = Synthetic
source                   1..7
                         mol_type = protein
                         organism = synthetic construct
SEQUENCE: 140
LASSLQS                                                                     7

SEQ ID NO: 141           moltype = AA   length = 7
FEATURE                  Location/Qualifiers
REGION                   1..7
                         note = Synthetic
source                   1..7
                         mol_type = protein
                         organism = synthetic construct
SEQUENCE: 141
KASSLES                                                                     7

SEQ ID NO: 142           moltype = AA   length = 7
FEATURE                  Location/Qualifiers
REGION                   1..7
                         note = Synthetic
source                   1..7
```

```
                        mol_type = protein
                        organism = synthetic construct
SEQUENCE: 142
AASSLQT                                                             7

SEQ ID NO: 143          moltype = AA  length = 7
FEATURE                 Location/Qualifiers
REGION                  1..7
                        note = Synthetic
source                  1..7
                        mol_type = protein
                        organism = synthetic construct
SEQUENCE: 143
AASNLQK                                                             7

SEQ ID NO: 144          moltype = AA  length = 7
FEATURE                 Location/Qualifiers
REGION                  1..7
                        note = Synthetic
source                  1..7
                        mol_type = protein
                        organism = synthetic construct
SEQUENCE: 144
DTSNLET                                                             7

SEQ ID NO: 145          moltype = AA  length = 7
FEATURE                 Location/Qualifiers
REGION                  1..7
                        note = Synthetic
source                  1..7
                        mol_type = protein
                        organism = synthetic construct
SEQUENCE: 145
WASFRES                                                             7

SEQ ID NO: 146          moltype = AA  length = 7
FEATURE                 Location/Qualifiers
REGION                  1..7
                        note = Synthetic
source                  1..7
                        mol_type = protein
                        organism = synthetic construct
SEQUENCE: 146
WASARES                                                             7

SEQ ID NO: 147          moltype = AA  length = 7
FEATURE                 Location/Qualifiers
REGION                  1..7
                        note = Synthetic
source                  1..7
                        mol_type = protein
                        organism = synthetic construct
SEQUENCE: 147
WASIRES                                                             7

SEQ ID NO: 148          moltype = AA  length = 7
FEATURE                 Location/Qualifiers
REGION                  1..7
                        note = Synthetic
source                  1..7
                        mol_type = protein
                        organism = synthetic construct
SEQUENCE: 148
DASNLHA                                                             7

SEQ ID NO: 149          moltype = AA  length = 9
FEATURE                 Location/Qualifiers
REGION                  1..9
                        note = Synthetic
source                  1..9
                        mol_type = protein
                        organism = synthetic construct
SEQUENCE: 149
QQTDSIPIT                                                           9

SEQ ID NO: 150          moltype = AA  length = 9
FEATURE                 Location/Qualifiers
REGION                  1..9
                        note = Synthetic
```

```
source                    1..9
                          mol_type = protein
                          organism = synthetic construct
SEQUENCE: 150
QQSYSTPLT                                                              9

SEQ ID NO: 151            moltype = AA  length = 9
FEATURE                   Location/Qualifiers
REGION                    1..9
                          note = Synthetic
source                    1..9
                          mol_type = protein
                          organism = synthetic construct
SEQUENCE: 151
QQTNSFPLT                                                              9

SEQ ID NO: 152            moltype = AA  length = 9
FEATURE                   Location/Qualifiers
REGION                    1..9
                          note = Synthetic
source                    1..9
                          mol_type = protein
                          organism = synthetic construct
SEQUENCE: 152
EQNYRLPIT                                                              9

SEQ ID NO: 153            moltype = AA  length = 9
FEATURE                   Location/Qualifiers
REGION                    1..9
                          note = Synthetic
source                    1..9
                          mol_type = protein
                          organism = synthetic construct
SEQUENCE: 153
QQSDSFPLT                                                              9

SEQ ID NO: 154            moltype = AA  length = 9
FEATURE                   Location/Qualifiers
REGION                    1..9
                          note = Synthetic
source                    1..9
                          mol_type = protein
                          organism = synthetic construct
SEQUENCE: 154
QQTNSFPIT                                                              9

SEQ ID NO: 155            moltype = AA  length = 9
FEATURE                   Location/Qualifiers
REGION                    1..9
                          note = Synthetic
source                    1..9
                          mol_type = protein
                          organism = synthetic construct
SEQUENCE: 155
QQSYSFPLT                                                              9

SEQ ID NO: 156            moltype = AA  length = 9
FEATURE                   Location/Qualifiers
REGION                    1..9
                          note = Synthetic
source                    1..9
                          mol_type = protein
                          organism = synthetic construct
SEQUENCE: 156
QQAHSFPLT                                                              9

SEQ ID NO: 157            moltype = AA  length = 9
FEATURE                   Location/Qualifiers
REGION                    1..9
                          note = Synthetic
source                    1..9
                          mol_type = protein
                          organism = synthetic construct
SEQUENCE: 157
QQSYSTPIT                                                              9

SEQ ID NO: 158            moltype = AA  length = 9
FEATURE                   Location/Qualifiers
REGION                    1..9
```

```
                        note = Synthetic
source                  1..9
                        mol_type = protein
                        organism = synthetic construct
SEQUENCE: 158
QQYYSTPLT                                                                         9

SEQ ID NO: 159          moltype = AA  length = 9
FEATURE                 Location/Qualifiers
REGION                  1..9
                        note = Synthetic
source                  1..9
                        mol_type = protein
                        organism = synthetic construct
SEQUENCE: 159
QQANSLPYS                                                                         9

SEQ ID NO: 160          moltype = AA  length = 9
FEATURE                 Location/Qualifiers
REGION                  1..9
                        note = Synthetic
source                  1..9
                        mol_type = protein
                        organism = synthetic construct
SEQUENCE: 160
QQGYSTPYT                                                                         9

SEQ ID NO: 161          moltype = AA  length = 9
FEATURE                 Location/Qualifiers
REGION                  1..9
                        note = Synthetic
source                  1..9
                        mol_type = protein
                        organism = synthetic construct
SEQUENCE: 161
QQYGTSPFT                                                                         9

SEQ ID NO: 162          moltype = AA  length = 9
FEATURE                 Location/Qualifiers
REGION                  1..9
                        note = Synthetic
source                  1..9
                        mol_type = protein
                        organism = synthetic construct
SEQUENCE: 162
QQSYTTTLT                                                                         9

SEQ ID NO: 163          moltype = AA  length = 9
FEATURE                 Location/Qualifiers
REGION                  1..9
                        note = Synthetic
source                  1..9
                        mol_type = protein
                        organism = synthetic construct
SEQUENCE: 163
QQANSFPLT                                                                         9

SEQ ID NO: 164          moltype = AA  length = 9
FEATURE                 Location/Qualifiers
REGION                  1..9
                        note = Synthetic
source                  1..9
                        mol_type = protein
                        organism = synthetic construct
SEQUENCE: 164
MQGAHWPYT                                                                         9

SEQ ID NO: 165          moltype = AA  length = 9
FEATURE                 Location/Qualifiers
REGION                  1..9
                        note = Synthetic
source                  1..9
                        mol_type = protein
                        organism = synthetic construct
SEQUENCE: 165
MQALQTPLT                                                                         9

SEQ ID NO: 166          moltype = AA  length = 9
FEATURE                 Location/Qualifiers
```

```
REGION                    1..9
                          note = Synthetic
source                    1..9
                          mol_type = protein
                          organism = synthetic construct
SEQUENCE: 166
QQSYGIPLT                                                                           9

SEQ ID NO: 167            moltype = AA  length = 9
FEATURE                   Location/Qualifiers
REGION                    1..9
                          note = Synthetic
source                    1..9
                          mol_type = protein
                          organism = synthetic construct
SEQUENCE: 167
QQANTFPLT                                                                           9

SEQ ID NO: 168            moltype = AA  length = 9
FEATURE                   Location/Qualifiers
REGION                    1..9
                          note = Synthetic
source                    1..9
                          mol_type = protein
                          organism = synthetic construct
SEQUENCE: 168
QQTYSFPLT                                                                           9

SEQ ID NO: 169            moltype = AA  length = 8
FEATURE                   Location/Qualifiers
REGION                    1..8
                          note = Synthetic
source                    1..8
                          mol_type = protein
                          organism = synthetic construct
SEQUENCE: 169
QQSYSTPP                                                                            8

SEQ ID NO: 170            moltype = AA  length = 9
FEATURE                   Location/Qualifiers
REGION                    1..9
                          note = Synthetic
source                    1..9
                          mol_type = protein
                          organism = synthetic construct
SEQUENCE: 170
QQANSFPRT                                                                           9

SEQ ID NO: 171            moltype = AA  length = 9
FEATURE                   Location/Qualifiers
REGION                    1..9
                          note = Synthetic
source                    1..9
                          mol_type = protein
                          organism = synthetic construct
SEQUENCE: 171
LQHNSFPPT                                                                           9

SEQ ID NO: 172            moltype = AA  length = 9
FEATURE                   Location/Qualifiers
REGION                    1..9
                          note = Synthetic
source                    1..9
                          mol_type = protein
                          organism = synthetic construct
SEQUENCE: 172
LQAISFPFT                                                                           9

SEQ ID NO: 173            moltype = AA  length = 9
FEATURE                   Location/Qualifiers
REGION                    1..9
                          note = Synthetic
source                    1..9
                          mol_type = protein
                          organism = synthetic construct
SEQUENCE: 173
QQAYSLPWT                                                                           9

SEQ ID NO: 174            moltype = AA  length = 9
```

```
                        -continued

FEATURE              Location/Qualifiers
REGION               1..9
                     note = Synthetic
source               1..9
                     mol_type = protein
                     organism = synthetic construct
SEQUENCE: 174
QQSYTTPYT                                                                        9

SEQ ID NO: 175       moltype = AA  length = 9
FEATURE              Location/Qualifiers
REGION               1..9
                     note = Synthetic
source               1..9
                     mol_type = protein
                     organism = synthetic construct
SEQUENCE: 175
QQYYTTPLT                                                                        9

SEQ ID NO: 176       moltype = AA  length = 9
FEATURE              Location/Qualifiers
REGION               1..9
                     note = Synthetic
source               1..9
                     mol_type = protein
                     organism = synthetic construct
SEQUENCE: 176
QQYKSAPYT                                                                        9

SEQ ID NO: 177       moltype = AA  length = 9
FEATURE              Location/Qualifiers
REGION               1..9
                     note = Synthetic
source               1..9
                     mol_type = protein
                     organism = synthetic construct
SEQUENCE: 177
QQSNSFPLT                                                                        9

SEQ ID NO: 178       moltype = AA  length = 9
FEATURE              Location/Qualifiers
REGION               1..9
                     note = Synthetic
source               1..9
                     mol_type = protein
                     organism = synthetic construct
SEQUENCE: 178
QQSYQTPLT                                                                        9

SEQ ID NO: 179       moltype = AA  length = 9
FEATURE              Location/Qualifiers
REGION               1..9
                     note = Synthetic
source               1..9
                     mol_type = protein
                     organism = synthetic construct
SEQUENCE: 179
QQYSSPFT                                                                         9

SEQ ID NO: 180       moltype = AA  length = 9
FEATURE              Location/Qualifiers
REGION               1..9
                     note = Synthetic
source               1..9
                     mol_type = protein
                     organism = synthetic construct
SEQUENCE: 180
MQALQAPVT                                                                        9

SEQ ID NO: 181       moltype = AA  length = 9
FEATURE              Location/Qualifiers
REGION               1..9
                     note = Synthetic
source               1..9
                     mol_type = protein
                     organism = synthetic construct
SEQUENCE: 181
QQTYRTPLT                                                                        9
```

-continued

```
SEQ ID NO: 182            moltype = AA  length = 30
FEATURE                   Location/Qualifiers
REGION                    1..30
                          note = synthetic
source                    1..30
                          mol_type = protein
                          organism = synthetic construct
SEQUENCE: 182
QVQLVQSGAE VKKPGASVKV SCKASGYTFT                                          30

SEQ ID NO: 183            moltype = AA  length = 30
FEATURE                   Location/Qualifiers
REGION                    1..30
                          note = Synthetic
source                    1..30
                          mol_type = protein
                          organism = synthetic construct
SEQUENCE: 183
QVQLVQSGAE VKKPGASVKV SCKASGYIFT                                          30

SEQ ID NO: 184            moltype = AA  length = 30
FEATURE                   Location/Qualifiers
REGION                    1..30
                          note = Synthetic
source                    1..30
                          mol_type = protein
                          organism = synthetic construct
SEQUENCE: 184
QVQLVQSGAE VKKPGASVKV SCKASGGTLN                                          30

SEQ ID NO: 185            moltype = AA  length = 30
FEATURE                   Location/Qualifiers
REGION                    1..30
                          note = Synthetic
source                    1..30
                          mol_type = protein
                          organism = synthetic construct
SEQUENCE: 185
EVQLLESGGG LVQPGGSLRL SCAASGFTFS                                          30

SEQ ID NO: 186            moltype = AA  length = 30
FEATURE                   Location/Qualifiers
REGION                    1..30
                          note = Synthetic
source                    1..30
                          mol_type = protein
                          organism = synthetic construct
SEQUENCE: 186
QVQLVQSGAE VKKPGASVKV SCKASGYTLT                                          30

SEQ ID NO: 187            moltype = AA  length = 30
FEATURE                   Location/Qualifiers
REGION                    1..30
                          note = Synthetic
source                    1..30
                          mol_type = protein
                          organism = synthetic construct
SEQUENCE: 187
QVQLVQSGAE VKKPGASVKV SCKASGGTFS                                          30

SEQ ID NO: 188            moltype = AA  length = 30
FEATURE                   Location/Qualifiers
REGION                    1..30
                          note = Synthetic
source                    1..30
                          mol_type = protein
                          organism = synthetic construct
SEQUENCE: 188
QVQLVQSGVR WRSLGPPVKV SCKASGDTFS                                          30

SEQ ID NO: 189            moltype = AA  length = 30
FEATURE                   Location/Qualifiers
REGION                    1..30
                          note = Synthetic
source                    1..30
                          mol_type = protein
                          organism = synthetic construct
SEQUENCE: 189
QVQLVQSGAE VKKPGSSVKV SCKASGYTFT                                          30
```

```
SEQ ID NO: 190          moltype = AA   length = 30
FEATURE                 Location/Qualifiers
REGION                  1..30
                        note = Synthetic
source                  1..30
                        mol_type = protein
                        organism = synthetic construct
SEQUENCE: 190
EVQLLESGGG LVQPGGSLRL SCAASGFIFS                                        30

SEQ ID NO: 191          moltype = AA   length = 30
FEATURE                 Location/Qualifiers
REGION                  1..30
                        note = Synthetic
source                  1..30
                        mol_type = protein
                        organism = synthetic construct
SEQUENCE: 191
EVQLLESGGG LVKPGGSLRL SCAASGFTFS                                        30

SEQ ID NO: 192          moltype = AA   length = 30
FEATURE                 Location/Qualifiers
REGION                  1..30
                        note = Synthetic
source                  1..30
                        mol_type = protein
                        organism = synthetic construct
SEQUENCE: 192
QVQLVQSGAE VKKPGASVKV SCKASEYTFT                                        30

SEQ ID NO: 193          moltype = AA   length = 30
FEATURE                 Location/Qualifiers
REGION                  1..30
                        note = Synthetic
source                  1..30
                        mol_type = protein
                        organism = synthetic construct
SEQUENCE: 193
QVQLVQSGAE VKKPGSSVKV SCKASGDTFT                                        30

SEQ ID NO: 194          moltype = AA   length = 30
FEATURE                 Location/Qualifiers
REGION                  1..30
                        note = Synthetic
source                  1..30
                        mol_type = protein
                        organism = synthetic construct
SEQUENCE: 194
EVQLLESGGG LVQPGGSLRL SCAASTFPFS                                        30

SEQ ID NO: 195          moltype = AA   length = 30
FEATURE                 Location/Qualifiers
REGION                  1..30
                        note = Synthetic
source                  1..30
                        mol_type = protein
                        organism = synthetic construct
SEQUENCE: 195
QVQLVQSGAE VKKPGASVKV SCKASGYSFT                                        30

SEQ ID NO: 196          moltype = AA   length = 30
FEATURE                 Location/Qualifiers
REGION                  1..30
                        note = Synthetic
source                  1..30
                        mol_type = protein
                        organism = synthetic construct
SEQUENCE: 196
QVQLVQSGAE VKKPGASVKV SCKASGGTGS                                        30

SEQ ID NO: 197          moltype = AA   length = 30
FEATURE                 Location/Qualifiers
REGION                  1..30
                        note = Synthetic
source                  1..30
                        mol_type = protein
                        organism = synthetic construct
SEQUENCE: 197
```

```
QVQLVQSGAE VKKPGASVKV SCKASGDTFS                                              30

SEQ ID NO: 198          moltype = AA  length = 30
FEATURE                 Location/Qualifiers
REGION                  1..30
                        note = Synthetic
source                  1..30
                        mol_type = protein
                        organism = synthetic construct
SEQUENCE: 198
EVQLLESGGG LVKPGGSLRL SCAASGFTLS                                              30

SEQ ID NO: 199          moltype = AA  length = 30
FEATURE                 Location/Qualifiers
REGION                  1..30
                        note = Synthetic
source                  1..30
                        mol_type = protein
                        organism = synthetic construct
SEQUENCE: 199
QVQLVQSGAE VKKPGSSVKV SCKASGYTFS                                              30

SEQ ID NO: 200          moltype = AA  length = 30
FEATURE                 Location/Qualifiers
REGION                  1..30
                        note = Synthetic
source                  1..30
                        mol_type = protein
                        organism = synthetic construct
SEQUENCE: 200
QVQLVQSGAE VKKPGASVKV SCKASGYTFS                                              30

SEQ ID NO: 201          moltype = AA  length = 14
FEATURE                 Location/Qualifiers
REGION                  1..14
                        note = Synthetic
source                  1..14
                        mol_type = protein
                        organism = synthetic construct
SEQUENCE: 201
WVRQAPGQGL EWMG                                                               14

SEQ ID NO: 202          moltype = AA  length = 14
FEATURE                 Location/Qualifiers
REGION                  1..14
                        note = Synthetic
source                  1..14
                        mol_type = protein
                        organism = synthetic construct
SEQUENCE: 202
WVRQAPGQGL EWLG                                                               14

SEQ ID NO: 203          moltype = AA  length = 14
FEATURE                 Location/Qualifiers
REGION                  1..14
                        note = Synthetic
source                  1..14
                        mol_type = protein
                        organism = synthetic construct
SEQUENCE: 203
WVRQAPGKGL EWVS                                                               14

SEQ ID NO: 204          moltype = AA  length = 14
FEATURE                 Location/Qualifiers
REGION                  1..14
                        note = Synthetic
source                  1..14
                        mol_type = protein
                        organism = synthetic construct
SEQUENCE: 204
WVRQAPGKGL EWVA                                                               14

SEQ ID NO: 205          moltype = AA  length = 14
FEATURE                 Location/Qualifiers
REGION                  1..14
                        note = Synthetic
source                  1..14
                        mol_type = protein
                        organism = synthetic construct
```

```
SEQUENCE: 205
WVRQAPGKGL EWLS                                                                 14

SEQ ID NO: 206          moltype = AA  length = 14
FEATURE                 Location/Qualifiers
REGION                  1..14
                        note = Synthetic
source                  1..14
                        mol_type = protein
                        organism = synthetic construct
SEQUENCE: 206
WVRQAPGKGL EWMG                                                                 14

SEQ ID NO: 207          moltype = AA  length = 14
FEATURE                 Location/Qualifiers
REGION                  1..14
                        note = Synthetic
source                  1..14
                        mol_type = protein
                        organism = synthetic construct
SEQUENCE: 207
WVRQAPGQGL EWMA                                                                 14

SEQ ID NO: 208          moltype = AA  length = 32
FEATURE                 Location/Qualifiers
REGION                  1..32
                        note = Synthetic
source                  1..32
                        mol_type = protein
                        organism = synthetic construct
SEQUENCE: 208
RVTMTRDTST STVYMELSSL RSEDTAVYYC AR                                             32

SEQ ID NO: 209          moltype = AA  length = 32
FEATURE                 Location/Qualifiers
REGION                  1..32
                        note = Synthetic
source                  1..32
                        mol_type = protein
                        organism = synthetic construct
SEQUENCE: 209
RFTISRDNSK NTLYLQMNSL RAEDTAVYYC AR                                             32

SEQ ID NO: 210          moltype = AA  length = 32
FEATURE                 Location/Qualifiers
REGION                  1..32
                        note = Synthetic
source                  1..32
                        mol_type = protein
                        organism = synthetic construct
SEQUENCE: 210
RVTMTRDTST STVYMELSSL RSEDTAVYYC TR                                             32

SEQ ID NO: 211          moltype = AA  length = 32
FEATURE                 Location/Qualifiers
REGION                  1..32
                        note = Synthetic
source                  1..32
                        mol_type = protein
                        organism = synthetic construct
SEQUENCE: 211
RVTITADEST STAYMELSSL RSEDTAVYYC AR                                             32

SEQ ID NO: 212          moltype = AA  length = 32
FEATURE                 Location/Qualifiers
REGION                  1..32
                        note = Synthetic
source                  1..32
                        mol_type = protein
                        organism = synthetic construct
SEQUENCE: 212
RFTISRDDSK NTLYLQMNSL KTEDTAVYYC AR                                             32

SEQ ID NO: 213          moltype = AA  length = 32
FEATURE                 Location/Qualifiers
REGION                  1..32
                        note = Synthetic
source                  1..32
                        mol_type = protein
```

```
                          organism = synthetic construct
SEQUENCE: 213
RVTITADEST STAYMELSSL RSEDTAVYYC AG                                    32

SEQ ID NO: 214            moltype = AA  length = 32
FEATURE                   Location/Qualifiers
REGION                    1..32
                          note = Synthetic
source                    1..32
                          mol_type = protein
                          organism = synthetic construct
SEQUENCE: 214
RFTISRDNSK NTLYLQNEQP GAEDTAVYYC AR                                    32

SEQ ID NO: 215            moltype = AA  length = 32
FEATURE                   Location/Qualifiers
REGION                    1..32
                          note = Synthetic
source                    1..32
                          mol_type = protein
                          organism = synthetic construct
SEQUENCE: 215
RVTITADEST STAYMELSSL RSEDTAVYYC TR                                    32

SEQ ID NO: 216            moltype = AA  length = 11
FEATURE                   Location/Qualifiers
REGION                    1..11
                          note = Synthetic
source                    1..11
                          mol_type = protein
                          organism = synthetic construct
SEQUENCE: 216
WGQGTTVTVS S                                                           11

SEQ ID NO: 217            moltype = AA  length = 11
FEATURE                   Location/Qualifiers
REGION                    1..11
                          note = Synthetic
source                    1..11
                          mol_type = protein
                          organism = synthetic construct
SEQUENCE: 217
WGRGTLVTVS S                                                           11

SEQ ID NO: 218            moltype = AA  length = 11
FEATURE                   Location/Qualifiers
REGION                    1..11
                          note = Synthetic
source                    1..11
                          mol_type = protein
                          organism = synthetic construct
SEQUENCE: 218
WGKGTTVTVS S                                                           11

SEQ ID NO: 219            moltype = AA  length = 11
FEATURE                   Location/Qualifiers
REGION                    1..11
                          note = Synthetic
source                    1..11
                          mol_type = protein
                          organism = synthetic construct
SEQUENCE: 219
WGQGTMVTVS S                                                           11

SEQ ID NO: 220            moltype = AA  length = 11
FEATURE                   Location/Qualifiers
REGION                    1..11
                          note = Synthetic
source                    1..11
                          mol_type = protein
                          organism = synthetic construct
SEQUENCE: 220
WGQGTLVTVS S                                                           11

SEQ ID NO: 221            moltype = AA  length = 11
FEATURE                   Location/Qualifiers
REGION                    1..11
                          note = Synthetic
source                    1..11
```

```
                        mol_type = protein
                        organism = synthetic construct
SEQUENCE: 221
WGKGTLVTVS S                                                            11

SEQ ID NO: 222          moltype = AA   length = 11
FEATURE                 Location/Qualifiers
REGION                  1..11
                        note = Synthetic
source                  1..11
                        mol_type = protein
                        organism = synthetic construct
SEQUENCE: 222
LGPGNPVTVS S                                                            11

SEQ ID NO: 223          moltype = AA   length = 23
FEATURE                 Location/Qualifiers
REGION                  1..23
                        note = Synthetic
source                  1..23
                        mol_type = protein
                        organism = synthetic construct
SEQUENCE: 223
DIQMTQSPSS LSASVGDRVT ITC                                               23

SEQ ID NO: 224          moltype = AA   length = 23
FEATURE                 Location/Qualifiers
REGION                  1..23
                        note = Synthetic
source                  1..23
                        mol_type = protein
                        organism = synthetic construct
SEQUENCE: 224
DIVMTQSPDS LAVSLGERAT INC                                               23

SEQ ID NO: 225          moltype = AA   length = 23
FEATURE                 Location/Qualifiers
REGION                  1..23
                        note = Synthetic
source                  1..23
                        mol_type = protein
                        organism = synthetic construct
SEQUENCE: 225
EIVMTQSPAT LSVSPGERAT LSC                                               23

SEQ ID NO: 226          moltype = AA   length = 23
FEATURE                 Location/Qualifiers
REGION                  1..23
                        note = Synthetic
source                  1..23
                        mol_type = protein
                        organism = synthetic construct
SEQUENCE: 226
DIVMTQSPLF LPVTPGEPAS ISC                                               23

SEQ ID NO: 227          moltype = AA   length = 23
FEATURE                 Location/Qualifiers
REGION                  1..23
                        note = Synthetic
source                  1..23
                        mol_type = protein
                        organism = synthetic construct
SEQUENCE: 227
DIVMTQSPLS LPVTPGEPAS ISC                                               23

SEQ ID NO: 228          moltype = AA   length = 15
FEATURE                 Location/Qualifiers
REGION                  1..15
                        note = Synthetic
source                  1..15
                        mol_type = protein
                        organism = synthetic construct
SEQUENCE: 228
WYQQKPGKAP KLLIY                                                        15

SEQ ID NO: 229          moltype = AA   length = 15
FEATURE                 Location/Qualifiers
REGION                  1..15
                        note = Synthetic
```

```
source                    1..15
                          mol_type = protein
                          organism = synthetic construct
SEQUENCE: 229
WYQQKPGQPP KLLIY                                                    15

SEQ ID NO: 230            moltype = AA  length = 15
FEATURE                   Location/Qualifiers
REGION                    1..15
                          note = Synthetic
source                    1..15
                          mol_type = protein
                          organism = synthetic construct
SEQUENCE: 230
WYQQKPGQAP RLLIY                                                    15

SEQ ID NO: 231            moltype = AA  length = 15
FEATURE                   Location/Qualifiers
REGION                    1..15
                          note = Synthetic
source                    1..15
                          mol_type = protein
                          organism = synthetic construct
SEQUENCE: 231
WYHQKPGKAP KLLIY                                                    15

SEQ ID NO: 232            moltype = AA  length = 15
FEATURE                   Location/Qualifiers
REGION                    1..15
                          note = Synthetic
source                    1..15
                          mol_type = protein
                          organism = synthetic construct
SEQUENCE: 232
WYLQKPGQSP QLLIY                                                    15

SEQ ID NO: 233            moltype = AA  length = 32
FEATURE                   Location/Qualifiers
REGION                    1..32
                          note = Synthetic
source                    1..32
                          mol_type = protein
                          organism = synthetic construct
SEQUENCE: 233
GVPSRFSGSG SGTDFTLTIS SLQPEDFATY YC                                 32

SEQ ID NO: 234            moltype = AA  length = 32
FEATURE                   Location/Qualifiers
REGION                    1..32
                          note = Synthetic
source                    1..32
                          mol_type = protein
                          organism = synthetic construct
SEQUENCE: 234
GVPDRFSGSG SGTDFTLTIS SLQAEDVAVY YC                                 32

SEQ ID NO: 235            moltype = AA  length = 32
FEATURE                   Location/Qualifiers
REGION                    1..32
                          note = Synthetic
source                    1..32
                          mol_type = protein
                          organism = synthetic construct
SEQUENCE: 235
GIPARFSGSG SGTEFTLTIS SLQSEDFAVY YC                                 32

SEQ ID NO: 236            moltype = AA  length = 32
FEATURE                   Location/Qualifiers
REGION                    1..32
                          note = Synthetic
source                    1..32
                          mol_type = protein
                          organism = synthetic construct
SEQUENCE: 236
GVPDRFSGSG SGTDFTLKIS RVEAEDVGVY YC                                 32

SEQ ID NO: 237            moltype = AA  length = 10
FEATURE                   Location/Qualifiers
REGION                    1..10
```

```
                              note = Synthetic
source                        1..10
                              mol_type = protein
                              organism = synthetic construct
SEQUENCE: 237
FGQGTKVEIK                                                                10

SEQ ID NO: 238                moltype = AA   length = 10
FEATURE                       Location/Qualifiers
REGION                        1..10
                              note = Synthetic
source                        1..10
                              mol_type = protein
                              organism = synthetic construct
SEQUENCE: 238
FGPGTKVDIK                                                                10

SEQ ID NO: 239                moltype = AA   length = 10
FEATURE                       Location/Qualifiers
REGION                        1..10
                              note = Synthetic
source                        1..10
                              mol_type = protein
                              organism = synthetic construct
SEQUENCE: 239
FGGGTKVEIK                                                                10

SEQ ID NO: 240                moltype = AA   length = 10
FEATURE                       Location/Qualifiers
REGION                        1..10
                              note = Synthetic
source                        1..10
                              mol_type = protein
                              organism = synthetic construct
SEQUENCE: 240
FGQGTRLEIK                                                                10

SEQ ID NO: 241                moltype = AA   length = 10
FEATURE                       Location/Qualifiers
REGION                        1..10
                              note = Synthetic
source                        1..10
                              mol_type = protein
                              organism = synthetic construct
SEQUENCE: 241
FGQGTKLEIK                                                                10

SEQ ID NO: 242                moltype = AA   length = 10
FEATURE                       Location/Qualifiers
REGION                        1..10
                              note = Synthetic
source                        1..10
                              mol_type = protein
                              organism = synthetic construct
SEQUENCE: 242
FGGGTKLEIK                                                                10

SEQ ID NO: 243                moltype = AA   length = 128
FEATURE                       Location/Qualifiers
REGION                        1..128
                              note = Synthetic
source                        1..128
                              mol_type = protein
                              organism = synthetic construct
SEQUENCE: 243
QVQLVQSGAE VKKPGASVKV SCKASGYTFT SYYMQWVRQA PGQGLEWMGW INPKSGGTNY          60
AQKFQGRVTM TRDTSTSTVY MELSSLRSED TAVYYCARGT YLRTGSSLSG YYYGMDWGQ          120
GTTVTVSS                                                                 128

SEQ ID NO: 244                moltype = AA   length = 121
FEATURE                       Location/Qualifiers
REGION                        1..121
                              note = Synthetic
source                        1..121
                              mol_type = protein
                              organism = synthetic construct
SEQUENCE: 244
QVQLVQSGAE VKKPGASVKV SCKASGYIFT TYYMHWVRQA PGQGLEWMGI INPSGGSTSY         60
AQKFQGRVTM TRDTSTSTVY MELSSLRSED TAVYYCARSH YGDLNGGFDL WGRGTLVTVS        120
```

```
S                                                                     121

SEQ ID NO: 245          moltype = AA  length = 121
FEATURE                 Location/Qualifiers
REGION                  1..121
                        note = Synthetic
source                  1..121
                        mol_type = protein
                        organism = synthetic construct
SEQUENCE: 245
QVQLVQSGAE VKKPGASVKV SCKASGGTLN NFGINWVRQA PGQGLEWMGW INPNSGGANY      60
AQKFQGRVTM TRDTSTSTVY MELSSLRSED TAVYYCARGV VAARYYYMDV WGKGTTVTVS      120
S                                                                     121

SEQ ID NO: 246          moltype = AA  length = 126
FEATURE                 Location/Qualifiers
REGION                  1..126
                        note = Synthetic
source                  1..126
                        mol_type = protein
                        organism = synthetic construct
SEQUENCE: 246
QVQLVQSGAE VKKPGASVKV SCKASGYTFT SYDINWVRQA PGQGLEWLGW INPNSGATNS      60
AQKFQGRVTM TRDTSTSTVY MELSSLRSED TAVYYCARAG YSSSWDGYYY YGMDVWGQGT      120
TVTVSS                                                                126

SEQ ID NO: 247          moltype = AA  length = 121
FEATURE                 Location/Qualifiers
REGION                  1..121
                        note = Synthetic
source                  1..121
                        mol_type = protein
                        organism = synthetic construct
SEQUENCE: 247
QVQLVQSGAE VKKPGASVKV SCKASGYTFT GYYVHWVRQA PGQGLEWMGI IHPNGGSTSY      60
AQKFQGRVTM TRDTSTSTVY MELSSLRSED TAVYYCARDQ AGTGGHGMDV WGQGTMVTVS      120
S                                                                     121

SEQ ID NO: 248          moltype = AA  length = 128
FEATURE                 Location/Qualifiers
REGION                  1..128
                        note = Synthetic
source                  1..128
                        mol_type = protein
                        organism = synthetic construct
SEQUENCE: 248
EVQLLESGGG LVQPGGSLRL SCAASGFTFS SYWMSWVRQA PGKGLEWVSD ISGSGRSTYY      60
ADSVKGRFTI SRDNSKNTLY LQMNSLRAED TAVYYCARGR YLEWVLSSED YYFGMDVWGQ      120
GTTVTVSS                                                              128

SEQ ID NO: 249          moltype = AA  length = 123
FEATURE                 Location/Qualifiers
REGION                  1..123
                        note = Synthetic
source                  1..123
                        mol_type = protein
                        organism = synthetic construct
SEQUENCE: 249
EVQLLESGGG LVQPGGSLRL SCAASGFTFS SYWMSWVRQA PGKGLEWVSA ISGSGGSTYY      60
ADSVKGRFTI SRDNSKNTLY LQMNSLRAED TAVYYCARGR YSRSWERWYF DLWGRGTLVT      120
VSS                                                                   123

SEQ ID NO: 250          moltype = AA  length = 122
FEATURE                 Location/Qualifiers
REGION                  1..122
                        note = Synthetic
source                  1..122
                        mol_type = protein
                        organism = synthetic construct
SEQUENCE: 250
QVQLVQSGAE VKKPGASVKV SCKASGYTFT SQYMHWVRQA PGQGLEWMGW MNPNSGNTGY      60
AQKFQGRVTM TRDTSTSTVY MELSSLRSED TAVYYCARGQ YDSSGYYYFD YWGQGTLVTV      120
SS                                                                    122

SEQ ID NO: 251          moltype = AA  length = 122
FEATURE                 Location/Qualifiers
REGION                  1..122
                        note = Synthetic
source                  1..122
```

```
                        mol_type = protein
                        organism = synthetic construct
SEQUENCE: 251
QVQLVQSGAE VKKPGASVKV SCKASGYTFT TYYMNWVRQA PGQGLEWMGI LSPSGGGTSY    60
APKFQGRVTM TRDTSTSTVY MELSSLRSED TAVYYCARAT YYDFWSGSLD YWGQGTLVTV   120
SS                                                                  122

SEQ ID NO: 252          moltype = AA  length = 119
FEATURE                 Location/Qualifiers
REGION                  1..119
                        note = Synthetic
source                  1..119
                        mol_type = protein
                        organism = synthetic construct
SEQUENCE: 252
QVQLVQSGAE VKKPGASVKV SCKASGYTFT SYFMHWVRQA PGQGLEWMGW MNPNNGNTGY    60
AQKFQGRVTM TRDTSTSTVY MELSSLRSED TAVYYCTRQA GYSSGWDYWG QGTLVTVSS    119

SEQ ID NO: 253          moltype = AA  length = 123
FEATURE                 Location/Qualifiers
REGION                  1..123
                        note = Synthetic
source                  1..123
                        mol_type = protein
                        organism = synthetic construct
SEQUENCE: 253
QVQLVQSGAE VKKPGASVKV SCKASGYTLT TWYMQWVRQA PGQGLEWMGW ISPYTGNTIY    60
APNVQGRVTM TRDTSTSTVY MELSSLRSED TAVYYCTRAV YDILTGAYYF DYWGQGTLVT   120
VSS                                                                 123

SEQ ID NO: 254          moltype = AA  length = 121
FEATURE                 Location/Qualifiers
REGION                  1..121
                        note = Synthetic
source                  1..121
                        mol_type = protein
                        organism = synthetic construct
SEQUENCE: 254
QVQLVQSGAE VKKPGASVKV SCKASGGTFS SYAISWVRQA PGQGLEWMGW ISTYNGNTNY    60
AQKFQGRVTM TRDTSTSTVY MELSSLRSED TAVYYCARGR LPPYYYGMDV WGQGTTVTVS   120
S                                                                   121

SEQ ID NO: 255          moltype = AA  length = 123
FEATURE                 Location/Qualifiers
REGION                  1..123
                        note = Synthetic
source                  1..123
                        mol_type = protein
                        organism = synthetic construct
SEQUENCE: 255
QVQLVQSGVR WRSLGPPVKV SCKASGDTFS RYYLHWVRQA PGQGLEWMGR IIPILGIANY    60
AQKFQGRVTI TADESTSTAY MELSSLRSED TAVYYCARMA TVTKHTYWYF DLWGRGTLVT   120
VSS                                                                 123

SEQ ID NO: 256          moltype = AA  length = 124
FEATURE                 Location/Qualifiers
REGION                  1..124
                        note = Synthetic
source                  1..124
                        mol_type = protein
                        organism = synthetic construct
SEQUENCE: 256
EVQLLESGGG LVQPGGSLRL SCAASGFTFS GQWVHWVRQA PGKGLEWVAL ISYDGGSTYY    60
ADSVKGRFTI SRDNSKNTLY LQMNSLRAED TAVYYCARAG RSTSRYYYYY MDVWGKGTTV   120
TVSS                                                                124

SEQ ID NO: 257          moltype = AA  length = 121
FEATURE                 Location/Qualifiers
REGION                  1..121
                        note = Synthetic
source                  1..121
                        mol_type = protein
                        organism = synthetic construct
SEQUENCE: 257
QVQLVQSGAE VKKPGASVKV SCKASGYIFT PNYIQWVRQA PGQGLEWMGI INPSGRSTSY    60
AQKFQGRVTM TRDTSTSTVY MELSSLRSED TAVYYCARSS SGYTTDAFDI WGQGTTVTVS   120
S                                                                   121

SEQ ID NO: 258          moltype = AA  length = 120
```

```
FEATURE                 Location/Qualifiers
REGION                  1..120
                        note = Synthetic
source                  1..120
                        mol_type = protein
                        organism = synthetic construct
SEQUENCE: 258
QVQLVQSGAE VKKPGSSVKV SCKASGYTFT ASYIHWVRQA PGQGLEWMGG IIPIFGSPNY   60
AQKFQGRVTI TADESTSTAY MELSSLRSED TAVYYCAREY QLMNVGMDVW GQGTTVTVSS  120

SEQ ID NO: 259          moltype = AA  length = 118
FEATURE                 Location/Qualifiers
REGION                  1..118
                        note = Synthetic
source                  1..118
                        mol_type = protein
                        organism = synthetic construct
SEQUENCE: 259
EVQLLESGGG LVQPGGSLRL SCAASGFIFS DSHLHWVRQA PGKGLEWLSV IYAGGSRYYA   60
DSVKGRFTIS RDNSKNTLYL QMNSLRAEDT AVYYCARGKQ RADAFDIWGQ GTLVTVSS   118

SEQ ID NO: 260          moltype = AA  length = 124
FEATURE                 Location/Qualifiers
REGION                  1..124
                        note = Synthetic
source                  1..124
                        mol_type = protein
                        organism = synthetic construct
SEQUENCE: 260
EVQLLESGGG LVKPGGSLRL SCAASGFTFS SYWMHWVRQA PGKGLEWVST ISGSGAGTWY   60
ADSVKGRFTI SRDDSKNTLY LQMNSLKTED TAVYYCARDV DPSRQSYYHG VDVWGQGTTV  120
TVSS                                                              124

SEQ ID NO: 261          moltype = AA  length = 125
FEATURE                 Location/Qualifiers
REGION                  1..125
                        note = Synthetic
source                  1..125
                        mol_type = protein
                        organism = synthetic construct
SEQUENCE: 261
QVQLVQSGAE VKKPGASVKV SCKASGYIFT NYWIQWVRQA PGQGLEWMGW INPNSGGTRY   60
ARNFQGRVTM TRDTSTSTVY MELSSLRSED TAVYYCARGR YYYGSGSQYH AFDIWGQGTM  120
VTVSS                                                             125

SEQ ID NO: 262          moltype = AA  length = 121
FEATURE                 Location/Qualifiers
REGION                  1..121
                        note = Synthetic
source                  1..121
                        mol_type = protein
                        organism = synthetic construct
SEQUENCE: 262
QVQLVQSGAE VKKPGASVKV SCKASEYTFT NYYMHWVRQA PGQGLEWMGW LNPNSGTNYA   60
QKFQGRVTMT RDTSTSTVYM ELSSLRSEDT AVYYCARGRY DSSGYYYFDY WGQGTLVTVS  120
S                                                                 121

SEQ ID NO: 263          moltype = AA  length = 122
FEATURE                 Location/Qualifiers
REGION                  1..122
                        note = Synthetic
source                  1..122
                        mol_type = protein
                        organism = synthetic construct
SEQUENCE: 263
QVQLVQSGAE VKKPGSSVKV SCKASGDTFT GYDMQWVRQA PGQGLEWMGI INPSGAGTNY   60
AQKFQGRVTI TADESTSTAY MELSSLRSED TAVYYCAGTV TTPYQYYGMD VWGQGTTVTV  120
SS                                                                122

SEQ ID NO: 264          moltype = AA  length = 119
FEATURE                 Location/Qualifiers
REGION                  1..119
                        note = Synthetic
source                  1..119
                        mol_type = protein
                        organism = synthetic construct
SEQUENCE: 264
EVQLLESGGG LVQPGGSLRL SCAASTFPFS SYSMNWVRQA PGKGLEWVAV ISYDGRIKDY   60
ADSVKGRFTI SRDNSKNTLY LQMNSLRAED TAVYYCARVR GFSFWFDPWG QGTLVTVSS  119
```

```
SEQ ID NO: 265           moltype = AA  length = 119
FEATURE                  Location/Qualifiers
REGION                   1..119
                         note = Synthetic
source                   1..119
                         mol_type = protein
                         organism = synthetic construct
SEQUENCE: 265
EVQLLESGGG LVQPGGSLRL SCAASGFTFS SYSMNWVRQA PGKGLEWVAV ISYDGRIKDY    60
ADSVKGRFTI SRDNSKNTLY LQMNSLRAED TAVYYCARVR GFSFWFDPWG QGTLVTVSS   119

SEQ ID NO: 266           moltype = AA  length = 116
FEATURE                  Location/Qualifiers
REGION                   1..116
                         note = Synthetic
source                   1..116
                         mol_type = protein
                         organism = synthetic construct
SEQUENCE: 266
EVQLLESGGG LVQPGGSLRL SCAASGFTFS SYWMSWVRQA PGKGLEWVSG ISWNGGKTHY    60
ADSVKGRFTI SRDNSKNTLY LQMNSLRAED TAVYYCARGG GYFDYWGQGT LVTVSS      116

SEQ ID NO: 267           moltype = AA  length = 128
FEATURE                  Location/Qualifiers
REGION                   1..128
                         note = Synthetic
source                   1..128
                         mol_type = protein
                         organism = synthetic construct
SEQUENCE: 267
QVQLVQSGAE VKKPGASVKV SCKASGYSFT GYYIHWVRQA PGQGLEWMGW MNPNSGNTGY    60
AQKFQGRVTM TRDTSTSTVY MELSSLRSED TAVYYCARGR YGSSGWSPGY YYYYMDVWGK   120
GTTVTVSS                                                           128

SEQ ID NO: 268           moltype = AA  length = 121
FEATURE                  Location/Qualifiers
REGION                   1..121
                         note = Synthetic
source                   1..121
                         mol_type = protein
                         organism = synthetic construct
SEQUENCE: 268
EVQLLESGGG LVQPGGSLRL SCAASGFTFS SYWMSWVRQA PGKGLEWVSA ISGSGGSTYY    60
ADSVKGRFTI SRDNSKNTLY LQMNSLRAED TAVYYCARAR DSGSPKDFDY WGQGTLVTVS   120
S                                                                  121

SEQ ID NO: 269           moltype = AA  length = 116
FEATURE                  Location/Qualifiers
REGION                   1..116
                         note = Synthetic
source                   1..116
                         mol_type = protein
                         organism = synthetic construct
SEQUENCE: 269
EVQLLESGGG LVQPGGSLRL SCAASGFTFS SYAMHWVRQA PGKGLEWVAG TSLDGNKNYY    60
ADSVKGRFTI SRDNSKNTLY LQMNSLRAED TAVYYCARGT MARGSWGQGT LVTVSS      116

SEQ ID NO: 270           moltype = AA  length = 118
FEATURE                  Location/Qualifiers
REGION                   1..118
                         note = Synthetic
source                   1..118
                         mol_type = protein
                         organism = synthetic construct
SEQUENCE: 270
EVQLLESGGG LVQPGGSLRL SCAASGFTFS SYWMSWVRQA PGKGLEWVST ISGSGGTTYY    60
ADSVKGRFTI SRDNSKNTLY LQNEQPGAED TAVYYCARAT DYPGMDVWGQ GTTVTVSS    118

SEQ ID NO: 271           moltype = AA  length = 127
FEATURE                  Location/Qualifiers
REGION                   1..127
                         note = Synthetic
source                   1..127
                         mol_type = protein
                         organism = synthetic construct
SEQUENCE: 271
QVQLVQSGAE VKKPGASVKV SCKASGYTLT NYYMHWVRQA PGQGLEWMGW INPHSGGTNY    60
AQKFQGRVTM TRDTSTSTVY MELSSLRSED TAVYYCTRGR MHYDSSVHYY YYGMDVWGQG   120
```

```
TLVTVSS                                                                             127

SEQ ID NO: 272          moltype = AA  length = 125
FEATURE                 Location/Qualifiers
REGION                  1..125
                        note = Synthetic
source                  1..125
                        mol_type = protein
                        organism = synthetic construct
SEQUENCE: 272
QVQLVQSGAE VKKPGASVKV SCKASGGTGS SYAISWVRQA PGQGLEWMGL IDPSPGTTYY     60
AQKFQGRVTM TRDTSTSTVY MELSSLRSED TAVYYCARVS IVGATPDYYY GMDVWGKGTL    120
VTVSS                                                                125

SEQ ID NO: 273          moltype = AA  length = 118
FEATURE                 Location/Qualifiers
REGION                  1..118
                        note = Synthetic
source                  1..118
                        mol_type = protein
                        organism = synthetic construct
SEQUENCE: 273
QVQLVQSGAE VKKPGASVKV SCKASGYTFT SYDINWVRQA PGQGLEWMGR INPNSGGTNF     60
AQKFQGRVTM TRDTSTSTVY MELSSLRSED TAVYYCARVI RGGKFDPWGQ GTLVTVSS      118

SEQ ID NO: 274          moltype = AA  length = 125
FEATURE                 Location/Qualifiers
REGION                  1..125
                        note = Synthetic
source                  1..125
                        mol_type = protein
                        organism = synthetic construct
SEQUENCE: 274
QVQLVQSGAE VKKPGSSVKV SCKASGYTFT NYGITWVRQA PGKGLEWMGW MNPNSANTGY     60
AQKFQGRVTI TADESTSTAY MELSSLRSED TAVYYCARGL YAAAGDQYYY GMDVWGQGTL    120
VTVSS                                                                125

SEQ ID NO: 275          moltype = AA  length = 115
FEATURE                 Location/Qualifiers
REGION                  1..115
                        note = Synthetic
source                  1..115
                        mol_type = protein
                        organism = synthetic construct
SEQUENCE: 275
QVQLVQSGAE VKKPGASVKV SCKASGDTFS SYAISWVRQA PGQGLEWMGV INPSGGGTTY     60
AKKFQGRVTM TRDTSTSTVY MELSSLRSED TAVYYCARGA AFDYWGQGTL VTVSS         115

SEQ ID NO: 276          moltype = AA  length = 123
FEATURE                 Location/Qualifiers
REGION                  1..123
                        note = Synthetic
source                  1..123
                        mol_type = protein
                        organism = synthetic construct
SEQUENCE: 276
QVQLVQSGAE VKKPGSSVKV SCKASGYTFT GYYMHWVRQA PGQGLEWMGW INPDSGDTNF     60
AQKFQGRVTI TADESTSTAY MELSSLRSED TAVYYCAREY GDYGYYYYGM DVWGQGTMVT    120
VSS                                                                  123

SEQ ID NO: 277          moltype = AA  length = 127
FEATURE                 Location/Qualifiers
REGION                  1..127
                        note = Synthetic
source                  1..127
                        mol_type = protein
                        organism = synthetic construct
SEQUENCE: 277
QVQLVQSGAE VKKPGASVKV SCKASGYTFT NYYIHWVRQA PGQGLEWMGW MNPNSANTGY     60
AQKFQGRVTM TRDTSTSTVY MELSSLRSED TAVYYCARGI YYYDSSGGSY YYGMDVWGQG    120
TTVTVSS                                                              127

SEQ ID NO: 278          moltype = AA  length = 122
FEATURE                 Location/Qualifiers
REGION                  1..122
                        note = Synthetic
source                  1..122
                        mol_type = protein
                        organism = synthetic construct
```

```
SEQUENCE: 278
QVQLVQSGAE VKKPGASVKV SCKASGYTFT GYYMHWVRQA PGQGLEWMGW MNPNSGNTGY    60
AQKFQGRVTM TRDTSTSTVY MELSSLRSED TAVYYCAREL SSSWYSYGMD VWGQGTTVTV   120
SS                                                                 122

SEQ ID NO: 279          moltype = AA  length = 119
FEATURE                 Location/Qualifiers
REGION                  1..119
                        note = Synthetic
source                  1..119
                        mol_type = protein
                        organism = synthetic construct
SEQUENCE: 279
EVQLLESGGG LVKPGGSLRL SCAASGFTLS DYGMYWVRQA PGKGLEWVSY ISSSGSTIYY    60
ADSVKGRFTI SRDDSKNTLY LQMNSLKTED TAVYYCARVS GGSWYDRLLG PGNPVTVSS    119

SEQ ID NO: 280          moltype = AA  length = 119
FEATURE                 Location/Qualifiers
REGION                  1..119
                        note = Synthetic
source                  1..119
                        mol_type = protein
                        organism = synthetic construct
SEQUENCE: 280
QVQLVQSGAE VKKPGSSVKV SCKASGYTFS SYGINWVRQA PGQGLEWMGR IIPIFGAANY    60
AQKFQGRVTI TADESTSTAY MELSSLRSED TAVYYCTRTY FDWFFFDYWG QGTLVTVSS    119

SEQ ID NO: 281          moltype = AA  length = 125
FEATURE                 Location/Qualifiers
REGION                  1..125
                        note = Synthetic
source                  1..125
                        mol_type = protein
                        organism = synthetic construct
SEQUENCE: 281
QVQLVQSGAE VKKPGASVKV SCKASGYTFT SYGISWVRQA PGQGLEWMGW INPNNGGTNY    60
AQKFQGRVTM TRDTSTSTVY MELSSLRSED TAVYYCARGR YSGHFGVYYY GMDVWGQGTT   120
VTVSS                                                              125

SEQ ID NO: 282          moltype = AA  length = 119
FEATURE                 Location/Qualifiers
REGION                  1..119
                        note = Synthetic
source                  1..119
                        mol_type = protein
                        organism = synthetic construct
SEQUENCE: 282
QVQLVQSGAE VKKPGASVKV SCKASGYTFS SYYMHWVRQA PGQGLEWMAW MNPNSGNTGY    60
AQKFQGRVTM TRDTSTSTVY MELSSLRSED TAVYYCAREP YGDYGFDYWG QGTLVTVSS    119

SEQ ID NO: 283          moltype = AA  length = 107
FEATURE                 Location/Qualifiers
REGION                  1..107
                        note = Synthetic
source                  1..107
                        mol_type = protein
                        organism = synthetic construct
SEQUENCE: 283
DIQMTQSPSS LSASVGDRVT ITCQASQDIS NYLNWYQQKP GKAPKLLIYA ASSLQSGVPS    60
RFSGSGSGTD FTLTISSLQP EDFATYYCQQ TDSIPITFGQ GTKVEIK                 107

SEQ ID NO: 284          moltype = AA  length = 107
FEATURE                 Location/Qualifiers
REGION                  1..107
                        note = Synthetic
source                  1..107
                        mol_type = protein
                        organism = synthetic construct
SEQUENCE: 284
DIQMTQSPSS LSASVGDRVT ITCRASQYIS SYLAWYQQKP GKAPKLLIYA ASTLQSGVPS    60
RFSGSGSGTD FTLTISSLQP EDFATYYCQQ SYSTPLTFGP GTKVDIK                 107

SEQ ID NO: 285          moltype = AA  length = 107
FEATURE                 Location/Qualifiers
REGION                  1..107
                        note = Synthetic
source                  1..107
                        mol_type = protein
                        organism = synthetic construct
```

-continued

```
SEQUENCE: 285
DIQMTQSPSS LSASVGDRVT ITCRASQNIG SYLNWYQQKP GKAPKLLIYA ASSLQSGVPS    60
RFSGSGSGTD FTLTISSLQP EDFATYYCQQ TNSFPLTFGG GTKVEIK                 107

SEQ ID NO: 286          moltype = AA  length = 107
FEATURE                 Location/Qualifiers
REGION                  1..107
                        note = Synthetic
source                  1..107
                        mol_type = protein
                        organism = synthetic construct
SEQUENCE: 286
DIQMTQSPSS LSASVGDRVT ITCRASQSIS SHLNWYQQKP GKAPKLLIYA ASTLQSGVPS    60
RFSGSGSGTD FTLTISSLQP EDFATYYCQQ SYSTPLTFGG GTKVEIK                 107

SEQ ID NO: 287          moltype = AA  length = 107
FEATURE                 Location/Qualifiers
REGION                  1..107
                        note = Synthetic
source                  1..107
                        mol_type = protein
                        organism = synthetic construct
SEQUENCE: 287
DIQMTQSPSS LSASVGDRVT ITCRASQSIN NWLAWYQQKP GKAPKLLIYA ASTLQSGVPS    60
RFSGSGSGTD FTLTISSLQP EDFATYYCEQ NYRLPITFGQ GTRLEIK                 107

SEQ ID NO: 288          moltype = AA  length = 107
FEATURE                 Location/Qualifiers
REGION                  1..107
                        note = Synthetic
source                  1..107
                        mol_type = protein
                        organism = synthetic construct
SEQUENCE: 288
DIQMTQSPSS LSASVGDRVT ITCQASQDIS NYLNWYQQKP GKAPKLLIYA ASSLHPGVPS    60
RFSGSGSGTD FTLTISSLQP EDFATYYCQQ SDSFPLTFGG GTKVEIK                 107

SEQ ID NO: 289          moltype = AA  length = 107
FEATURE                 Location/Qualifiers
REGION                  1..107
                        note = Synthetic
source                  1..107
                        mol_type = protein
                        organism = synthetic construct
SEQUENCE: 289
DIQMTQSPSS LSASVGDRVT ITCQASQDIS NYLNWYQQKP GKAPKLLIYA ASNLESGVPS    60
RFSGSGSGTD FTLTISSLQP EDFATYYCQQ TNSFPITFGQ GTKLEIK                 107

SEQ ID NO: 290          moltype = AA  length = 107
FEATURE                 Location/Qualifiers
REGION                  1..107
                        note = Synthetic
source                  1..107
                        mol_type = protein
                        organism = synthetic construct
SEQUENCE: 290
DIQMTQSPSS LSASVGDRVT ITCQASQDIR NYLNWYQQKP GKAPKLLIYA ASTLQSGVPS    60
RFSGSGSGTD FTLTISSLQP EDFATYYCQQ SYSFPLTFGG GTKVEIK                 107

SEQ ID NO: 291          moltype = AA  length = 107
FEATURE                 Location/Qualifiers
REGION                  1..107
                        note = Synthetic
source                  1..107
                        mol_type = protein
                        organism = synthetic construct
SEQUENCE: 291
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPLTFGG GTKVEIK                 107

SEQ ID NO: 292          moltype = AA  length = 107
FEATURE                 Location/Qualifiers
REGION                  1..107
                        note = Synthetic
source                  1..107
                        mol_type = protein
                        organism = synthetic construct
SEQUENCE: 292
DIQMTQSPSS LSASVGDRVT ITCQASQDIS NYLNWYQQKP GKAPKLLIYA AFNLQGGVPS    60
```

```
RFSGSGSGTD FTLTISSLQP EDFATYYCQQ AHSFPLTFGP GTKVDIK                 107

SEQ ID NO: 293          moltype = AA   length = 107
FEATURE                 Location/Qualifiers
REGION                  1..107
                        note = Synthetic
source                  1..107
                        mol_type = protein
                        organism = synthetic construct
SEQUENCE: 293
DIQMTQSPSS LSASVGDRVT ITCRASQSIS SYLNWYQQKP GKAPKLLIYG ASTLESGVPS    60
RFSGSGSGTD FTLTISSLQP EDFATYYCQQ SYSTPITFGQ GTKLEIK                 107

SEQ ID NO: 294          moltype = AA   length = 113
FEATURE                 Location/Qualifiers
REGION                  1..113
                        note = Synthetic
source                  1..113
                        mol_type = protein
                        organism = synthetic construct
SEQUENCE: 294
DIVMTQSPDS LAVSLGERAT INCKSSQSVL YSSNNKNYLA WYQQKPGQPP KLLIYWASTR    60
ESGVPDRFSG SGSGTDFTLT ISSLQAEDVA VYYCQQYYST PLTFGQGTKV EIK          113

SEQ ID NO: 295          moltype = AA   length = 107
FEATURE                 Location/Qualifiers
REGION                  1..107
                        note = Synthetic
source                  1..107
                        mol_type = protein
                        organism = synthetic construct
SEQUENCE: 295
DIQMTQSPSS LSASVGDRVT ITCQASQDIS NYLNWYQQKP GKAPKLLIYA TSTLQSGVPS    60
RFSGSGSGTD FTLTISSLQP EDFATYYCQQ ANSLPYSFGQ GTKLEIK                 107

SEQ ID NO: 296          moltype = AA   length = 107
FEATURE                 Location/Qualifiers
REGION                  1..107
                        note = Synthetic
source                  1..107
                        mol_type = protein
                        organism = synthetic construct
SEQUENCE: 296
DIQMTQSPSS LSASVGDRVT ITCRASENIG NWLAWYQQKP GKAPKLLIYA ASTLQSGVPS    60
RFSGSGSGTD FTLTISSLQP EDFATYYCQQ GYSTPYTFGQ GTKLEIK                 107

SEQ ID NO: 297          moltype = AA   length = 107
FEATURE                 Location/Qualifiers
REGION                  1..107
                        note = Synthetic
source                  1..107
                        mol_type = protein
                        organism = synthetic construct
SEQUENCE: 297
EIVMTQSPAT LSVSPGERAT LSCRASQSVS SNLAWYQQKP GQAPRLLIYG ASTRATGIPA    60
RFSGSGSGTE FTLTISSLQS EDFAVYYCQQ YGTSPFTFGQ GTRLEIK                 107

SEQ ID NO: 298          moltype = AA   length = 107
FEATURE                 Location/Qualifiers
REGION                  1..107
                        note = Synthetic
source                  1..107
                        mol_type = protein
                        organism = synthetic construct
SEQUENCE: 298
DIQMTQSPSS LSASVGDRVT ITCRASQGIS NNLNWYQQKP GKAPKLLIYA ASILQSGVPS    60
RFSGSGSGTD FTLTISSLQP EDFATYYCQQ SYTTTLTFGP GTKVDIK                 107

SEQ ID NO: 299          moltype = AA   length = 107
FEATURE                 Location/Qualifiers
REGION                  1..107
                        note = Synthetic
source                  1..107
                        mol_type = protein
                        organism = synthetic construct
SEQUENCE: 299
DIQMTQSPSS LSASVGDRVT ITCRASQSIS KFLNWYQQKP GKAPKLLIYS ASNLQSGVPS    60
RFSGSGSGTD FTLTISSLQP EDFATYYCQQ ANSFPLTFGQ GTKVEIK                 107
```

```
SEQ ID NO: 300          moltype = AA  length = 107
FEATURE                 Location/Qualifiers
REGION                  1..107
                        note = Synthetic
source                  1..107
                        mol_type = protein
                        organism = synthetic construct
SEQUENCE: 300
DIQMTQSPSS LSASVGDRVT ITCRASENIG NWLAWYHQKP GKAPKLLIYA ASTLQSGVPS      60
RFSGSGSGTD FTLTISSLQP EDFATYYCQQ GYSTPYTFGQ GTKLEIK                   107

SEQ ID NO: 301          moltype = AA  length = 112
FEATURE                 Location/Qualifiers
REGION                  1..112
                        note = Synthetic
source                  1..112
                        mol_type = protein
                        organism = synthetic construct
SEQUENCE: 301
DIVMTQSPLF LPVTPGEPAS ISCRSSQSLL HSNGYNYLDW YLQKPGQSPQ LLIYLGSNRA      60
SGVPDRFSGS GSGTDFTLKI SRVEAEDVGV YYCMQGAHWP YTFGQGTKLE IK             112

SEQ ID NO: 302          moltype = AA  length = 107
FEATURE                 Location/Qualifiers
REGION                  1..107
                        note = Synthetic
source                  1..107
                        mol_type = protein
                        organism = synthetic construct
SEQUENCE: 302
DIQMTQSPSS LSASVGDRVT ITCRASQSIG SYLNWYQQKP GKAPKLLIYA ASRLQSGVPS      60
RFSGSGSGTD FTLTISSLQP EDFATYYCQQ SYSTPLTFGQ GTKVEIK                   107

SEQ ID NO: 303          moltype = AA  length = 107
FEATURE                 Location/Qualifiers
REGION                  1..107
                        note = Synthetic
source                  1..107
                        mol_type = protein
                        organism = synthetic construct
SEQUENCE: 303
DIQMTQSPSS LSASVGDRVT ITCQASQEIG NYLNWYQQKP GKAPKLLIYG ASSLQSGVPS      60
RFSGSGSGTD FTLTISSLQP EDFATYYCQQ SYSTPLTFGG GTKVEIK                   107

SEQ ID NO: 304          moltype = AA  length = 112
FEATURE                 Location/Qualifiers
REGION                  1..112
                        note = Synthetic
source                  1..112
                        mol_type = protein
                        organism = synthetic construct
SEQUENCE: 304
DIVMTQSPLS LPVTPGEPAS ISCRSSQSLL HSNGYNYLDW YLQKPGQSPQ LLIYAASSLQ      60
SGVPDRFSGS GSGTDFTLKI SRVEAEDVGV YYCMQALQTP LTFGGGTKVE IK             112

SEQ ID NO: 305          moltype = AA  length = 107
FEATURE                 Location/Qualifiers
REGION                  1..107
                        note = Synthetic
source                  1..107
                        mol_type = protein
                        organism = synthetic construct
SEQUENCE: 305
DIQMTQSPSS LSASVGDRVT ITCRASQSIS SYLNWYQQKP GKAPKLLIYL ASSLQSGVPS      60
RFSGSGSGTD FTLTISSLQP EDFATYYCQQ SYGIPLTFGG GTKVEIK                   107

SEQ ID NO: 306          moltype = AA  length = 107
FEATURE                 Location/Qualifiers
REGION                  1..107
                        note = Synthetic
source                  1..107
                        mol_type = protein
                        organism = synthetic construct
SEQUENCE: 306
DIQMTQSPSS LSASVGDRVT ITCQASQDIS NYLNWYQQKP GKAPKLLIYK ASSLESGVPS      60
RFSGSGSGTD FTLTISSLQP EDFATYYCQQ ANTFPLTFGG GTKVEIK                   107

SEQ ID NO: 307          moltype = AA  length = 107
FEATURE                 Location/Qualifiers
```

```
REGION                  1..107
                        note = Synthetic
source                  1..107
                        mol_type = protein
                        organism = synthetic construct
SEQUENCE: 307
DIQMTQSPSS LSASVGDRVT ITCQASQDIT NFLNWYQQKP GKAPKLLIYA ASSLQSGVPS    60
RFSGSGSGTD FTLTISSLQP EDFATYYCQQ TYSFPLTFGP GTKVDIK                 107

SEQ ID NO: 308          moltype = AA  length = 106
FEATURE                 Location/Qualifiers
REGION                  1..106
                        note = Synthetic
source                  1..106
                        mol_type = protein
                        organism = synthetic construct
SEQUENCE: 308
DIQMTQSPSS LSASVGDRVT ITCRASQSIS TFLNWYQQKP GKAPKLLIYA ASSLQTGVPS    60
RFSGSGSGTD FTLTISSLQP EDFATYYCQQ SYSTPPFGPG TKVDIK                  106

SEQ ID NO: 309          moltype = AA  length = 107
FEATURE                 Location/Qualifiers
REGION                  1..107
                        note = Synthetic
source                  1..107
                        mol_type = protein
                        organism = synthetic construct
SEQUENCE: 309
DIQMTQSPSS LSASVGDRVT ITCQASQDIS KYLNWYQQKP GKAPKLLIYA ASNLQKGVPS    60
RFSGSGSGTD FTLTISSLQP EDFATYYCQQ ANSFPRTFGQ GTKVEIK                 107

SEQ ID NO: 310          moltype = AA  length = 107
FEATURE                 Location/Qualifiers
REGION                  1..107
                        note = Synthetic
source                  1..107
                        mol_type = protein
                        organism = synthetic construct
SEQUENCE: 310
DIQMTQSPSS LSASVGDRVT ITCQASQDIG NYLNWYQQKP GKAPKLLIYA ASSLQSGVPS    60
RFSGSGSGTD FTLTISSLQP EDFATYYCLQ HNSFPPTFGG GTKVEIK                 107

SEQ ID NO: 311          moltype = AA  length = 107
FEATURE                 Location/Qualifiers
REGION                  1..107
                        note = Synthetic
source                  1..107
                        mol_type = protein
                        organism = synthetic construct
SEQUENCE: 311
DIQMTQSPSS LSASVGDRVT ITCRASQDIR NYLAWYQQKP GKAPKLLIYA ASTLQSGVPS    60
RFSGSGSGTD FTLTISSLQP EDFATYYCLQ AISFPFTFGP GTKVDIK                 107

SEQ ID NO: 312          moltype = AA  length = 107
FEATURE                 Location/Qualifiers
REGION                  1..107
                        note = Synthetic
source                  1..107
                        mol_type = protein
                        organism = synthetic construct
SEQUENCE: 312
DIQMTQSPSS LSASVGDRVT ITCQASQDIR NYLNWYQQKP GKAPKLLIYD TSNLETGVPS    60
RFSGSGSGTD FTLTISSLQP EDFATYYCQQ AYSLPWTFGQ GTKLEIK                 107

SEQ ID NO: 313          moltype = AA  length = 107
FEATURE                 Location/Qualifiers
REGION                  1..107
                        note = Synthetic
source                  1..107
                        mol_type = protein
                        organism = synthetic construct
SEQUENCE: 313
DIQMTQSPSS LSASVGDRVT ITCQASQDIS NYLNWYQQKP GKAPKLLIYS ASNLQSGVPS    60
RFSGSGSGTD FTLTISSLQP EDFATYYCQQ SYTTPYTFGQ GTKLEIK                 107

SEQ ID NO: 314          moltype = AA  length = 107
FEATURE                 Location/Qualifiers
REGION                  1..107
                        note = Synthetic
```

```
source                  1..107
                        mol_type = protein
                        organism = synthetic construct
SEQUENCE: 314
DIQMTQSPSS LSASVGDRVT ITCRASQSIS SYLNWYQQKP GKAPKLLIYA ASTLQSGVPS    60
RFSGSGSGTD FTLTISSLQP EDFATYYCQQ SDSFPLTFGQ GTKVEIK                 107

SEQ ID NO: 315          moltype = AA   length = 113
FEATURE                 Location/Qualifiers
REGION                  1..113
                        note = Synthetic
source                  1..113
                        mol_type = protein
                        organism = synthetic construct
SEQUENCE: 315
DIVMTQSPDS LAVSLGERAT INCKSSQSVL YSSNNKNYLA WYQQKPGQPP KLLIYWASFR    60
ESGVPDRFSG SGSGTDFTLT ISSLQAEDVA VYYCQQYYTT PLTFGGGTKV EIK          113

SEQ ID NO: 316          moltype = AA   length = 113
FEATURE                 Location/Qualifiers
REGION                  1..113
                        note = Sythnetic
source                  1..113
                        mol_type = protein
                        organism = synthetic construct
SEQUENCE: 316
DIVMTQSPDS LAVSLGERAT INCKSSQSVL YSSNNKNYLA WYQQKPGQPP KLLIYWASAR    60
ESGVPDRFSG SGSGTDFTLT ISSLQAEDVA VYYCQQYKSA PYTFGQGTKV EIK          113

SEQ ID NO: 317          moltype = AA   length = 107
FEATURE                 Location/Qualifiers
REGION                  1..107
                        note = Synthetic
source                  1..107
                        mol_type = protein
                        organism = synthetic construct
SEQUENCE: 317
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SNSFPLTFGP GTKVDIK                 107

SEQ ID NO: 318          moltype = AA   length = 107
FEATURE                 Location/Qualifiers
REGION                  1..107
                        note = Synthetic
source                  1..107
                        mol_type = protein
                        organism = synthetic construct
SEQUENCE: 318
DIQMTQSPSS LSASVGDRVT ITCRASQSIS RHLNWYQQKP GKAPKLLIYA ASSLQSGVPS    60
RFSGSGSGTD FTLTISSLQP EDFATYYCQQ SYQTPLTFGG GTKVEIK                 107

SEQ ID NO: 319          moltype = AA   length = 113
FEATURE                 Location/Qualifiers
REGION                  1..113
                        note = Synthetic
source                  1..113
                        mol_type = protein
                        organism = synthetic construct
SEQUENCE: 319
DIVMTQSPDS LAVSLGERAT INCKSSQSVL YSSNNKNYLA WYQQKPGQPP KLLIYWASIR    60
ESGVPDRFSG SGSGTDFTLT ISSLQAEDVA VYYCQQYYSS PFTFGQGTKL EIK          113

SEQ ID NO: 320          moltype = AA   length = 112
FEATURE                 Location/Qualifiers
REGION                  1..112
                        note = Synthetic
source                  1..112
                        mol_type = protein
                        organism = synthetic construct
SEQUENCE: 320
DIVMTQSPLS LPVTPGEPAS ISCRSSQSLL HSNGYNYLDW YLQKPGQSPQ LLIYDASNLH    60
AGVPDRFSGS GSGTDFTLKI SRVEAEDVGV YYCMQALQAP VTFGQGTRLE IK           112

SEQ ID NO: 321          moltype = AA   length = 107
FEATURE                 Location/Qualifiers
REGION                  1..107
                        note = Synthetic
source                  1..107
                        mol_type = protein
```

```
                        organism = synthetic construct
SEQUENCE: 321
DIQMTQSPSS LSASVGDRVT ITCQASQDIS KYLNWYQQKP GKAPKLLIYA ASSLQSGVPS    60
RFSGSGSGTD FTLTISSLQP EDFATYYCQQ SNSFPLTFGG GTKLEIK                 107

SEQ ID NO: 322          moltype = AA   length = 107
FEATURE                 Location/Qualifiers
REGION                  1..107
                        note = Synthetic
source                  1..107
                        mol_type = protein
                        organism = synthetic construct
SEQUENCE: 322
DIQMTQSPSS LSASVGDRVT ITCRASQTVR SYLNWYQQKP GKAPKLLIYA ASTLQSGVPS    60
RFSGSGSGTD FTLTISSLQP EDFATYYCQQ TYRTPLTFGQ GTKVEIK                 107

SEQ ID NO: 323          moltype = AA   length = 10
FEATURE                 Location/Qualifiers
REGION                  1..10
                        note = Synthetic
source                  1..10
                        mol_type = protein
                        organism = synthetic construct
SEQUENCE: 323
VRGFSFWFEP                                                           10

SEQ ID NO: 324          moltype = AA   length = 119
FEATURE                 Location/Qualifiers
REGION                  1..119
                        note = Synthetic
source                  1..119
                        mol_type = protein
                        organism = synthetic construct
SEQUENCE: 324
EVQLLESGGG LVQPGGSLRL SCAASGFTFS SYSMNWVRQA PGKGLEWVAV ISYDGRIKDY    60
ADSVKGRFTI SRDNSKNTLY LQMNSLRAED TAVYYCARVR GFSFWFEPWG QGTLVTVSS    119

SEQ ID NO: 325          moltype = AA   length = 214
FEATURE                 Location/Qualifiers
REGION                  1..214
                        note = Synthetic
source                  1..214
                        mol_type = protein
                        organism = synthetic construct
SEQUENCE: 325
DIQMTQSPSS LSASVGDRVT ITCQASQDIS NYLNWYQQKP GKAPKLLIYA ASSLQSGVPS    60
RFSGSGSGTD FTLTISSLQP EDFATYYCQQ TDSIPITFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 326          moltype = AA   length = 214
FEATURE                 Location/Qualifiers
REGION                  1..214
                        note = Synthetic
source                  1..214
                        mol_type = protein
                        organism = synthetic construct
SEQUENCE: 326
DIQMTQSPSS LSASVGDRVT ITCRASQSIG SYLNWYQQKP GKAPKLLIYA ASRLQSGVPS    60
RFSGSGSGTD FTLTISSLQP EDFATYYCQQ SYSTPLTFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 327          moltype = AA   length = 214
FEATURE                 Location/Qualifiers
REGION                  1..214
                        note = Synthetic
source                  1..214
                        mol_type = protein
                        organism = synthetic construct
SEQUENCE: 327
DIQMTQSPSS LSASVGDRVT ITCRASQSIS SYLNWYQQKP GKAPKLLIYL ASSLQSGVPS    60
RFSGSGSGTD FTLTISSLQP EDFATYYCQQ SYGIPLTFGG GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 328          moltype = AA   length = 458
FEATURE                 Location/Qualifiers
REGION                  1..458
```

```
                        note = Synthetic
source                  1..458
                        mol_type = protein
                        organism = synthetic construct
SEQUENCE: 328
QVQLVQSGAE VKKPGASVKV SCKASGYTFT SYYMQWVRQA PGQGLEWMGW INPKSGGTNY    60
AQKFQGRVTM TRDTSTSTVY MELSSLRSED TAVYYCARGT YLRTGSSLSG YYYGMDVWGQ   120
GTTVTVSSAS TKGPSVFPLA PSSKSTSGGT AALGCLVKDY FPEPVTVSWN SGALTSGVHT   180
FPAVLQSSGL YSLSSVVTVP SSSLGTQTYI CNVNHKPSNT KVDKRVEPKS CDKTHTCPPC   240
PAPELLGGPS VFLFPPKPKD TLMISRTPEV TCVVVDVSHE DPEVKFNWYV DGVEVHNAKT   300
KPREEQYNST YRVVSVLTVL HQDWLNGKEY KCKVSNKALP APIEKTISKA KGQPREPQVY   360
TLPPSREEMT KNQVSLTCLV KGFYPSDIAV EWESNGQPEN NYKTTPPVLD SDGSFFLYSK   420
LTVDKSRWQQ GNVFSCSVMH EALHNHYTQK SLSLSPGK                          458

SEQ ID NO: 329          moltype = AA  length = 458
FEATURE                 Location/Qualifiers
REGION                  1..458
                        note = Synthetic
source                  1..458
                        mol_type = protein
                        organism = synthetic construct
SEQUENCE: 329
QVQLVQSGAE VKKPGASVKV SCKASGYTFT SYYMQWVRQA PGQGLEWMGW INPKSGGTNY    60
AQKFQGRVTM TRDTSTSTVY MELSSLRSED TAVYYCARGT YLRTGSSLSG YYYGMDVWGQ   120
GTTVTVSSAS TKGPSVFPLA PSSKSTSGGT AALGCLVKDY FPEPVTVSWN SGALTSGVHT   180
FPAVLQSSGL YSLSSVVTVP SSSLGTQTYI CNVNHKPSNT KVDKRVEPKS CDKTHTCPPC   240
PAPELLGGPS VFLFPPKPKD TLMISRTPEV TCVVVDVEHE DPEVKFNWYV DGVEVHNAKT   300
KPREEQYNST YRVVSVLTVL HQDWLNGKEY KCKVSNKALP APIEKTISKA KGQPREPQVY   360
TLPPSREEMT KNQVSLTCLV KGFYPSDIAV EWESNGQPEN NYKTTPPVLD SDGSFFLYSK   420
LTVDKSRWQQ GNVFSCSVMH EALHNHYTQK SLSLSPGK                          458

SEQ ID NO: 330          moltype = AA  length = 458
FEATURE                 Location/Qualifiers
REGION                  1..458
                        note = Synthetic
source                  1..458
                        mol_type = protein
                        organism = synthetic construct
SEQUENCE: 330
QVQLVQSGAE VKKPGASVKV SCKASGYTFT SYYMQWVRQA PGQGLEWMGW INPKSGGTNY    60
AQKFQGRVTM TRDTSTSTVY MELSSLRSED TAVYYCARGT YLRTGSSLSG YYYGMDVWGQ   120
GTTVTVSSAS TKGPSVFPLA PSSKSTSGGT AALGCLVKDY FPEPVTVSWN SGALTSGVHT   180
FPAVLQSSGL YSLSSVVTVP SSSLGTQTYI CNVNHKPSNT KVDKRVEPKS CDKTHTCPPC   240
PAPELLGGPS VFLFPPKPKD TLMISRTPEV TCVVVDVSHE DPEVKFNWYV DGVEVHNAKT   300
KPREEQYNST YRVVSVLTVL HQDWLNGKEY KCKVSNKALP APIEKTISKA KGQPRRPQVY   360
TLPPSREEMT KNQVSLTCLV KGFYPSDIAV EWESNGQPEN NYKTTPPVLD SDGSFFLYSK   420
LTVDKSRWQQ GNVFSCSVMH EALHNHYTQK SLSLSPGK                          458

SEQ ID NO: 331          moltype = AA  length = 458
FEATURE                 Location/Qualifiers
REGION                  1..458
                        note = Synthetic
source                  1..458
                        mol_type = protein
                        organism = synthetic construct
SEQUENCE: 331
QVQLVQSGAE VKKPGASVKV SCKASGYTFT SYYMQWVRQA PGQGLEWMGW INPKSGGTNY    60
AQKFQGRVTM TRDTSTSTVY MELSSLRSED TAVYYCARGT YLRTGSSLSG YYYGMDVWGQ   120
GTTVTVSSAS TKGPSVFPLA PSSKSTSGGT AALGCLVKDY FPEPVTVSWN SGALTSGVHT   180
FPAVLQSSGL YSLSSVVTVP SSSLGTQTYI CNVNHKPSNT KVDKRVEPKS CDKTHTCPPC   240
PAPELLGGPS VFLFPPKPKD TLMISRTPEV TCVVVDVEHE DPEVKFNWYV DGVEVHNAKT   300
KPREEQYNST YRVVSVLTVL HQDWLNGKEY KCKVSNKALP APIEKTISKA KGQPRRPQVY   360
TLPPSREEMT KNQVSLTCLV KGFYPSDIAV EWESNGQPEN NYKTTPPVLD SDGSFFLYSK   420
LTVDKSRWQQ GNVFSCSVMH EALHNHYTQK SLSLSPGK                          458

SEQ ID NO: 332          moltype = AA  length = 458
FEATURE                 Location/Qualifiers
REGION                  1..458
                        note = Synthetic
source                  1..458
                        mol_type = protein
                        organism = synthetic construct
SEQUENCE: 332
QVQLVQSGAE VKKPGASVKV SCKASGYTFT SYYMQWVRQA PGQGLEWMGW INPKSGGTNY    60
AQKFQGRVTM TRDTSTSTVY MELSSLRSED TAVYYCARGT YLRTGSSLSG YYYGMDVWGQ   120
GTTVTVSSAS TKGPSVFPLA PSSKSTSGGT AALGCLVKDY FPEPVTVSWN SGALTSGVHT   180
FPAVLQSSGL YSLSSVVTVP SSSLGTQTYI CNVNHKPSNT KVDKRVEPKS CDKTHTCPPC   240
PAPELLGGPS VFLFPPKPKD TLMISRTPEV TCVVVDVSHE DPEVKFNWYV DGVEVHNAKT   300
KPREEQYAST YRVVSVLTVL HQDWLNGKEY KCKVSNKALP APIEKTISKA KGQPREPQVY   360
```

```
TLPPSREEMT KNQVSLTCLV KGFYPSDIAV EWESNGQPEN NYKTTPPVLD SDGSFFLYSK   420
LTVDKSRWQQ GNVFSCSVMH EALHNHYTQK SLSLSPGK                           458

SEQ ID NO: 333            moltype = AA  length = 458
FEATURE                   Location/Qualifiers
REGION                    1..458
                          note = Synthetic
source                    1..458
                          mol_type = protein
                          organism = synthetic construct
SEQUENCE: 333
QVQLVQSGAE VKKPGASVKV SCKASGYTFT SYYMQWVRQA PGQGLEWMGW INPKSGGTNY    60
AQKFQGRVTM TRDTSTSTVY MELSSLRSED TAVYYCARGT YLRTGSSLSG YYYGMDVWGQ   120
GTTVTVSSAS TKGPSVFPLA PSSKSTSGGT AALGCLVKDY FPEPVTVSWN SGALTSGVHT   180
FPAVLQSSGL YSLSSVVTVP SSSLGTQTYI CNVNHKPSNT KVDKRVEPKS CDKTHTCPPC   240
PAPELLAGPS VFLFPPKPKD TLMISRTPEV TCVVVDVSHE DPEVKFNWYV DGVEVHNAKT   300
KPREEQYNST YRVVSVLTVL HQDWLNGKEY KCKVSNKALP APIEKTISKA KGQPREPQVY   360
TLPPSREEMT KNQVSLTCLV KGFYPSDIAV EWESNGQPEN NYKTTPPVLD SDGSFFLYSK   420
LTVDKSRWQQ GNVFSCSVMH EALHNHYTQK SLSLSPGK                           458

SEQ ID NO: 334            moltype = AA  length = 455
FEATURE                   Location/Qualifiers
REGION                    1..455
                          note = Synthetic
source                    1..455
                          mol_type = protein
                          organism = synthetic construct
SEQUENCE: 334
QVQLVQSGAE VKKPGASVKV SCKASGYIFT NYWIQWVRQA PGQGLEWMGW INPNSGGTRY    60
ARNFQGRVTM TRDTSTSTVY MELSSLRSED TAVYYCARGR YYYGSGSQYH AFDIWGQGTM   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSNTKVD KRVEPKSCDK THTCPPCPAP   240
ELLGGPSVFL FPPKPKDTLM ISRTPEVTCV VVDVSHEDPE VKFNWYVDGV EVHNAKTKPR   300
EEQYNSTYRV VSVLTVLHQD WLNGKEYKCK VSNKALPAPI EKTISKAKGQ PREPQVYTLP   360
PSREEMTKNQ VSLTCLVKGF YPSDIAVEWE SNGQPENNYK TTPPVLDSDG SFFLYSKLTV   420
DKSRWQQGNV FSCSVMHEAL HNHYTQKSLS LSPGK                              455

SEQ ID NO: 335            moltype = AA  length = 455
FEATURE                   Location/Qualifiers
REGION                    1..455
                          note = Synthetic
source                    1..455
                          mol_type = protein
                          organism = synthetic construct
SEQUENCE: 335
QVQLVQSGAE VKKPGASVKV SCKASGYIFT NYWIQWVRQA PGQGLEWMGW INPNSGGTRY    60
ARNFQGRVTM TRDTSTSTVY MELSSLRSED TAVYYCARGR YYYGSGSQYH AFDIWGQGTM   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSNTKVD KRVEPKSCDK THTCPPCPAP   240
ELLAGPSVFL FPPKPKDTLM ISRTPEVTCV VVDVSHEDPE VKFNWYVDGV EVHNAKTKPR   300
EEQYNSTYRV VSVLTVLHQD WLNGKEYKCK VSNKALPAPI EKTISKAKGQ PREPQVYTLP   360
PSREEMTKNQ VSLTCLVKGF YPSDIAVEWE SNGQPENNYK TTPPVLDSDG SFFLYSKLTV   420
DKSRWQQGNV FSCSVMHEAL HNHYTQKSLS LSPGK                              455

SEQ ID NO: 336            moltype = AA  length = 455
FEATURE                   Location/Qualifiers
REGION                    1..455
                          note = Synthetic
source                    1..455
                          mol_type = protein
                          organism = synthetic construct
SEQUENCE: 336
QVQLVQSGAE VKKPGASVKV SCKASGYIFT NYWIQWVRQA PGQGLEWMGW INPNSGGTRY    60
ARNFQGRVTM TRDTSTSTVY MELSSLRSED TAVYYCARGR YYYGSGSQYH AFDIWGQGTM   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSNTKVD KRVEPKSCDK THTCPPCPAP   240
EAAGGPSVFL FPPKPKDTLM ISRTPEVTCV VVDVSHEDPE VKFNWYVDGV EVHNAKTKPR   300
EEQYNSTYRV VSVLTVLHQD WLNGKEYKCK VSNKALPAPI EKTISKAKGQ PREPQVYTLP   360
PSREEMTKNQ VSLTCLVKGF YPSDIAVEWE SNGQPENNYK TTPPVLDSDG SFFLYSKLTV   420
DKSRWQQGNV FSCSVMHEAL HNHYTQKSLS LSPGK                              455

SEQ ID NO: 337            moltype = AA  length = 455
FEATURE                   Location/Qualifiers
REGION                    1..455
                          note = Synthetic
source                    1..455
                          mol_type = protein
                          organism = synthetic construct
SEQUENCE: 337
```

```
QVQLVQSGAE VKKPGASVKV SCKASGYIFT NYWIQWVRQA PGQGLEWMGW INPNSGGTRY    60
ARNFQGRVTM TRDTSTSTVY MELSSLRSED TAVYYCARGR YYYGSGSQYH AFDIWGQGTM   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSNTKVD KRVEPKSCDK THTCPPCPAP   240
ELLGGPSVFL FPPKPKDTLM ISRTPEVTCV VVDVSHEDPE VKFNWYVDGV EVHNAKTKPR   300
EEQYASTYRV VSVLTVLHQD WLNGKEYKCK VSNKALPAPI EKTISKAKGQ PREPQVYTLP   360
PSREEMTKNQ VSLTCLVKGF YPSDIAVEWE SNGQPENNYK TTPPVLDSDG SFFLYSKLTV   420
DKSRWQQGNV FSCSVMHEAL HNHYTQKSLS LSPGK                              455

SEQ ID NO: 338         moltype = AA   length = 451
FEATURE                Location/Qualifiers
REGION                 1..451
                       note = Synthetic
source                 1..451
                       mol_type = protein
                       organism = synthetic construct
SEQUENCE: 338
QVQLVQSGAE VKKPGASVKV SCKASGYIFT NYWIQWVRQA PGQGLEWMGW INPNSGGTRY    60
ARNFQGRVTM TRDTSTSTVY MELSSLRSED TAVYYCARGR YYYGSGSQYH AFDIWGQGTM   120
VTVSSASTKG PSVFPLAPCS RSTSESTAAL GCLVKDYFPE PVTVSWNSGA LTSGVHTFPA   180
VLQSSGLYSL SSVVTVPSSN FGTQTYTCNV DHKPSNTKVD KTVERKSCVE CPPCPAPPVA   240
GPSVFLPPPK PKDTLMISRT PEVTCVVVDV SHEDPEVQFN WYVDGVEVHN AKTKPREEQF   300
NSTFRVVSVL TVVHQDWLNG KEYKCKVSNK GLPAPIEKTI SKTKGQPREP QVYTLPPSRE   360
EMTKNQVSLT CLVKGFYPSD IAVEWESNGQ PENNYKTTPP MLDSDGSFFL YSKLTVDKSR   420
WQQGNVFSCS VMHEALHNHY TQKSLSLSPG K                                  451

SEQ ID NO: 339         moltype = AA   length = 455
FEATURE                Location/Qualifiers
REGION                 1..455
                       note = Synthetic
source                 1..455
                       mol_type = protein
                       organism = synthetic construct
SEQUENCE: 339
QVQLVQSGAE VKKPGASVKV SCKASGYIFT NYWIQWVRQA PGQGLEWMGW INPNSGGTRY    60
ARNFQGRVTM TRDTSTSTVY MELSSLRSED TAVYYCARGR YYYGSGSQYH AFDIWGQGTM   120
VTVSSASTKG PSVFPLAPSS KSTSGGTAAL GCLVKDYFPE PVTVSWNSGA LTSGVHTFPA   180
VLQSSGLYSL SSVVTVPSSS LGTQTYICNV NHKPSNTKVD KRVEPKSCDK THTCPPCPAP   240
ELLGGPSVFL FPPKPKDTLM ISRTPEVTCV VVDVSHEDPE VKFNWYVDGV EVHNAKTKPR   300
EEQYNSTYRV VSVLTVLHQD WLNGKEYKCK VSNKALPAPI EKTISKAKGQ PRRPQVYTLP   360
PSREEMTKNQ VSLTCLVKGF YPSDIAVEWE SNGQPENNYK TTPPVLDSDG SFFLYSKLTV   420
DKSRWQQGNV FSCSVMHEAL HNHYTQKSLS LSPGK                              455

SEQ ID NO: 340         moltype = AA   length = 449
FEATURE                Location/Qualifiers
REGION                 1..449
                       note = Synthetic
source                 1..449
                       mol_type = protein
                       organism = synthetic construct
SEQUENCE: 340
EVQLLESGGG LVQPGGSLRL SCAASGFTFS SYSMNWVRQA PGKGLEWVAV ISYDGRIKDY    60
ADSVKGRFTI SRDNSKNTLY LQMNSLRAED TAVYYCARVR GFSFWFDPWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                     449

SEQ ID NO: 341         moltype = AA   length = 449
FEATURE                Location/Qualifiers
REGION                 1..449
                       note = Synthetic
source                 1..449
                       mol_type = protein
                       organism = synthetic construct
SEQUENCE: 341
EVQLLESGGG LVQPGGSLRL SCAASGFTFS SYSMNWVRQA PGKGLEWVAV ISYDGRIKDY    60
ADSVKGRFTI SRDNSKNTLY LQMNSLRAED TAVYYCARVR GFSFWFDPWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPRRPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                     449

SEQ ID NO: 342         moltype = AA   length = 449
FEATURE                Location/Qualifiers
```

```
REGION                      1..449
                            note = Synthetic
source                      1..449
                            mol_type = protein
                            organism = synthetic construct
SEQUENCE: 342
EVQLLESGGG LVQPGGSLRL SCAASGFTFS SYSMNWVRQA PGKGLEWVAV ISYDGRIKDY    60
ADSVKGRFTI SRDNSKNTLY LQMNSLRAED TAVYYCARVR GFSFWFDPWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLAGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 343              moltype = AA  length = 445
FEATURE                     Location/Qualifiers
REGION                      1..445
                            note = Synthetic
source                      1..445
                            mol_type = protein
                            organism = synthetic construct
SEQUENCE: 343
EVQLLESGGG LVQPGGSLRL SCAASGFTFS SYSMNWVRQA PGKGLEWVAV ISYDGRIKDY    60
ADSVKGRFTI SRDNSKNTLY LQMNSLRAED TAVYYCARVR GFSFWFDPWG QGTLVTVSSA   120
STKGPSVFPL APCSRSTSES TAALGCLVKD YFPEPVTVSW NSGALTSGVH TFPAVLQSSG   180
LYSLSSVVTV PSSNFGTQTY TCNVDHKPSN TKVDKTVERK SCVECPPCPA PPVAGPSVFL   240
FPPKPKDTLM ISRTPEVTCV VVDVSHEDPE VQFNWYVDGV EVHNAKTKPR EEQFNSTFRV   300
VSVLTVVHQD WLNGKEYKCK VSNKGLPAPI EKTISKTKGQ PREPQVYTLP PSREEMTKNQ   360
VSLTCLVKGF YPSDIAVEWE SNGQPENNYK TTPPMLDSDG SFFLYSKLTV DKSRWQQGNV   420
FSCSVMHEAL HNHYTQKSLS LSPGK                                        445

SEQ ID NO: 344              moltype = AA  length = 449
FEATURE                     Location/Qualifiers
REGION                      1..449
                            note = Synthetic
source                      1..449
                            mol_type = protein
                            organism = synthetic construct
SEQUENCE: 344
EVQLLESGGG LVQPGGSLRL SCAASGFTFS SYSMNWVRQA PGKGLEWVAV ISYDGRIKDY    60
ADSVKGRFTI SRDNSKNTLY LQMNSLRAED TAVYYCARVR GFSFWFDPWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPEAAGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 345              moltype = AA  length = 449
FEATURE                     Location/Qualifiers
REGION                      1..449
                            note = Synthetic
source                      1..449
                            mol_type = protein
                            organism = synthetic construct
SEQUENCE: 345
EVQLLESGGG LVQPGGSLRL SCAASGFTFS SYSMNWVRQA PGKGLEWVAV ISYDGRIKDY    60
ADSVKGRFTI SRDNSKNTLY LQMNSLRAED TAVYYCARVR GFSFWFDPWG QGTLVTVSSA   120
STKGPSVFPL APSSKSTSGG TAALGCLVKD YFPEPVTVSW NSGALTSGVH TFPAVLQSSG   180
LYSLSSVVTV PSSSLGTQTY ICNVNHKPSN TKVDKRVEPK SCDKTHTCPP CPAPELLGGP   240
SVFLFPPKPK DTLMISRTPE VTCVVVDVSH EDPEVKFNWY VDGVEVHNAK TKPREEQYNS   300
TYRVVSVLTV LHQDWLNGKE YKCKVSNKAL PAPIEKTISK AKGQPREPQV YTLPPSREEM   360
TKNQVSLTCL VKGFYPSDIA VEWESNGQPE NNYKTTPPVL DSDGSFFLYS KLTVDKSRWQ   420
QGNVFSCSVM HEALHNHYTQ KSLSLSPGK                                    449

SEQ ID NO: 346              moltype = AA  length = 209
FEATURE                     Location/Qualifiers
REGION                      1..209
                            note = Dectin-2
source                      1..209
                            mol_type = protein
                            organism = Homo sapiens
SEQUENCE: 346
MMQEQQPQST EKRGWLSLRL WSVAGISIAL LSACFIVSCV VTYHFTYGET GKRLSELHSY    60
HSSLTCFSEG TKVPAWGCCP ASWKSFGSSC YFISSEEKVW SKSEQNCVEM GAHLVVFNTE   120
AEQNFIVQQL NESFSYFLGL SDPQGNNNWQ WIDKTPYEKN VRFWHLGEPN HSAEQCASIV   180
FWKPTGWGWN DVICETRRNS ICEMNKIYL                                    209
```